(12) United States Patent
Boyers et al.

(10) Patent No.: US 6,982,006 B1
(45) Date of Patent: Jan. 3, 2006

(54) METHOD AND APPARATUS FOR TREATING A SUBSTRATE WITH AN OZONE-SOLVENT SOLUTION

(76) Inventors: David G. Boyers, 558 Fir La., Los Altos, CA (US) 94024; Jay Theodore Cremer, Jr., 2181 Park Blvd., Palo Alto, CA (US) 94306

( * ) Notice: Subject to any disclaimer, the term of this patent is extended or adjusted under 35 U.S.C. 154(b) by 0 days.

(21) Appl. No.: 09/693,012

(22) Filed: Oct. 19, 2000

Related U.S. Application Data

(60) Provisional application No. 60/160,435, filed on Oct. 19, 1999.

(51) Int. Cl.
*C23G 1/02* (2006.01)

(52) U.S. Cl. .............................. 134/3; 134/1; 134/1.1; 134/1.2; 134/1.3; 134/2; 134/19; 134/21; 134/24; 134/26; 134/28; 134/30; 134/34; 134/35; 134/36; 134/37; 134/41; 134/42; 134/902

(58) Field of Classification Search .................... 134/1, 134/1.1, 1.2, 2–3, 1.3, 19, 21, 24, 26, 28, 134/30, 34–37, 41, 42, 902
See application file for complete search history.

(56) References Cited

U.S. PATENT DOCUMENTS

| | | | |
|---|---|---|---|
| 3,751,225 A | 8/1973 | Karlson | |
| 4,341,592 A | 7/1982 | Shortes et al. | |
| 5,069,880 A | 12/1991 | Karlson | |
| 5,071,485 A | 12/1991 | Matthews et al. | |
| 5,266,275 A | 11/1993 | Faddis | |
| 5,344,622 A | 9/1994 | Faddis et al. | |
| 5,447,640 A | 9/1995 | Omi et al. | |
| 5,464,480 A | 11/1995 | Matthews | |
| 5,484,549 A | 1/1996 | Hei et al. | |
| 5,516,730 A | 5/1996 | Pirooz et al. | |
| 5,520,893 A | 5/1996 | Kasting, Jr. et al. | |
| 5,534,297 A * | 7/1996 | Ogisu et al. | 427/322 |
| 5,567,444 A * | 10/1996 | Hei et al. | 134/2 |
| 5,716,458 A * | 2/1998 | Machino | 134/1 |
| 5,895,272 A | 4/1999 | Li | |
| 5,971,272 A | 10/1999 | Hsiao | |
| 6,080,531 A | 6/2000 | Carter et al. | |

(Continued)

FOREIGN PATENT DOCUMENTS

EP 0867924 9/1998

(Continued)

OTHER PUBLICATIONS

The Effect of Temperature on an Ozonated Water Photoresist Strip Process by Nelson et al.*

(Continued)

*Primary Examiner*—Sharidan Carrilo
(74) *Attorney, Agent, or Firm*—Joseph Smith

(57) ABSTRACT

A general method and apparatus for treating materials at high speed comprises the steps of dissolving a relatively high concentration ozone gas in a solvent at a relatively low predetermined temperature T1 to form an ozone-solvent solution with a relatively high dissolved ozone concentration, and heating either the ozone-water solution or the material to be treated or both, the ozone-solvent solution and the material to be oxidized with a point-of-use heater to quickly increase the temperature to a predetermined higher temperature T2>T1, and applying the ozone-solvent solution to said material(s) whereby the heated ozone-water solution will have a much higher dissolved ozone concentration at said higher temperature, than could be achieved if the ozone gas was initially dissolved in water at said higher temperature.

39 Claims, 19 Drawing Sheets

U.S. PATENT DOCUMENTS 6,273,108 B1    8/2001    Bergman et al.

FOREIGN PATENT DOCUMENTS

| EP | 0994505 | 4/2000 |
|---|---|---|
| JP | 058496 | 2/2000 |
| JP | 058496 A2 | 2/2000 |
| WO | WO99/21798 | 5/1999 |
| WO | WO98/42013 | 9/1999 |
| WO | WO99/50898 | 10/1999 |
| WO | WO99/52654 | 10/1999 |
| WO | WO 00/70656 | 11/2000 |
| WO | WO 00/70667 | 11/2000 |
| WO | WO10/07177 | 2/2001 |

OTHER PUBLICATIONS

Decomposition of Ozone in Aqueous Acetic Acid Solutions by Sehested et al.*

Bergman, E.; Castle, H.; Melli, M.; Magrin, M. "Photoresist Strip Process Using Ozone diffusion Through a Controlled Aqueous Boundary Layer," Electronic Meeting Abstract of paper to be presented at Sixth International Symposium on Cleaning Technology inSemiconductor Device Manufacturing at the 1999 Joint International Meeting of the Electrochemical Society in Honolulu, Hawaii; Jul. 1, 1999.

Bergman, E.; Melli, M.; Magrin, M. "Photoresist Strip Process Using Ozone Diffusion Through a Controlled Aqueous Boundary Layer, " presented on October 20th at the Sixth international Symposium on Cleaning Technology in Semiconductor Device Manufacturing at the 1999 Joint International Meeting of the Electrochemical Society in Honolulu, Hawaii, Published in Cleaning Technology in Semiconductor Device Manufacturing VI, R. E. Novak,, J. Ruzyllo, and T. Hattori, Editors, The Electrochemical Society Proceedings Series, vol. 99-36, Pennington. NJ, May 23, 2000, pp. 399-406.

Butterbaugh, J.W.; Olson, E.D. ' "Silicon Critical Cleaning with Ozone, HF, and HCI in a Spray Acid Processor, " Electronic Meeting Abstract of paper to be presented at Sixth international Symposium on Cleaning Technology in Semiconductor Device Manufacturing at the 1999 Joint International Meeting of the Electrochemical Society in Honolulu, Hawaii, Published in Cleaning Technology in Semiconductor Device Manufacturing VI, R.E. Novak,, J. Ruzyllo, and T. Hattori, Editors, The Electrochemical Society Proceedings Series, vol. 99-36, Pennington. NJ, May.23,2000, pp. 399-406.

Butterbaugh, J.W.; Olson, E.D. ' "Silicon Critical Cleaning with Ozone, HF, and HCI in a Spray Acid Processor, " presented on Oct. 20th at the Sixth International Symposium on Cleaning Technology in Semiconductor Device Manufacturing at the 1999 Joint International Meeting of the Electrochemical Society in Honolulu, Hawaii, Published in Cleaning Technology in Semiconductor Device Manufacturing VI, R.E. Novak,, J. Ruzyllo, and T. Hattori, Editors, The Electrochemical Society Proceedings Series,, vol. 99-36, Pennington. NJ, May. 23, 2000 pp. 31-36.

CHOOI, S.Y.M.; Ee, P.Y.; Sih, V.K.T.; and Zhou, M.S.; Bergman, E.J., "Application of Ozanated Aqueous Solutions to Photoresist Strip and Ash Residue Removal Following Plasma Polysilicon Etch, " Electronic Meeting Abstract of paper to be presented at Sixth International Symposium on Cleaning Technology in Semiconductor Device Manufacturing at the 1999 Joint International Meeting of the Electrochemical Society in Honolulu, Hawaii,; July 1, 1999.

CHOOI, S.Y.M.; Ee, P.Y.; Sih, V.K.T.; and Zhou, M.S.; Bergman, E. J., "Application of ozonated Aqueous Solutions to Photoresist Strip and Ash Residue Removal Following Plasma Polysilicon Etch. " presented on Oct. 20th at the Sixth International Symposium on Cleaning Technology in Semiconductor Device Manufacturing at the 1999 Joint International Meeting of the Electrochemical Society in Honolulu, Hawaii, Published in Cleaning Technology in Semiconductor Device Manufacturing VI, R.E. Novak,, J. Ruzyllo, and T. Hattori, Editors, The Electrochemical Society Proceedings Series, vol. 99-36, Pennington, NJ, May. 23, 2000, pp. 212-218.

Christenson, K.; Nelson, S., Olim, M., Nelson, G. "Mass Transfer in DI:03 Resist Stripping ", Electrochemical Society Proceedings, Proceedings of the Fifth International Symposium on Cleaning Technology in Semiconductor Device Manufacturing, vol. 97-35, p. 480-487, 1997.

Christenson, K.; Nelson, S.; Fussy, M. "Optimizing at Hot DI03 Resisit Strip Process, " Electronic Meeting Abstract of paper to be presented at Sixth International Symposium on Cleaning Technology in Semiconductor Device Manufacturing at the 1999 Joint International Meeting of the Electrochemical Society in Honolulu, Hawaii; Jul. 1, 1999.

Christenson, K.; "Rinsing: A Critical Process in Contamination Removal", Journal of the Institute of Environmental Sciences, vol. 40, No. 5, Sep.-Oct. 1997, Institute of Environmental Sciences, Mount Prospect, Illinois, USA, p. 45-50. (ref. # 42).

Christenson, Kurt K.; Nelson, Steve: olim, Moshe; Nelson, Greg, "Deionized water helps remove water stripping 'resist'-ance", Source: Precision Cleaning v 6 n 4 Apr. 1998 Witter Publ Co. p. 10,12,14-16, 19.

Dax, M., "Acid-Free Process Removes Photoresist", Semiconductor International 1996, 9.74 (ref. #43).

De Gendt, S.; Lux, M.; Claes, M.; Jassal, A.S.; Van Hoeymissen, J.; Lagrange, S.; Bergman, E.; Mertens, P.W.; and Heyns, M. M. "Evaluation of Ozonated Water Spray for Resist Cleaning Applications," Electronic Meeting Abstract of paper to be presented at Sixth International Symposium on Cleaning Technology in Semiconductor Device Manufacturing at the 1999 Joint International Meeting of the Electrochemical Society in Honolulu, Hawaii; Jul. 1, 1999.

De Gendt, S.; Lux, M.; Claes, M.; Jassal, A.S.; Van Hoeymissen, J.; Lagrange, S.; Bergman, E.; Mertens, P.W.; and Heyns, M.M. "Evaluation of Ozonated Water Spray for Resist Cleaning Applications," presented on Oct. 20th at the Sixth International Symposium on Cleaning Technology in Semiconductor Device Manufacturing at the 1999 Joint International Meeting of the Electrochemical Society in Honolulu, Hawaii, Published in Cleaning Technology in Semiconductor Device Manufacturing VI, R.E. Novak,, J. Ruzyllo, and T. Hattori, Editors, The Electrochemical Society Proceedings Series, vol. 99-36, Pennington. NJ, May. 23, 2000, pp. 391-398.

De Gendt, S.; Snee, P.; Cornelissen, I.; Lux, M.; Vos, R.; Mertens, P; Knotter, K.; Heyns, M. "A Novel Resist and Post-Etch Residue Removal Process Using Ozonated Chemistries", Symp. on VLSI Technology digest of Technical Papers, p. 168-169, 1998.

De Gendt, S.; Wauters, J.; Heyns,M. "A Novel Resist and Post-Etch Residue Removal Process Using Ozonated Chemistry, " Solid State Technology, p. 57, Dec. 1998.

Hattori, T. "Environmentally Friendly Single-Wafer Spin Cleaning," Solid State Technology, Nov. 1999, pp. 73-80.

Heyns, M; Mertens, P.W.;Ruzyllo, J; Lee, Y.M. "Advanced Wet and Dry Cleaning Coming Together for Next Generation, " Solid State Technology, pp. 37-47, Mar. 1999.

Kashkoush, I.; Novak, R.;Matthews, R.;Lamarra, M. "An Alternative to Conventional Post-Ash Resist Stripping", Future Fab International, Summer 1997, p. 11-20.

Kashkoush,I.; Matthews, R.; Novak,R. "Photoresist Stripping Using Ozone/Deionized Water Chemistry", Materials Research Society Symposium Proceedings Science and Technology of Semiconductor Surface Preparation Proceedings of the 1997 MRS Spring Meeting Apr. 1-3 1997 v 477 1997 San Francisco, CA, USA Sponsored by: MRS Warrendale PA USA p. 21-26.

Kleemeier, W.; Leon, V.; Graham, S., "Plasma etch residue and photoresist removal utilizing environmentally benign process chemicals", Source: Diffusion and Defect Data Pt.B: Solid State Phenomena v 65-66 Sep. 21-23 1998 1999 Sponsored by: Ashland Chemical; ASTex; Atomika Instruments; Cascade Scientific; et al Scitec Publ Ltd. p. 143-152.

Kubo, K.; Ojima, S. ; Sakata, Y. ; Kato, M. ;Toda, M.; Ohmi, T. "The Impact of Radical Activated Ultra Pure Water", Annual Semiconductor Pure Water and Chemicals Conference Proceedings, Proceedings of 1996 15th Annual Semiconductor Pure Water and Chemicals Conference, Ultrapure Water & Chemical Sessions, 1996, Wafer Cleaning Session, Santa Clara, CA, USA, p. 196-214.

Lacasse, S.; Leon, V.; "Integrated Aqueous/Ozone Process for Plasma Etch Residue and Photoresist Removal," Electronic Meeting Abstract of paper to be presented at Sixth International Symposium on Cleaning Technology in Semiconductor Device Manufacturing at the 1999 Joint international Meeting of the Electrochemical Society in Honolulu, Hawaii; Jul. 1, 1999.

Lacasse, S.; Leon, V.; "integrated Aqueous/Ozone Process for Plasma Etch Residue and Photoresist Removal," presented on Oct. 20th at the Sixth International Symposium on Cleaning Technology in Semiconductor Device Manufacturing at the 1999 Joint Internatinal Meeting of the Electrochemical Society in Honolulu, Hawaii, Published in Cleaning Technology in Semiconductor Device Manufacturing VI, R.E. Novak,, J. Ruzyllo, and T. Hattori, Editors, The Electrochemical Society Proceedings Series, vol. 99-36, Pennington. NJ, May. 23, 2000, pp. 197-203.

Lester, M., "Ozone-Water Process Removes Back-End Post-Etch Resist/Residue," Semiconductor International, vol. 23, No. 10, pp. 64 Sep., 2000.

MA, S.; Parker, R.; Kavari, R.; Leal, I.; Boyers, D.G.; and Cremer, J.T., "Evaluation of a New Ozone-Water Process for Backend Post-Metal Etch or Post-Oxide Etch Resist or Residue Removal," Proc. Semiconductor Pure Water and Chemicals Conference, pp. 360-386, Mar. 2000, Santa Clara, CA.

MA, S.; Parker, R.; Kavari, R.; Leal, I.; Boyers, D.G.; and Cremer, J.T., "An Evaluation of the HotOzone™ Process: A New Post Etch Resist and Residue Removal Process," Proc. International Interconnect Technology Conference, pp. 46-48, Jun. 2000, San Francisco, CA.

Matthew, R. "A New Aqueous Based Technology Employing Subambient Temperature Deionized Water and Ozone for Removing Organics", Annual Semiconductor Pure Water and Chemicals Conference Proceedings, Proceedings of 1998 17th Annual Semiconductor Pure Water and Chemicals Conference, Ultrapure Water & Chemical Sessions, Mar. 2-6, 1998, Wafer Cleaning Session, Santa Clara, CA, USA, p. 359-374.

Morita, M.; Kim, J.; Ohmi, T., "Cleaning of Noble Metals on Silicon Wafer Surface by Ozonized Ultra Pure Water", Annual Semiconductor Pure Water and Chemicals Conference Proceedings, Proceedings of 1996 15th Annual Semiconductor Pure Water and Chemicals Conference, Ultrapure Water & Chemical Sessions, 1996, Wafer.

Narayanswami, N.; Nelson, S. "Dynamics of Mass Transfer on a Wafer Surface in ozonated Water Processing for Photoresist Removal," presented at the Ultra Clean Processing for Silicon Surfaces Meeting, Belgium, Sep. 21-23, 1998.

Nelson, S. "Using an Ozone Water Last Cleaning Process to Research the Effects of Process Parameters on Wafer Contamination", Annual Semiconductor Pure Water and Chemicals Conference Proceedings, Proceedings of 1996 15th Annual Semiconductor Pure Water and Chemicals Conference, Ultapure Water & Chemical Sessions, 1996, Wafer Cleaning Session, Santa Clara, CA, USA, p. 230-242.

Nelson, S.; Christenson, K. "The Effect of Temperature on an Ozonated Water photoresist Strip Process," presented on Oct. 20th at the Sixth International Symposium on Cleaning Technology in Semiconductor Device Manufacturing at the 1999 Joint International Meeting of the Electrochemical Society in Honolulu, Hawaii, Published in Cleaning Technology in Semiconductor Device Manufacturing VI, R.E. Novak,, J. Ruzyllo, and T. Hattori, Editors, The Electrochemical Society Proceedings Series, vol. 99-36, Pennington. NJ, May. 23, 2000,, pp.189-196.

Nelson, S.l.; Carter, L.E., "Process using ozonated water solutions to remove photoresist after metallization" Diffusion and Defect Data Pt.B: Solid State Phenomena v 65-66 Sep. 21-23, 1998, 1999 Sponsored by: Ashland Chemical; ASTeX; Atomika Instruments; Cascade Scientific; et al Scitec Publ Ltd. p. 287-290.

Ohmi, T. "Total Room Temperature Wet Cleaning for Si Substrate Surface," J. Electrochem. Society, vol. 143, No. 9, Sep. 1996, pp. 2957-2964.

Ohmi, T. "Total Room Temperature Wet Cleaning of Silicon Surfaces," Semiconductor International, Jul. 1996, pp. 323-338.

Ohmi, T.; Isagawa, T.; Kogure, M.; Imaoka, T. Native Oxide Growth and Organic Impurity Removal on Si Surface with Ozone-Injuected Ultra-pure Water, J. Electrochem. Society, vol. 140, No. 3, Mar. 1993, pp. 804-810.

Wei, J.; Verhaverbake, S.; Parker, J. "Ozone Use for Post-ashing Resist Stripping; Mechanisms and Recent Findings", Annual Semiconductor Pure Water and Chemicals Conference Proceedings, Proceedings of 1997 16th Annual Semiconductor Pure Water and Chemicals Conference, Part 2, Mar. 3-7 1997, vol. II Chemical Session, 1997 Santa Clara, CA, USA, p. 81-98.

Wolke, K.; Riedel, T.; Huag, R.; De Gendt, s.; Heyns, M. M.; Meuris, M., "Application of Moist Ozone Gas Phase of Removal of Resist and Organic Contamination in a Novel tank Type Processor", presented on Oct. 20th at the Sixth International Symposium on Cleaning Technology in Semiconductor Device Manufacturing at the 1999 Joint International Meeting of the Electrochemical Society in Honolulu, Hawaii, Published in Cleaning Technology in Semiconductor Device Manufacturing VI, R.E. Novak,, J. ruzyllo, and T. Hattori, Editors, The Electrochemical Society Proceedings Series, vol. 99-36, Pennington. NJ, May. 23, 2000, pp. 205-211.

Adler, G. A.; Hill, G. R.., "Kinetics and Mechanism of HYdoxide Ion Catalyzed Ozone Decomposition in Aqueous Solution," J. Am. Chem. Soc. vol. 72, 1950, pp. 1984.

Forni, L.; Bahnemann, D. Hart, E.J., Mechanism of the Hydroxide Ion Initiated Decomposition of Ozone in Aqueous Solution, J. Phys. Chem. vol. 86, pp. 255-259, 1982.

Grove, A. S., Physics and Technology of Semiconductor Devices, John Wiley and Sons, 1967., pp. 10-18.

Hoigne, J. and Bader, H. "The Role of Hydroxyl Radical Reactions in Ozonation Processes in Aqueous Solutions", Water Research, vol. 10, pp. 377-388, Pergamon Press 1976.

Hoigne, J. and Bader, H. Rate Constants of direct reactions of ozone with organic and inorganic compounds in water. I. Non-dissociating organic compounds, Water Research, vol. 17, pp. 173-184, pp. 185-194, 1983.

Hoigne, J. and Bader, H. Rate Constants of direct reactions of ozone with organic in inorganic compounds in water. II Dissociating Organic Compounds, Water Research, vol. 17, pp. 185-194, 1983.

Hoigne, J.; Bader, H.; Haag, W.R.; Staehelin, J., Rate Constants of Reactions of Ozone with Organic and Inorganic Compounds in Water—III, Water Research vol. 19, No. 8, pp. 993-1004, 1985.

Sehested, K.; Corfitzen, H.; Holcman, J.; Hart, E. J.; "Decomposition of Ozone in Aqueous Acetic Acid Solutions (pH 0-4)," J. Phys. Chem., vol. 96, 1992, pp. 1005-1009.

Broadwater, W. T.; Hoehn, R.C.; King, P.H. "Sensitivity of Three Selected Bacterial Species to Ozone," Applied Microbiology, 26(3):391-393 (1973).

Rickloff, J.R. An Evaluation of the Sporicidal Activity of Ozone, Appl. Environ. Microbiol., 53:686-686 (1987).

Wickramanayake, G.B., Rubin, A.J.; Sproul, O. J.,. "Inactivation of Naegleria and Giardia cysts in Water by Ozonation", Journal WPCF, vol. 56, No. 8, Aug. 1984m pp. 983-988.

Wickramanayake, G.B., Sproul, O.J. "kinetics of the inactivation of Microorganisms", pp.72-84, Disinfection, Sterilization, and Preservation, Editor: Seymor S. block, 4th Edition, Neal and Febiger, Philadelphia, 1991.

Wickramanayake, G.B.; Sproul, OJ., "Ozone Concentration and Temperature Effects on Disinfection Kinetics,", Ozone Science and Engineering vol. 10, pp. 123-135, 1988.

Wickramanayake, G.B., "Disinfection and Sterilization by Ozone", Chapter 10, pp. 182-190. Disinfection, Sterilization, and Preservation, Editor: Seymor s. Block 4th Edition, Neal and Febiger, Philadelphia, 1991.

Chen, G.S.;, "The Application of DI-O3 Water pm Wafer Surface Preparation," International Conference on Wafer Rinsing, Water Reclamation, and Environmental Technology for Semiconduct Manufacturing, 1999. pp. 100-123, Publisher: Industrial Technology Research Institute, Hsin-Chu, Taiwan.

* cited by examiner

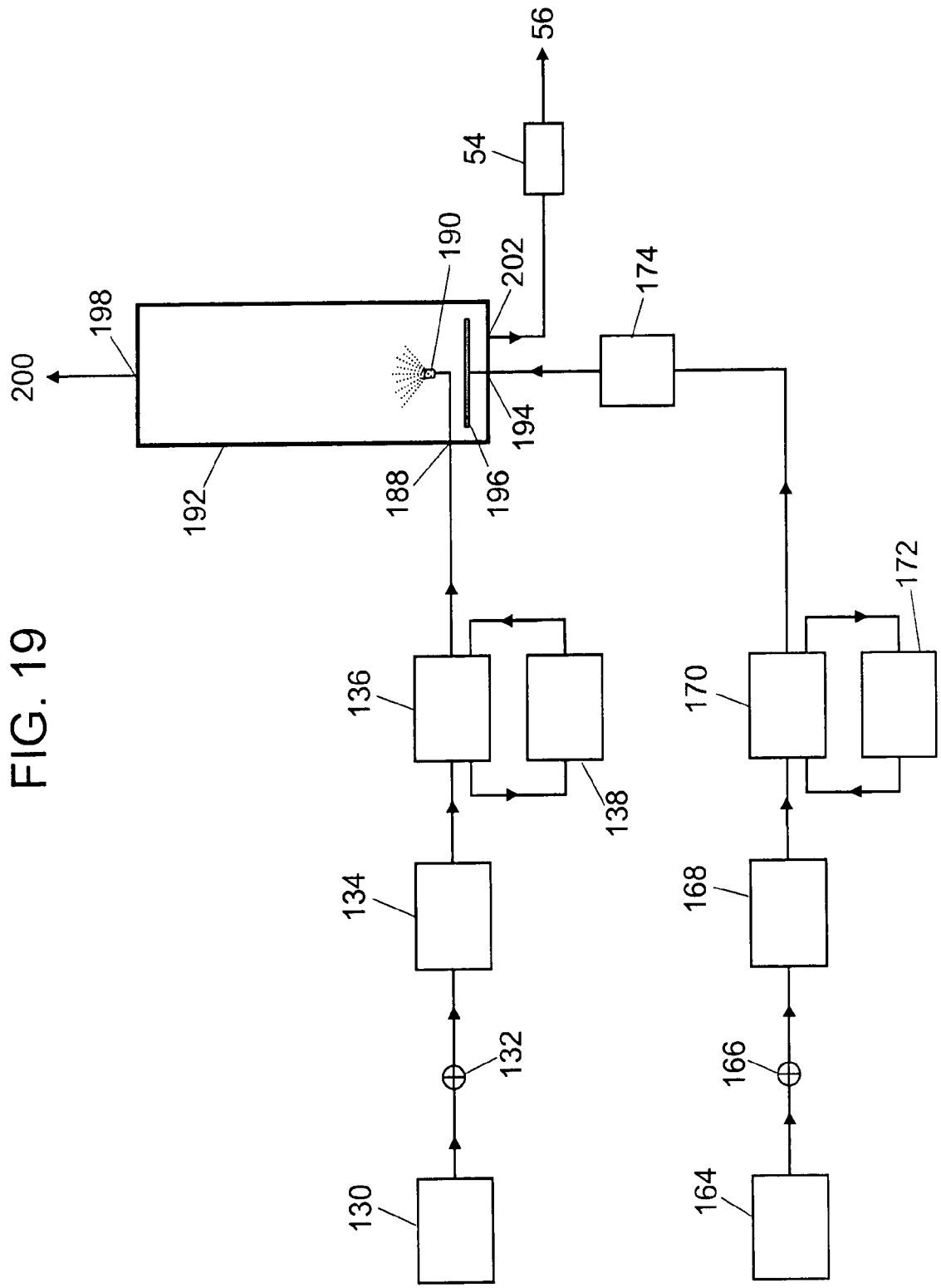

METHOD AND APPARATUS FOR TREATING A SUBSTRATE WITH AN OZONE-SOLVENT SOLUTION

This application claims benefit of provisional application 60/160,435, filed Oct. 19, 1999.

SUMMARY OF INVENTION

In accordance with preferred embodiments of the invention, methods and apparatus are provided for treating materials which have broad advantages over prior systems and a very wide range of applications, including materials processing, wafer processing, medical instrument sterilization, and the like). The method entails forming an ozone-solvent solution at a first temperature having a dissolved ozone concentration and reacting the ozone-solvent solution with the material at a second temperature which is higher than said first temperature. In a preferred mode the reacting step comprises heating at least one of the ozone-solvent solution and the material, thereby causing said ozone-solvent solution to have a higher dissolved ozone concentration while reacting with the material than if the ozone-solvent solution had been formed at the second temperature. Various apparatus are presented to carry out these treatment processes.

For example, in a preferred embodiment of the invention, a system is provided for treating a substrate with an ozone-solvent solution which comprises a supply of an ozone-solvent solution formed at a first temperature which delivers a generally continuous supply of the ozone-solvent solution at the first temperature. The system includes a heater coupled to receive the ozone-solvent solution at the first temperature from the supply and heats the ozone-solvent solution received, and provides a generally continuous supply of heated ozone-solvent solution. The systems also includes an applicator fluidly coupled the heater to receive the generally continuous supply of the heated ozone-solvent solution, the applicator having an outlet configured to direct the heated ozone-solvent solution at a second temperature greater than the first temperature toward a substrate.

Outlined below are some of the advantages the various processes and how they are achieved:

Higher oxidation rate: provides a method for oxidizing materials using a solution of ozone gas dissolved in solvent which can produce much higher oxidation rates than can be achieved by current methods;

Environmentally benign chemical: provides a method for oxidizing materials at high speed which uses an environmentally benign, residue free chemistry thereby reducing chemical disposal cost;

Increased user safety and reduced chemical cost and reduced chemical disposal cost: provides a method for oxidizing materials at high speed where the oxidizing chemical can be created and destroyed at the point of manufacture thereby increasing user safety, reducing chemical cost and reducing chemical disposal cost;

Additional chemicals can be injected with minimal impact on dissolved ozone concentration or injected-chemical concentration: provides a method for oxidizing materials using a solution of ozone gas dissolved in a solvent which may include injecting additional chemicals which significantly reduce the time available for injected chemicals to react with the ozone-solvent solution and thereby minimizes any decrease in dissolved ozone concentration or injected chemical concentration caused by such a reaction;

Different injected chemicals may be added to the ozone-water solution during different phases of the materials processing cycle: provides a method for oxidizing materials using a solution of ozone gas dissolved in water which may include a means to select the mix of chemical (s) that are dispensed onto the surface of the materials to be oxidized during a given phase of the materials processing cycle;

DI water and other chemicals may be introduced in lieu of the ozone-water solution during different phases of the materials processing cycle: provides a method for oxidizing materials using a solution of ozone gas dissolved in water which may include a means for injecting chemicals or DI water in lieu of the ozone-water solution and thereby provide a means to selectively dispense chemicals or DI water onto the surface of the materials to be oxidized during a given phase materials processing cycle.

Wafer Processing Advantages

Higher removal rates: provides a method for removing photoresist, post ash photoresist residue, post-etch residue, and other organic materials from semiconductor wafers, flat panel display substrates, and the like which can produce much higher removal rates than can be achieved by current methods;

Lower process temperature and lower corrosion potential: provides a method for removing photoresist, post ash photoresist residue, post-etch residue, and other organic materials from semiconductor wafers, flat panel display substrates, and the like which can produce much higher removal rates at lower temperatures than can be achieved by current methods and thereby reduce the potential for metal corrosion;

Practical throughputs in both single wafer and batch processing systems: provides a method for removing photoresist, post ash photoresist residue, post-etch residue, and other organic materials from semiconductor wafers, flat panel display substrates, and the like which can achieve practical throughputs in both single wafer processing systems and batch wafer processing systems;

Readily retrofitted at low marginal cost: provides a method for removing photoresist, post ash photoresist residue, post-etch residue, and other organic materials from semiconductor wafers, flat panel display substrates, and the like which can be readily retrofitted at low marginal cost to many existing single wafer and batch wafer spin processing tools;

Readily integrated into a cluster tool: provides a method for removing photoresist, post ash photoresist residue, post-etch residue, and other organic materials from semiconductor wafers, flat panel display substrates, and the like which can be readily integrated into a cluster tool comprising multiple processes in a single platform;

Readily integrated with a spin rinse and spin dry step: provides a method for removing photoresist, post ash photoresist residue, post-etch residue, and other organic materials from semiconductor wafers, flat panel display substrates, and the like which can be readily integrated with a spin rinse and spin dry step provides the basis of a dry-in dry-out cleaning process;

Low cost processing chamber: provides a method for removing photoresist, post ash photoresist residue, post-etch residue, and other organic materials from semiconductor wafers, flat panel display substrates, and the like which does not require that high concentration ozone gas be introduced into the process chamber thereby significantly reducing the cost of the wafer processing chamber;

Increased user safety: provides a method for removing photoresist, post ash photoresist residue, post-etch residue, and other organic materials from semiconductor wafers, flat panel display substrates, and the like which does not require that high concentration ozone gas be introduced into the process chamber thereby significantly increasing user safety;

Reduced corrosion potential: provides a method for removing photoresist, post ash photoresist residue, post-etch residue, and other organic materials from semiconductor wafers, flat panel display substrates, and the like which does not require that high concentration ozone gas be introduced into the process chamber thereby eliminating high concentration ozone gas as a source of corrosion;

Nitrogen blanketed process chamber: provides a method for removing photoresist, post ash photoresist residue, post-etch residue, and other organic materials from semiconductor wafers, flat panel display substrates, and the like in which an inert gas such a nitrogen can be introduced into the process chamber;

Increased user safety: provides a method for removing photoresist, post ash photoresist residue, post-etch residue, and other organic materials from semiconductor wafers, flat panel display substrates, and the like in which the dissolved ozone concentration quickly falls to very low levels immediately downstream of the point of application thereby further increasing user safety;

Medical Instrument Sterilization Advantages

Higher sterilization rates: provides a method for sterilization of medical instruments at moderate temperatures which can achieve much higher sterilization rates than can be achieved by current methods;

Residue free sterilant: provides a method for sterilization of medical instruments at moderate temperatures which utilizes a residue free sterilant and thereby eliminate the risk of carry-over of sterilant chemical residue to the patient and reduce the cost of chemical disposal;

No water rinse required: provides a method for sterilization of medical instruments at moderate temperatures which utilizes a residue free sterilant and thereby eliminate the need for a separate water rinse step;

Increased user safety and reduced chemical cost and reduced chemical disposal cost: provides a method for sterilization of medical instruments at moderate temperatures in which the active component is created for each cycle and then destroyed at end of the cycle thereby increasing user safety, decreasing chemical cost, and decreasing chemical disposal cost;

Lower consumables cost: provides a method for sterilization of medical instruments at moderate temperatures which has a lower consumables cost ($0.50 per cycle) than leading processes;

Single-use sterilant always at full concentration: provides a method for sterilization of medical instruments at moderate temperatures which is a single pass design in which sterilant is sprayed onto instrument surfaces and then sent to the drain thereby eliminating the degradation in the sterilant concentration otherwise caused by the retention in the sterilant solution of serum and other organic residue washed from the processed instruments;

Low cost sterilization processing chamber: provides a method for sterilization of medical instruments at moderate temperatures which does not require that high concentration ozone gas be introduced into the process chamber thereby significantly reducing the cost of the wafer processing chamber;

Increased user safety: provides a method for sterilization of medical instruments at moderate temperatures which does not require that high concentration ozone gas be introduced into the process chamber thereby significantly increasing user safety;

Reduced potential for instrument materials degradation: provides a method for sterilization of medical instruments at moderate temperatures which does not require that high concentration ozone gas be introduced into the process chamber thereby eliminating high concentration ozone gas as a source of corrosion of metals or degradation of elastomers or plastics;

Reduced potential for instrument materials degradation: provides a method for sterilization of medical instruments at moderate temperatures in which an inert gas such a nitrogen can be introduced into the process chamber thereby eliminating high concentration ozone gas as a source of corrosion of metals or degradation of elastomers or plastics;

Increased user safety: provides a method for sterilization of medical instruments at moderate temperatures in which the dissolved ozone concentration quickly falls to very low levels immediately downstream of the point of application thereby further increasing user safety;

Applicable to complex shaped instruments with internal passages with large L/D: provides a method for sterilization of medical instruments at moderate temperatures which can be used with complex shaped items, or items containing internal surfaces, such as rigid and flexible endoscopes with internal passages with a large length to diameter ratio L/D.

BRIEF DESCRIPTION OF DRAWINGS

The various features of the present invention and its preferred embodiments may be better understood by referring to the following discussion and the accompanying drawings in which like reference numerals refer to like elements in the several figures.

FIG. 19 illustrates a block diagram of a method of dissolving ozone gas into water chilled water mist to from an ozone-water mist solution mixed with ozone gas.

DETAILED DESCRIPTION OF THE PREFERRED EMBODIMENTS

Figure 1:
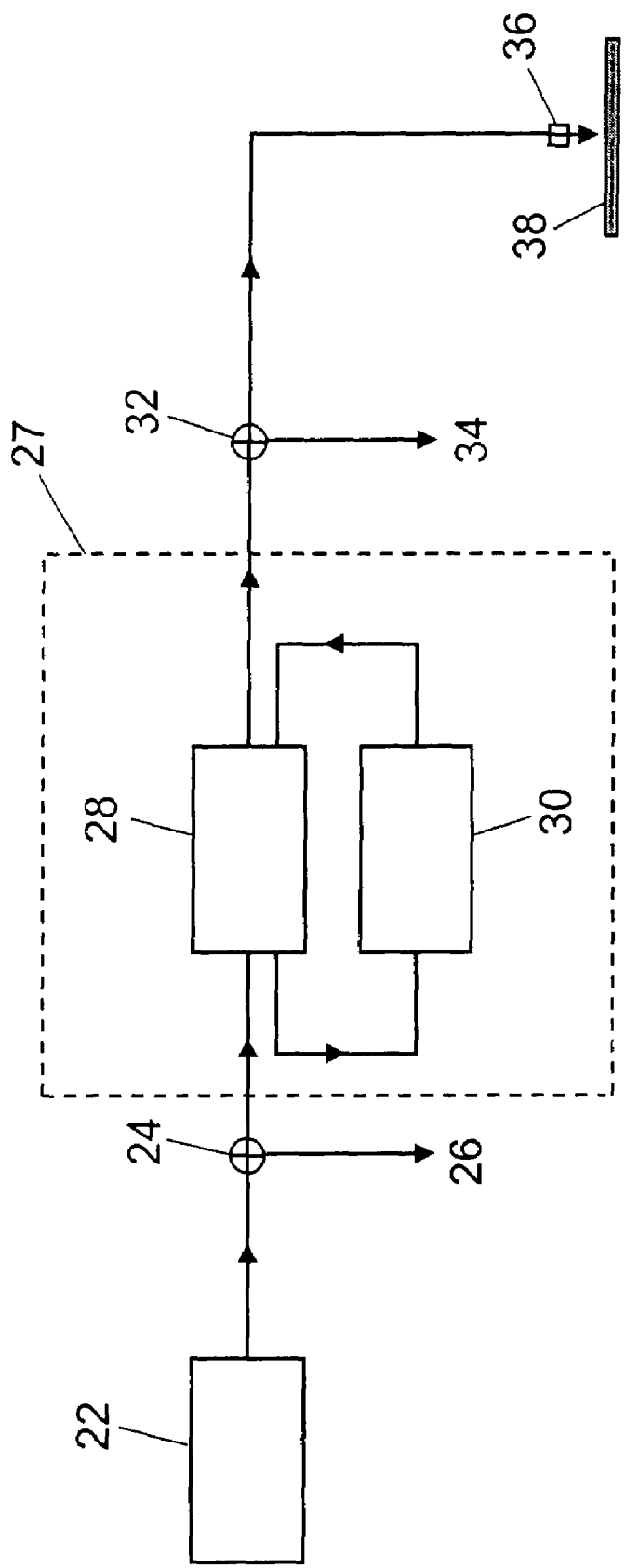
FIG. 1 illustrates a functional block diagram of a method of processing materials: A cold ozone-water solution at temperature T1 is heated to temperature T2>T1 using a liquid to liquid heat exchanger just upstream of the point of application of the ozone-water solution to the material to be processed.

Factors Determining Oxidation Rate or Removal Rate—A Model

The inventors have developed a model to help better understand the factors determining oxidation and removal rate of an organic material such as photoresist from a semiconductor wafer using an ozone-solvent solution at concentration C and temperature T. The rate of oxidation and removal of an organic layer from a substrate can be defined in terms of an etch rate. We can write an expression for the etch rate E (cm resist/sec) as $E=C*(X/\rho)*(M*S)/(M+S)$. The parameter C (g ozone/cm3) is the dissolved ozone concentration in the water far from the surface of the organic layer on a semiconductor wafer for example (the bulk concentration). The parameter X (g resist/g 0zone) is the mass of resist removed per mass of ozone consumed at the surface. If we assume that the resist is composed of chains of CH2 units which must be fully oxidized to be removed, then 3 moles of ozone are required to oxide each mole of CH2. This corresponds to 10.3 grams of ozone to fully oxidize each gram of resist. Christensen (1998) was the first to observe that etch rates for I-line photoresist are a factor of 20 higher than that predicted by the assumption of full oxidation. They concluded that the resist need only be cut into short fragments about 20 CH2 units long before the fragments become hydrophilic and float off the wafer into the stream of flowing water. The net result is that the parameter X is not (1/10.3) but about (20/10.3). The parameter $\rho$ (g resist/cm3) is the density of the resist.

Terminology: Throughout this discussion the terms ozonated water, ozone-water solution, and ozone-gas-water solution are used interchangeably. In addition, the terms etch, etch clean, clean, process, oxidize are used interchangeably. DI water is De-ionized water.

Dissolved Ozone Concentration C: When ozone is dissolved in a solvent, the maximum dissolved ozone concentration C that can be achieved after a sufficiently long transfer time, the saturation concentration, is predicted by Henry's law. According to Henry's law, the maximum solubility is proportional to the partial pressure of the ozone gas at a given temperature. Higher gas phase concentrations, high pressures, and lower solvent temperatures yield higher maximum equilibrium dissolved ozone concentrations. We have calculated the approximate equilibrium saturation concentration in mg/L (equivalent to parts per million by weight) for a gas phase concentration of 240 mg/L (15.9 weight percent), pressures of 1, 2, and 4 bar, and water (solvent) temperatures of 5 to 95 degree C. in 5 deg. C. increments. See Table 1.

TABLE 1

Solubility of ozone gas in water: The dissolved ozone concentration in mg/L as a function of the water temperature and gas pressure for a gas phase ozone concentration of 240 g/Nm3 = mg/liter (15.9 weight percent) in oxygen for a range of water temperatures.

| | p = 1 bar (14.5 psia) | p = 2 bar (29 psia) | p = 4 bar (58 psia) |
|---|---|---|---|
| 5 deg. C. | 109 | 218 | 436 |
| 10 deg. C. | 85 | 170 | 340 |
| 15 deg. C. | 66 | 132 | 264 |
| 20 deg. C. | 52 | 104 | 208 |
| 25 deg. C. | 40 | 80 | 160 |
| 30 deg. C. | 31 | 62 | 124 |
| 40 deg. C. | 24 | 48 | 96 |
| 45 deg. C. | 19 | 38 | 76 |
| 50 deg. C. | 15 | 30 | 60 |
| 55 deg. C. | 11 | 22 | 44 |
| 60 deg. C. | 9 | 18 | 36 |
| 65 deg. C. | 7 | 14 | 28 |
| 70 deg. C. | 5 | 10 | 20 |
| 75 deg. C. | 4 | 8 | 16 |
| 80 deg. C. | 3 | 6 | 12 |
| 85 deg. C. | 2.5 | 5 | 10 |

TABLE 1-continued

Solubility of ozone gas in water: The dissolved ozone concentration in mg/L as a function of the water temperature and gas pressure for a gas phase ozone concentration of 240 g/Nm3 = mg/liter (15.9 weight percent) in oxygen for a range of water temperatures.

|  | p = 1 bar (14.5 psia) | p = 2 bar (29 psia) | p = 4 bar (58 psia) |
| --- | --- | --- | --- |
| 90 deg. C. | 1.2 | 2.4 | 4.8 |
| 95 deg. C. | .9 | 1.8 | 3.6 |

Mass Transport Rate Coefficient M: The parameter M (cm/sec) is the liquid phase mass transport rate coefficient. The ozone is transported to the wafer surface by diffusion. The mass transport rate M (cm/sec)=D/$\delta$ where D (cm2/sec) is the diffusion constant of the ozone diffusing in the liquid and $\delta$ (cm) is the thickness of the stagnant layer. The diffusion constant D for ozone in water is 1.7E−5 cm2/sec at 20 deg. C. Accordingly the mass transport rate is increased when the diffusion constant is increased and/or the diffusion distance $\delta$ is decreased.

Surface Reaction Rate Constant S: The parameter S(cm/sec) is the temperature dependent surface reaction rate constant. The surface reaction rate S (cm/sec) is an exponential function of the absolute temperature T (deg. K) and the activation energy Ea of the oxidation process. In particular, S=Soexp(−Ea/KT) where K is Boltzman's constant and So is the surface reaction rate proportionality constant. The difference in etch rates of different materials at a given temperature is attributed to the difference in the magnitude of the surface reaction rate constant for the two materials.

Etching Wafers at High Temperature: An increase in temperature will increase S and the magnitude of the term (M*S)/(M+S). If the dissolved concentration remained approximately constant with an increase in temperature, then we can see that the etch rate would increase with increased temperature. However, as we have seen, the dissolved ozone concentration falls with increases in water temperature. If the temperature is such that S>>M, the etch rate becomes mass transport limited and E=C(X/$\rho$)*M. If M is larger, then the temperature at which the etch rate becomes limited by the mass transport rate M will be higher. If the temperature is higher, then the mass transport rate at which the etch rate will become mass transport limited will be higher.

Etching Wafers at Low Temperature: A decrease in temperature will decrease S and the magnitude of the term (M*S)/(M+S). If the dissolved concentration remained approximately constant with decreases in temperature, then we can see that the etch rate would decrease with a decrease in temperature. However, as we have seen, the dissolved ozone concentration rises with decreases in water temperature. If the temperature is decreased until S<<M, the etch rate becomes surface reaction rate limited and E=C(X/$\rho$)*S.

Measured Temperature Dependence of S: We made a preliminary measurement of the temperature dependence of the surface reaction rate S in our laboratory. We made the measurements of the etch rate of IBM Apex positive DUV resist under conditions where M>>S and E=SCX by etching a spinning wafer with a small diameter nozzle to produce high velocities and small values of $\delta$. We measured the etch rate at 7 deg. C., 12 deg. C., and 17 deg. C. Our measurements showed that the surface reaction rate coefficient S (cm/sec) increases by a factor of two for every 5 degree C. increase in temperature corresponding to an activation energy of about 1 eV. We found the same activation energy but larger coefficient So for SHIPLEY® 1805 positive I-line resist. This is consistent with I-line positive resist etching faster than DUV positive photoresist.

Measured Etch Rate at Different Temperatures: Our initial measured results show that the etch rate increases when the temperature is increased from 10 deg. C. to 19 deg. C. because the normalized etch rate E/C increases by a larger factor than the dissolved ozone concentration decreases. However, when the temperature is increased from 19 deg. C. to 28 deg. C., the dissolved ozone concentration decreases by a larger factor than the normalized etch rate decreases. This trend continues at all higher temperatures with the result that under equilibrium conditions the highest etch rate is achieved at about 20 deg. C.

An Approach to Achieving Very High Etch Rates: This model can provide us valuable insight into the problem. It shows that the normalized etch rate be increased by increasing the temperature and that the etch rate could be increased by increasing the temperature above 20 degree C. if we could find a method to provide a higher dissolved concentration at the elevated temperature. The present preferred embodiments utilize just such a method.

The general principal is to achieve the highest dissolved ozone concentration at a given surface reaction temperature. This can be done in a number of ways including the following:

a) heat the cold ozone-solvent solution with an in-line heater located just upstream of the point at which the ozone-solvent solution is dispensed onto the substrate. The heated ozone-solvent solution will then heat the surface of the substrate and increase the surface reaction rate. The ozone-solvent solution will retain most of the ozone dissolved at the lower temperature if the solution is not heated until the last moment.

b) heat the cold ozone-solvent solution at the point of application with a point of application heater as the solution passes over the substrate surface by for example using a radiant heater with the wavelength band chosen to be absorbed by the ozone-solvent solution. The heated ozone-solvent solution will then heat the surface of the substrate and increase the surface reaction rate.

c) heat the substrate with a point of application heater and dispense the cold ozone-solvent solution onto the surface of the heated substrate. Provide sufficient heat input to the substrate to overcome cooling effect of the cold solvent. In practice the substrate can be heated from the backside or from the front side. If the substrate is heated from the backside, the entire volume of the substrate may be heated so that the front surface, the surface to be etched, can be heated. If the substrate is heated from the front side, the entire volume of the substrate may be heated or only the front surface may be heated. The surface reaction rate at the front surface is a function of the temperature of the front surface.

d) heat the cold ozone-solvent solution and heat the substrate by for example using a radiant heater with the wavelength band chosen to be absorbed partially by the ozone-solvent solution and partially by the substrate.

The substrate surface can be heated by conduction, convection, or radiation. The surface can be heated by conduction using a heated surface such as a hot plate. The surface can be heated by convection using a hot gas or hot liquid to the front or rear surface. The substrate can be heated by radiation using a heat lamp or laser or other source of radiation. The radiation wavelength band can be chosen so that the radiation passes through the ozone-water solution with little energy deposition in the water and the majority of the energy absorbed in the surface. In fact the radiation can be chosen to be most strongly absorbed in the layer to removed (photoresist for example).

The description of the preferred embodiments for oxidizing materials at high speed is divided into three groups 1st GROUP: Heat Applied Just Upstream of the Point of Application (FIG. 1 through FIG. 11)

$2^{nd}$ GROUP: Heat Applied at the Point of Application (FIG. 12 through FIG. 16)

Figure 17:
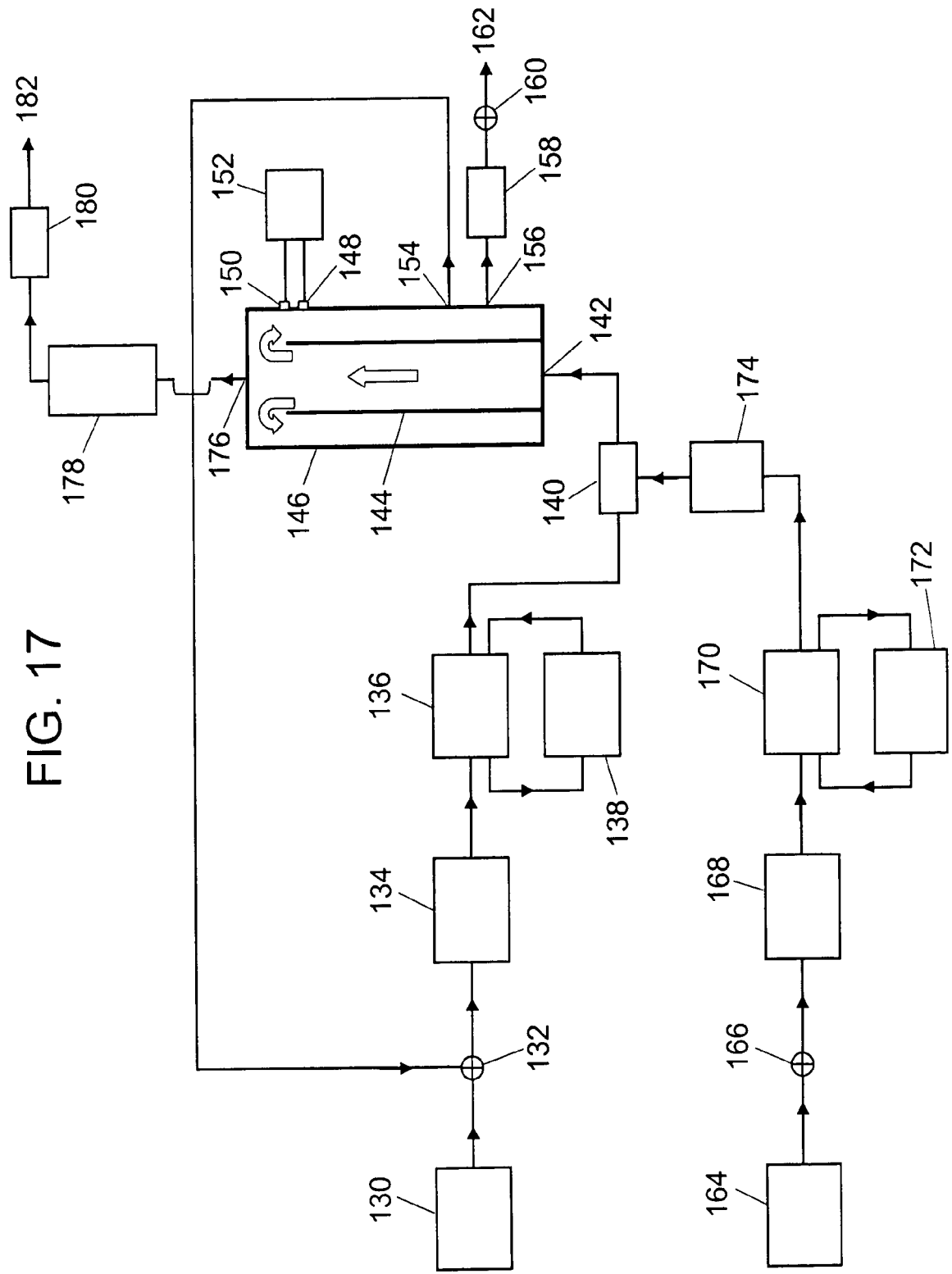
FIG. 17 illustrates a block diagram of a method of dissolving ozone gas into chilled water using a venturi injector and downstream bubble column to form an ozone-water solution.
Figure 18:
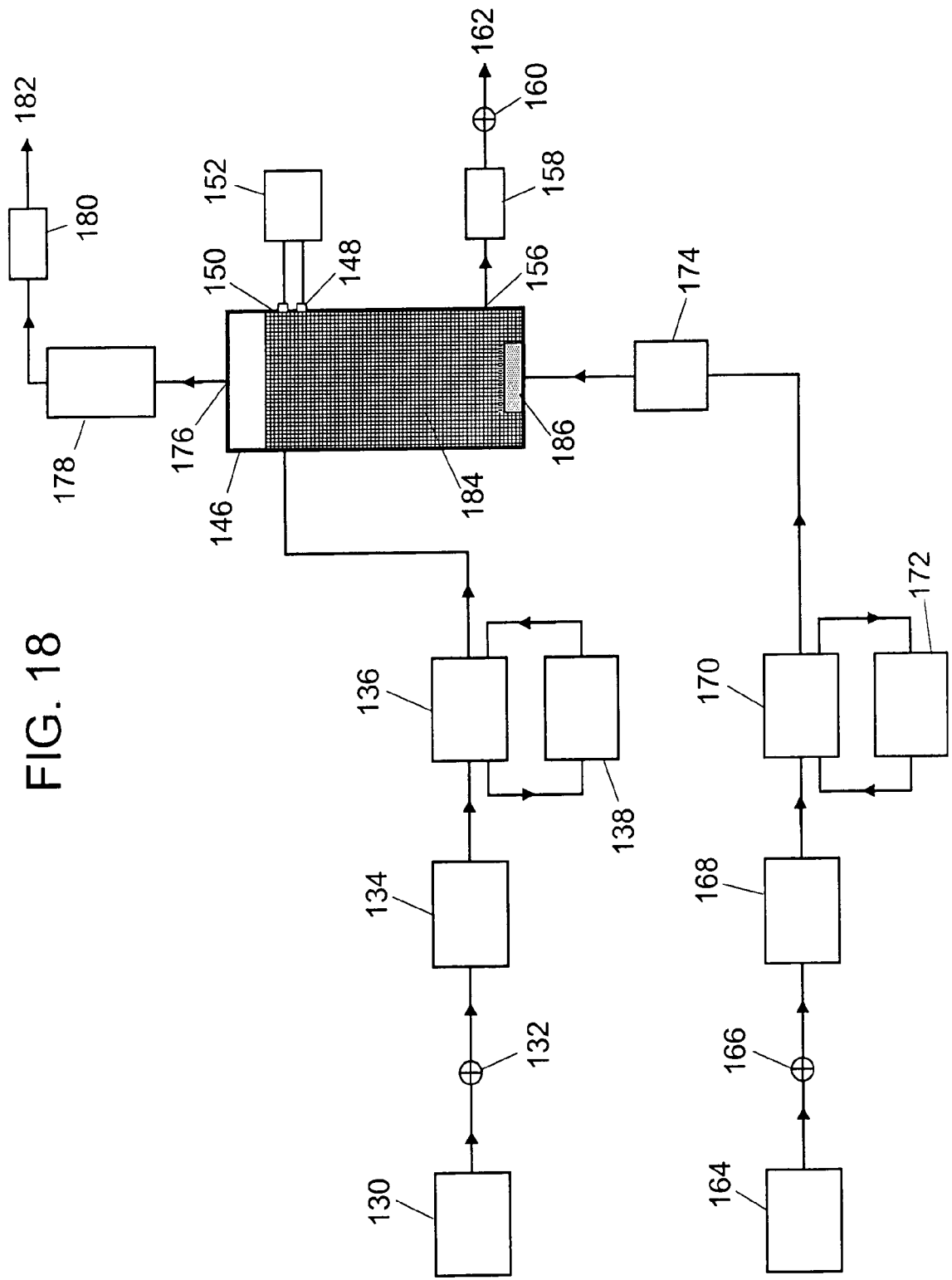
FIG. 18 illustrates a block diagram of a method of dissolving ozone gas into chilled water using a packed column to form an ozone-water solution.

$3^{nd}$ GROUP: High Performance Ozonated Water Supply for Use in Conjunction with the Preferred Embodiments (FIG. 17 through FIG. 19)

1st GROUP: Heat Applied Just Upstream of the Point of Application (FIG. 1 through FIG. 11)

A first preferred method for oxidizing materials at high speed using a solution of ozone gas dissolved in solvent comprising the steps of dissolving relatively high concentration ozone gas in solvent at a relatively low predetermined temperature T1 to form an ozone-solvent solution with a relatively high dissolved ozone concentration, and heating the ozone-solvent solution with a point-of-use heater to quickly increase the solution temperature to a predetermined higher temperature T2>T1, and applying the heated ozone-solvent solution to said material(s). The first method for oxidizing materials at high speed may additionally includes a injector/mixer for injecting and mixing additional chemicals into the ozone-solvent solution just upstream of the point of application of the ozone-solvent solution to the materials to be oxidized. A number of preferred embodiments are illustrated in FIG. 1 through FIG. 11.

Materials Processing Method W/Ozone-Solvent Solution Heated W/Heat Exchanger

Description—FIG. 1 With reference to FIG. 1, an ozonated water supply 22 is connected through a length of tubing to the common input of a three-way valve 24. The one outlet of three-way valve 24 is connected through a length of tubing to the cold process fluid inlet of a heat exchanger 28. The other outlet of three-way valve 24 is connected through a length of tubing to the facility drain-reclaim inlet 26 for the ozone-water solution. The heated working fluid outlet of a recirculating heating unit 30 is connected through a length of tubing to the heated working fluid inlet of heat exchanger 28. The heated working fluid outlet of heat exchanger 28 is connected through a length of tubing to the working fluid return of recirculating heating unit 30. The heated process fluid outlet of heat exchanger 28 is connected through a short length of tubing to a three-way valve 32. The one outlet of three-way valve 32 is connected through a short length of tubing to a dispense nozzle 36. The dispense nozzle 36 is spaced a relatively short distance from the surface 38 of the material to be oxidized, cleaned, or processed. The other outlet of three-way valve 32 is connected through a length of tubing to the facility drain-reclaim inlet 34 for the heated ozone-water solution.

Operation—FIG. 1

With reference to FIG. 1, an ozone-gas-water solution of predetermined dissolved ozone concentration is produced by the ozonated water supply 22 by dissolving ozone gas at predetermined concentration and pressure P1 into water at a predetermined temperature T1. The ozone gas is dissolved into water using a venturi injector and downstream bubble column, a packed column, a gas permeable membrane contactor, a bubble diffuser, a turbine mixer, a spray contactor, or other means known to those skilled in the art. The ozone gas may be dissolved at atmospheric pressure (~1 bar) or at elevated pressures above atmospheric pressure. The maximum dissolved concentration that can be produced for a given gas phase concentration, gas pressure, and water temperature is predicted by Henry's law as discussed in the introduction. (See Table 1).

Some ozone generators such as the ASTEX® AX8100 and AX 8200 require high purity oxygen gas mixed with approximately 0.5% nitrogen gas by volume to produce relatively high concentration ozone gas (200 to 250 grams/Nm3). Other generators such as the ASTEX® Model AX8401, ASTEX® Model AX8402, SEMOZON® Model 030.2, and SEMOZON® Model 090.2 require a source of high purity oxygen with only about 50 ppm of nitrogen by volume to produce relatively high concentration ozone gas. A generator requiring oxygen mixed with approximately 0.5% nitrogen produces ozone (O3) and a relatively large amount of NO2. When this gas stream is dissolved in water in the ozone-water contactor, the NO2 combines with water (H2O) to form nitric acid (HNO3). If the water is unbuffered, then nitric acid can cause the pH of the ozone-water solution to gradually fall. In the preferred electronic device cleaning/processing embodiment, the use of an ozone generator requiring oxygen mixed with approximately 50 ppm nitrogen is preferred because this type of generator produces ozone (O3) and a very small amount of NO2. Accordingly, when this gas stream is dissolved in water in the ozone-water contactor, only a small amount of nitric acid is formed, and there is a minimal resulting pH change.

The ozonated water supply 22 may be designed to supply an ozone-gas-water solution at a predetermined concentration and flow rate on a continuous basis or on an intermittent basis. In general, the mass flow rate out of the ozone-water solution (the product of the liquid flow rate and the dissolved ozone concentration) is less than the mass flow rate of the ozone gas entering the contactor (the product of the ozone gas flow rate and the ozone gas concentration). Accordingly, some of the ozone gas will exit from the contactor vent line as a waste ozone gas stream.

An ozononated water supply may be designed to flow the water through the gas-water contactor in a single pass and deliver an ozone-gas-water solution at a predetermined value less than the saturation concentration. Alternatively, the ozonated water supply may be designed to flow the water through the gas-water contactor in multiple passes, and thereby provide a longer time for mass transfer to occur between the gas and the liquid, and deliver an ozone-gas-water solution at a predetermined value up to the saturation concentration.

It is convenient to use a three way valve 24 to direct the solution to the process for the required process cycle time, and then direct the ozone-water solution to facility waste/reclaim 26 at the end of the cycle. This is preferred to shutting off the flow for ozonated water supplies based upon a single pass design since this type of ozonated water supply 22 requires water flow the operate. This insures that the supply runs in steady state and can provide a stable supply of ozonated water at a predetermined concentration with no transients associated with stopping and starting flow through the supply contactor. The supply can employ a controller to set the flow to a very low level during the period that the valve is set to the waste-reclaim position to conserve water and ozone. If an ozonated water supply of the batch recirculating type is employed, then the three-way valve may be used to direct the flow of water back to the contactor.

If the flow through heat exchanger 28 is stopped at the end of a process cycle, then the dissolved ozone concentration in the water remaining in the exchanger will decay toward a low value and the temperature will rise to the hot working fluid temperature. It is convenient to use a three way valve 32 just upstream of the dispense nozzle 36 to direct this volume of water to facility waste/reclaim 34 immediately prior to the next process dispense cycle. This insures that the heated ozone-gas-water solution that is subsequently dispensed onto the material 38 is at the predetermined temperature and dissolved ozone concentration. At the start of an etch cycle (process cycle) valve 26 is set to direct the process flow through the point-of-use heater (heat exchanger 28) and valve 32 is set to direct the process flow to facility waste/reclaim 34 for a time greater than or equal to the residence time of the volume between three-way valve 24 and three-way valve 32. In the case of a flow rate of 50 ml/sec (3.0 L/min) and a residence volume of 100 ml, the flow is sent to facility waste/reclaim 34 for a least 2 seconds to insure that the ozone-water solution is purged from the residence volume before valve 32 is set to direct the process flow to the dispense nozzle 36. The valve 32 is placed just upstream of the dispense nozzle 36 to minimize the volume that is not purged when valve 32 is set to direct the process flow to facility waste/reclaim 34. The waste-reclaim 26 and waste-reclaim 34 may be directed to different facility waste-reclaim locations since the process stream sent to 26 is the full concentration ozone-gas-water solution supplied by the ozonated water supply 22 and the process stream sent to 34 is the heated ozone-gas-water solution in which the concentration may have fallen significantly during the time when the flow through exchanger 28 has be set to zero between the end of one process cycle and the start of the next process cycle.

The ozonated water supply 22 delivers an ozone-gas-water solution with sufficient pressure to achieve a predetermined flow rate through the dispense nozzle 36. The delivery pressure must be sufficient pressure to produce the flow through the pressure drop across the heat exchanger 28, connecting tubing, and dispense nozzle 36.

Back Pressure Regulators for an Ozonated Water Supply Using a Pressurized Contactor. If the ozononated water supply 22 is designed to dissolve ozone gas into water at a gas pressure P2 above 1 bar, then a back pressure regulator is typically placed at the ozone off-gas outlet of the ozone-gas-water contactor and ozonated water outlet of the ozone-gas-water contactor to maintain the specified gas pressure P2 inside the contactor which is higher than pressure P1 downstream of the back pressure regulators. Once the ozone-water solution passes through the back pressure regulator to a lower pressure the ozone gas will begin to leave the solution. If the transit time of the ozone-gas-water solution from the outlet of the ozone-gas-water contactor in the ozonated water supply 22 to the inlet of the heat exchanger 28 is relatively long, then the ozone gas will have a longer time available to leave the solution in transit from the back pressure regulator to the exchanger inlet. The dissolved ozone concentration at the exchanger inlet will be less than the dissolved ozone concentration at the outlet of the ozonated water supply 22 just downstream of back pressure regulator because the ozone concentration will fall toward the equilibrium concentration at the pressure downstream of the regulator. This fall in concentration can be alleviated by moving the back pressure regulator to a point just upstream of heat exchanger 28. If the back pressure regulator is moved further downstream to a point just upstream of the dispense nozzle 36, then the decay in concentration caused by the P2>P1 can be reduced even further since the solution is maintained at the pressure P1 until last possible moment when the solution is dispensed onto the surface of the material 38 at a pressure P2.

Heat Exchanger: A Point-of-Use Heater for Quickly Heating the Ozone-Gas-Water Solution. The ozone-water solution flows through three-way valve 24 to the process fluid inlet of the heat exchanger 28. A heated working fluid such as water, supplied by a recirculating heating unit 30, flows through the hot working fluid side of the heat exchanger. The recirculating heating unit 30 is sized to provide the power required to increase the ozone water solution temperature at a specified ozone water solution flow rate. The temperature hot working fluid (typically water) that flows from the recirculating heating unit 30, through the exchanger 28, and back to the recirculating heating unit 30 for reheating is controlled by the temperature controller of the recirculating heating unit. The temperature of the ozone water solution exiting from the exchanger can be changed by changing the temperature setpoint on the recirculating heating unit. In passing through the heat exchanger, the ozone-water solution is quickly heated to a higher temperature and then immediately applied to the material to be oxidized.

The volume of the fluid passages through which the heated, supersaturated, ozone-water solution must pass, starting at the inlet of the heat exchanger 28 and ending at the dispense nozzle 36 must be kept relatively small. A typical value for this volume is 100 to 300 ml for a system designed for a dispense flow rate of approximately 3.0 l/min and a dispense temperature of approximately 50 degree C. This corresponds to a residence time of 2 seconds to 6 seconds. In addition, the volume of the fluid stream starting at the dispense nozzle 36 and ending at the surface of the material to be oxidized 38 must be kept small. A typical value for this volume is 5 to 10 ml for a system designed for a dispense flow rate of approximately 3.0 l/min and a dispense temperature of approximately 50 degree C. This corresponds to a residence time of 0.1 seconds to 0.2 seconds. A minimum total residence time, the time delay between heating the solution and applying the solution to the surface(s) to be cleaned or oxidized, minimizes the time available for the dissolved ozone concentration to fall once the solution temperature is increased.

The ozone gas will come out of solution at a higher rate and the dissolved ozone concentration will fall at a higher rate if the ozone-water solution is heated to a higher temperature. The optimum temperature for maximizing the etch rate is determined by the mass transport coefficient M as discussed earlier. Once S>>M at sufficiently high temperature, further increases in temperature do not increase etch rate further. One design approach is then to design the point-of-use heater to have a sufficiently small residence time at that etch rate maximizing temperature that the dissolved ozone concentration decays a relatively small amount.

The ozone gas will come out of solution at a higher rate and the dissolved ozone concentration will fall at a higher rate if the inside surface of the point-of-use heater (the process side of the heat exchanger in this embodiment) has scratches, since the ozone will leave solution most readily at the location of the scratches. Accordingly, a relatively smooth inner surface is desired. The inside surface of the 316 stainless steel tube-in-tube heat exchanger model 413 made by EXERGY® Inc. has a surface roughness of 20 Ra. Electropolished versions are available with a surface roughness of 5 Ra.

The ozone gas will come out of solution at a higher rate and the dissolved ozone concentration will fall at a higher rate if the surface area of the free stream(s) of fluid passing from the dispense nozzle(s) to the surface 36 is larger. If the flow of the solution from the dispense nozzle to the surface of the material to be oxidized 38 is carried by many small diameter streams, then the rate of loss of ozone gas from solution will higher when compared to the case of the solution being carried by a single solid stream because the surface area of the many small diameter streams is larger.

In applications such as wafer processing the use of stainless steel wetted components is not acceptable because these materials introduce metal contamination into the process chemistry. In these applications the preferred materials for all wetted parts are metal free materials such as TEFLON® PFA or Teflon PTFE or quartz. Accordingly, the point-of-use heater should employ materials such as TEFLON® PFA or Teflon PTFE for all wetted surfaces in lieu of stainless steel for these applications.

In the prior art, the ozone is dissolved in water at a given temperature T1 and the ozone-water solution is applied to the material to be oxidized at a temperature T2=T1. Accordingly, if one lowers the temperature T1 to increase the dissolved ozone concentration, then one decreases the surface reaction rate S. Alternatively, if one increases the temperature T2 to increase the surface reaction rate, then one decreases the dissolved ozone concentration.

The present invention overcomes this limitation by tricking mother nature into providing a higher dissolved concentration at the elevated temperature that could be achieved under equilibrium conditions.

A first type of method for treating materials at high speed using a solution of ozone gas dissolved in a solvent comprises the steps of dissolving relatively high concentration ozone gas in water at a relatively low predetermined temperature T1 to form an ozone-water solution with a relatively high dissolved ozone concentration, and heating the ozone-water solution with a point-of-use heater to quickly increase the solution temperature to a predetermined higher temperature T2>T1, where preferrably T2−T1>5 degree C., and applying the heated ozone-water solution to said material(s).

A second type of method for oxidizing materials at high speed using a solution of ozone gas dissolved in solvent comprises the steps of dissolving (relatively high concentration) ozone gas in water at a relatively low predetermined temperature T1 to form an ozone-water solution (with a relatively high dissolved ozone concentration), applying the cold ozone-water solution to said materials while heating said materials and said ozone-water solution at the point of application to quickly increase said material temperature and said solution temperature to a predetermined higher temperature T2>T1, where preferrably T2−T1>5 degree C.

The heated ozone-water solution will have a much higher dissolved ozone concentration at said higher temperature than could be achieved if the ozone gas was initially dissolved in water at said higher temperature. The parameter space for the preferred embodiments and prior art is shown in Table 2 below. In the prior art, the ozone is dissolved and applied at the same temperature.

TABLE 2

Parameter Space of the Preferred Embodiments and Prior Art (the ozone-water solution is prepared by dissolving ozone gas in water at a temperature T1; the ozone-water solution is applied to the material to be oxidized at a temperature T2

| | |
|---|---|
| T2 > T1 | Preferred Embodiments |
| T2 = T1 | PRIOR ART |

TABLE 2-continued

Parameter Space of the Preferred Embodiments and Prior Art (the ozone-water solution is prepared by dissolving ozone gas in water at a temperature T1; the ozone-water solution is applied to the material to be oxidized at a temperature T2

| | |
|---|---|
| T2 < T1 | generally lower performance than T2 = T1 (Note 1) |

Note 1: In the case with T2 < T1 the dissolved concentration is nominally the same as when T2 = T1 and the surface reaction rate S is lower because the surface temperature is lower.

Note 1: In the case with T2<T1 the dissolved concentration is nominally the same as when T2=T1 and the surface reaction rate S is lower because the surface temperature is lower.

The point-of-use heater is designed to have a small residence volume so that the residence time between the inlet of the heater and the point of application is small and there is insufficient time for supersaturated solution to return to equilibrium before reaching the surface of the material to be oxidized. The time required for the solution to return to equilibrium is dependent upon the temperature to which to solution is heated. Our preliminary measurements indicate that at a temperature of about 50 degree C., a residence time of 2 seconds will allow the dissolved concentration to only fall by about 10 to 20 percent. At higher temperatures, the required residence time is smaller. The residence time is proportional to the volume and inversely proportional to the dispense flow rate though that volume.

We prepared an ozone-water solution by dissolving ozone gas, at concentration of 240 g/Nm3, a flow rate of 0.48 L/min, and a pressure of 1 bar, into water at a temperature of about 8 degree C. using a Mazzei Model 287 venturi injector and bubble column contactor operated in the recirculating mode. We waited about 30 minutes and allowed the dissolved concentration reach the saturation concentration at about 70. We drew the ozone-water solution from the unpressurized contactor with a high pressure gear pump capable of delivering a flow rate of 2.7 L/minute at 80 psi. We passed the solution through an Exergy tube in tube heat exchanger model 413, through a UV absorption type dissolved ozone monitor and thermocouple probe, and then to a waste collection carboy. We measured the dissolved concentration upstream and downstream of the heater as a function of the temperature of the ozone-water solution downstream of the heater for several different temperatures. We used this data to estimate the decay time constant as function of temperature by assuming that the decay time was an exponential function of the temperature. We ran a similar test using coil in heated water bath heater. We flowed the water through a 20 foot long coil of stainless steel, 0.375 inch OD, 0.305 inch ID tubing, immersed in a heated water bath. Since the water bath did not have sufficient power to maintain a constant bath temperature, the dispense temperature of the ozone water solution decreased about 5 degree C. during the test. Accordingly, we used average temperatures in analyzing the results. The residence volume of the coil in bath heater was about 270 ml and the residence volume of the tube in tube heat exchanger was about 90 ml. (see the table 3 footnotes) The results for both tests were consistent with the model presented below. The results for one test series are presented in Table 3 below.

TABLE 3

Decay time constant as a function of temperature: Measured decay time constant as function of temperature and calculated decay time constant as function of temperature assuming that the decay time is an exponential function of the temperature $$Tau = 2E - 10*Exp(8.26(1000/T))$$

| Temp deg. C. | Temp deg. K | 1000/T (K) | measured decay const. Tau secs | calculated decay const. Tau secs | transit time t secs note 1 | decay factor exp(-t/Tau) | transit time t secs note 2 | decay factor exp(-t/Tau) | transit time t secs note 3 | decay factor exp(-t/Tau) |
|---|---|---|---|---|---|---|---|---|---|---|
| 20 | 293 | 3.41 |  | 292.3 | 2 | 99% | 6 | 98% | 22 | 93% |
| 25 | 298 | 3.36 |  | 186.6 | 2 | 99% | 6 | 97% | 22 | 89% |
| 30 | 303 | 3.30 |  | 120.9 | 2 | 98% | 6 | 95% | 22 | 83% |
| 35 | 308 | 3.25 |  | 79.4 | 2 | 98% | 6 | 93% | 22 | 76% |
| 40 | 313 | 3.19 |  | 52.9 | 2 | 96% | 6 | 89% | 22 | 66% |
| 45 | 318 | 3.14 |  | 35.7 | 2 | 95% | 6 | 85% | 22 | 54% |
| 50 | 323 | 3.10 |  | 24.3 | 2 | 92% | 6 | 78% | 22 | 41% |
| 55 | 328 | 3.05 |  | 16.8 | 2 | 89% | 6 | 70% | 22 | 27% |
| 60 | 333 | 3.00 | 11.00 | 11.7 | 2 | 84% | 6 | 60% | 22 | 15% |
| 65 | 338 | 2.96 | 8.4 | 8.3 | 2 | 79% | 6 | 49% | 22 | 7% |
| 70 | 343 | 2.92 |  | 5.9 | 2 | 71% | 6 | 36% | 22 | 2% |
| 75 | 348 | 2.87 | 4.05 | 4.3 | 2 | 63% | 6 | 24% | 22 | 1% |
| 80 | 353 | 2.83 |  | 3.1 | 2 | 52% | 6 | 14% | 22 | 0% |
| 85 | 358 | 2.79 |  | 2.3 | 2 | 41% | 6 | 7% | 22 | 0% |
| 90 | 363 | 2.75 |  | 1.7 | 2 | 30% | 6 | 3% | 22 | 0% |
| 95 | 368 | 2.72 |  | 1.3 | 2 | 20% | 6 | 1% | 22 | 0% |

Note 1: EXERGY ® Model 413 stainless steel tube-in-tube heat exchanger; total residence volume from the heater inlet to the heater outlet approximately 90 ml; dispense flow rate 45 ml/sec; residence time approximately 2 secs
Note 2: ⅜ inch OD, 20 foot long, coil in water bath heater; total residence volume from the heater inlet to the heater outlet approximately 270 ml; dispense flow rate approx. 45 ml/sec; residence time approximately 6 secs
Note 3: relatively large volume heater or heat exchanger; total residence volume from the heater inlet to the heater outlet chosen to be 1000 ml; dispense flow rate approx. 45 ml/sec; residence time approximately 22 secs From this data we can see that higher temperatures cause the concentration to fall more quickly. If one is to minimize the drop in concentration upon heating, then the residence time must be decreased if the temperature is increased. For example, if we would like the dissolved ozone concentration at the outlet of the point-of-use heater to be no less than 80 percent of the dissolved ozone concentration at the inlet of the point-of-use heater, then the transit time must be less than or equal to the values estimated in Table 4 below.

Table 4. Maximum estimated permissible ozone-water solution heating time (heater transit time): Example calculated for the dissolved ozone concentration at the heater outlet to be no less than 80 percent of the dissolved ozone concentration at the heater inlet. Estimated from decay data measured with an inlet dissolved ozone concentration of about 100 mg/liter, an initial upstream ozone-water solution temperature of about 8 deg. C. and the a final specified downstream ozone-water solution temperature ranging from 20 deg. C. to 95 deg. C.

TABLE 4

| Example Decay Factor = 80% (Downstream Conc./Upstream Conc.) | | | | Calculated maximum |
|---|---|---|---|---|
| Ave solution temp. at heater outlet Temp deg. C. | Temp. deg. K | 1000/T (K) | Estimated decay const. Tau secs | allowable heater transit time t = − Tau*Ln (decay factor) secs |
| 20 | 293 | 3.41 | 292.3 | 65.22 |
| 25 | 298 | 3.36 | 186.6 | 41.63 |
| 30 | 303 | 3.30 | 120.9 | 26.97 |

TABLE 4-continued

| Example Decay Factor = 80% (Downstream Conc./Upstream Conc.) | | | | Calculated maximum |
|---|---|---|---|---|
| Ave solution temp. at heater outlet Temp deg. C. | Temp. deg. K | 1000/T (K) | Estimated decay const. Tau secs | allowable heater transit time t = − Tau*Ln (decay factor) secs |
| 35 | 308 | 3.25 | 79.4 | 17.72 |
| 40 | 313 | 3.19 | 52.9 | 11.80 |
| 45 | 318 | 3.14 | 35.7 | 7.96 |
| 50 | 323 | 3.10 | 24.3 | 5.43 |
| 55 | 328 | 3.05 | 16.8 | 3.75 |
| 60 | 333 | 3.00 | 11.7 | 2.62 |
| 65 | 338 | 2.96 | 8.3 | 1.85 |
| 70 | 343 | 2.92 | 5.9 | 1.32 |
| 75 | 348 | 2.87 | 4.3 | 0.95 |
| 80 | 353 | 2.83 | 3.1 | 0.69 |
| 85 | 358 | 2.79 | 2.3 | 0.51 |
| 90 | 363 | 2.75 | 1.7 | 0.37 |
| 95 | 368 | 2.72 | 1.3 | 0.28 |

We know from our model that an increased temperature will provide a significant increase in etch rate until the etch rate becomes mass transport limited. Our measurements show that with a wafer spinning at about 4,000 rpm and a dispense flow rate of 2.7 L/min, that the etch rate becomes mass transport limited at the wafer edge at about 50 degree C. Other methods of applying the solution to the material to be oxidized may provide a higher or lower mass transport coefficient and a correspondingly higher or lower optimum temperature.

Heating Power Requirement. The power input in watts required to increase the temperature of a stream of water can be calculated given the water flow rate, the desired temperature rise, and the heat capacity of the water. We have shown the results of that calculation in Table 5 below. If the flow rate of the ozone-water solution which passes through the point-of-use heater is 2.7 L/min, and the water enters at a temperature of 5 degree C., and the desired exit temperature is 55 deg. C., then the heater must transfer energy to the ozone-water stream at a power level of 9.3 kW.

TABLE 5

Point-of-use Heater Power Requirement

| Dispense Flow Rate (L/min) | Inlet Water Temp. (deg. C.) | Desired Outlet Water Temp. (deg. C.) | Required Temp. Increase (deg. C.) | Power Req'd (kW) |
| --- | --- | --- | --- | --- |
| 2.7 | 5 | 45 | 40 | 7.45 |
| 2.7 | 5 | 55 | 50 | 9.3 |
| 2.7 | 5 | 65 | 60 | 11.2 |
| 2.7 | 5 | 75 | 70 | 13.0 |
| 2.7 | 5 | 85 | 80 | 14.9 |
| 2.7 | 5 | 95 | 90 | 16.8 |
| 3.3 | 5 | 45 | 40 | 9.1 |
| 3.3 | 5 | 55 | 50 | 11.4 |
| 3.3 | 5 | 65 | 60 | 13.7 |
| 3.3 | 5 | 75 | 70 | 15.9 |
| 3.3 | 5 | 85 | 80 | 18.2 |
| 3.3 | 5 | 95 | 90 | 20.5 |

The power required to increase the ozone gas-water solution temperature can be transferred from a heated working fluid in a heat exchanger. The energy transferred by a particular heat exchanger is determined by the temperature and flow rate of hot working fluid entering the working fluid side of the exchanger, the temperature and flow rate of the ozone gas-water solution entering the process side of the exchanger, and the desired temperature of the ozone-water solution exiting from the exchanger. Example flow rates and temperatures are shown in Table 6 below. We can see that for a given flow rate and temperature for the ozone-water solution entering the heat exchanger and a given flow rate for the heated working fluid circulated through the outer tube of the heat exchanger by the recirculating heating unit, that changing the temperature of the working fluid will change the temperature of the ozone-water solution exiting from the exchanger to the dispense nozzle. The embodiment can provide a constant dispense temperature T2 the other parameters mentioned are held constant.

TABLE 6

Calculated Performance of EXERGY ® Model 413 Stainless Steel Tube-in-Tube Heat Exchanger Reported by the Manufacturer. The ozone-gas-water solution is passed through the 0.180 inch ID, .250 inch OD, 240 inch long, inner tube. The heated working fluid from the recirculating heating unit is passed through the annular space bounded by a concentric .430 inch ID outer tube and the inner tube. The internal volume of the inner tube is 90 ml.

| | Example 1: 48° C. Dispense Temperature | | Example 2: 56° C. Dispense Temperature | |
| --- | --- | --- | --- | --- |
| Fluid Used for the Calculation | Inner Tube ozone-water solution water | Outer Tube heated working fluid water | Inner Tube ozone-water solution water | Outer Tube heated working fluid water |
| Temp In (° C.) | 7 | 60 | 7 | 70 |
| Temp. Out (° C.) | 48 | 38 | 56 | 43 |
| Vol. Flow (L/min) | 2.7 | 5 | 2.7 | 5 |

TABLE 6-continued

Calculated Performance of EXERGY ® Model 413 Stainless Steel Tube-in-Tube Heat Exchanger Reported by the Manufacturer. The ozone-gas-water solution is passed through the 0.180 inch ID, .250 inch OD, 240 inch long, inner tube. The heated working fluid from the recirculating heating unit is passed through the annular space bounded by a concentric .430 inch ID outer tube and the inner tube. The internal volume of the inner tube is 90 ml.

| | Example 1: 48° C. Dispense Temperature | | Example 2: 56° C. Dispense Temperature | |
| --- | --- | --- | --- | --- |
| Fluid Used for the Calculation | Inner Tube ozone-water solution water | Outer Tube heated working fluid water | Inner Tube ozone-water solution water | Outer Tube heated working fluid water |
| Pressure Drop (psi) | 24 | 6 | 24 | 6 |
| Heat Transfer (watts) | 7616 | 7616 | 9203 | 9203 |

Figure 2:
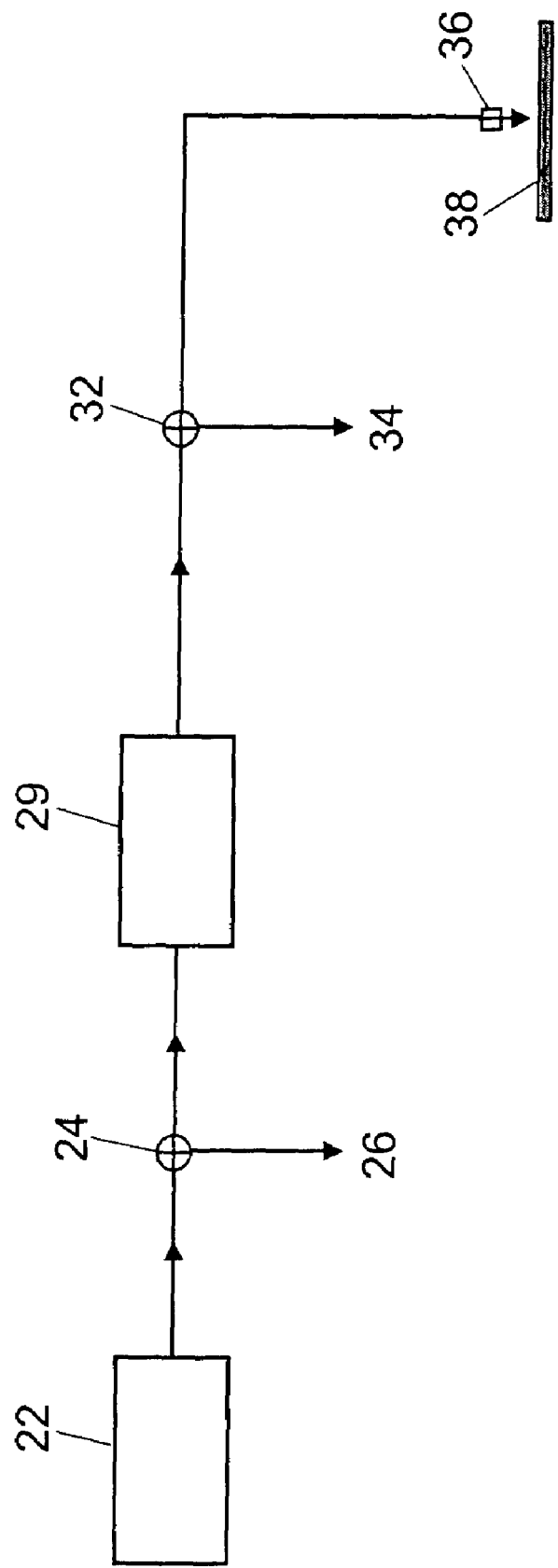
FIG. 2 illustrates a functional block diagram of a method of processing materials: A cold ozone-water solution at temperature T1 is heated to temperature T2>T1 using a point-of-use heater just upstream of the point of application of the ozone-water solution to the material to be processed.

Materials Processing Method W/Ozone-Water Solution Heated W/A Point-of-Use Water Heater Description—FIG. 2

With reference to FIG. 2, an ozonated water supply 22 is connected through a length of tubing to the common input of a three-way valve 24. The one outlet of three-way valve 24 is connected through a length of tubing to the cold process fluid inlet of point-of-use heater 29. The other outlet of three-way valve 24 is connected through a length of tubing to the facility drain-reclaim 26 for the ozone-water solution. The heated process fluid outlet of point-of-use heater 29 is connected through a short length of tubing to a three-way valve 32. The one outlet of three-way valve 32 is connected through a short length of tubing to a dispense nozzle 36. The dispense nozzle 36 is spaced a relatively short distance from the surface 38 of the material to be oxidized, cleaned, or processed. The other outlet of three-way valve 32 is connected through a length of tubing to the facility drain-reclaim 34 for the heated ozone-water solution.

Operation—FIG. 2

Point-of-Use Heater: A Point-of-Use Heater for Quickly Heating the Ozone-Gas-Water Solution: The point-of-use heater 29 has the same requirements as the heat exchanger including those relating to internal volume, surface roughness, and materials of metal free materials of construction. Most commercially available heaters of the required power level and materials of construction such as those made for point-of-use heating of DI water for the semiconductor and pharmaceutical industry have an internal volume of at least 2000 ml. One embodiment for a point-of-use heater with small internal volume is constructed using radiant and convention heating of the ozone-water solution. The ozone-water solution is flowed through quartz tubing that surrounds the IR heating source. The volume of the tubing can be made small to minimize the residence time inside the heater. A temperature sensor, either at the outlet of the heater, or just upstream of the dispense nozzle, is connected to temperature controller. The temperature controller increases or decreases the amount of power delivered by the heater to achieve and maintain a specified dispense temperature. A direct heater with feedback control from the dispense temperature can typically adjust the temperature at the dispense point more quickly than can a heat exchanger embodiment.

Heating Power Requirement: The heating power requirement using a point-of-use heater 29 is the same as that using a heat exchanger 28.

Materials Processing Method Additionally Including Point-Of-Use Chemical Injection—Single Chemical Supply—

Figure 3:
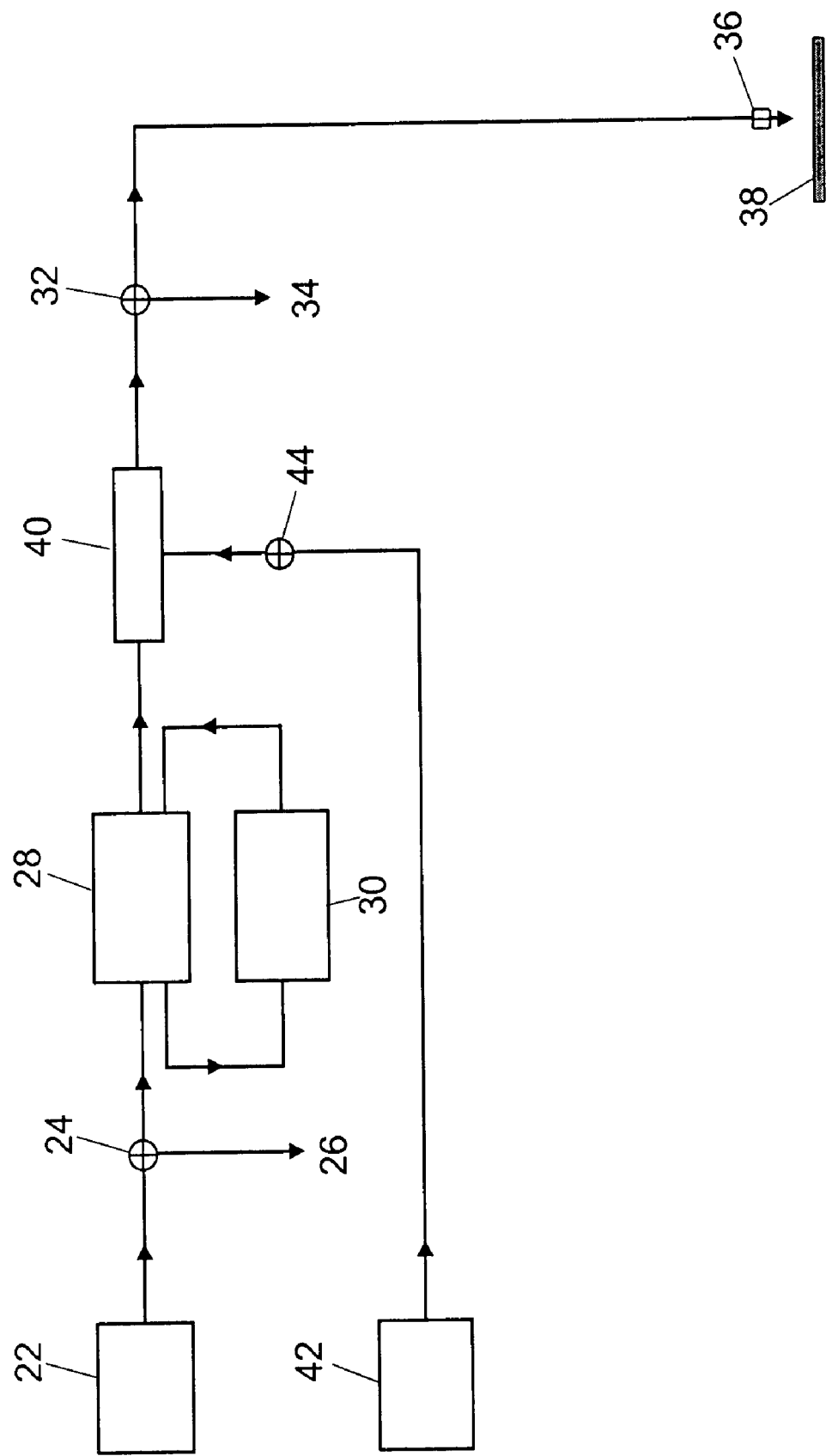
FIG. 3 illustrates a functional block diagram of a method of processing materials in which additional chemicals are injected into the ozone-water solution just upstream of the point of application.

Description—FIG. 3

It is often useful to have a means to mix additional chemicals with the ozone-gas-water solution prior to applying the solution to the material to be oxidized.

With reference to FIG. 3, an ozonated water supply 22 is connected through a length of tubing to the common input of a three-way valve 24. The one outlet of three-way valve 24 is connected through a length of tubing to the cold process fluid inlet of a heat exchanger 28. The other outlet of three-way valve 24 is connected through a length of tubing to the facility drain-reclaim 26 for the ozone-water solution. The heated working fluid outlet of a recirculating heating unit 30 is connected through a length of tubing to the heated working fluid inlet of heat exchanger 28. The heated working fluid outlet of heat exchanger 28 is connected through a length of tubing to the working fluid return of recirculating heating unit 30. The heated process fluid outlet of heat exchanger 28 is connected through a short length of tubing to the inlet of chemical injector/mixer 40. The outlet of an injected chemical supply 42 is connected to the inlet of two-way valve 44. The outlet of valve 44 is connected to the chemical injection port of chemical injector/mixer 40. The outlet of chemical injector/mixer 40 is connected to the common inlet port of three-way valve 32. The one outlet of three-way valve 32 is connected through a short length of tubing to a dispense nozzle 36. The dispense nozzle 36 is spaced a relatively short distance from the surface 38 of the material to be oxidized, cleaned, or processed. The other outlet of three-way valve 32 is connected through a length of tubing to the facility drain-reclaim 34 for the heated ozone-water solution.

Operation—FIG. 3

Injected Chemical Supply System—Single Chemical Reservoir: The injected chemical supply provides a chemical at a predetermined delivery pressure and a predetermined flow rate into the injection port of the injector/mixer 40 where the concentration of the chemical dispensed by the supply and ratio of the flow rate of the injected chemical to the flow rate of the ozone-gas-water solution through the injector/mixer determines the concentration of the injected chemical in the solution exiting from the mixer. The supply 42 may be implement with a source of pressurized nitrogen regulated to a predetermined pressure (not shown) connected through a length of tubing to a reservoir (not shown) containing a liquid chemical to be injected. The dip-tube outlet (not shown) of the chemical reservoir is connected through a length of tubing to the inlet side a flow controlling needle valve (not shown). The outlet of the flow controlling needle valve is connected through a length of tubing to the inlet of a flow meter. The outlet of the flow meter is connected through a length of tubing to the inlet of the chemical injection control valve 44. The outlet of the chemical injection control valve 44 is connected through a length of tubing to the chemical injection port of chemical injector/mixer 40. The pressurized injected chemical supply can also be implemented using a metering pump of other means known to those skilled in the art.

Point-of-use Chemical Injector: The chemical injector/mixer 40 may be a venturi injector, a static mixer, a mixing "T", or other device known to those skilled in the art. The injected chemical supply must deliver the chemical to the injection port of chemical injector/mixer with sufficient pressure to achieve the desired predetermined injected chemical flow rate. The internal volume of the injector mixer 40 must be kept to minimize the additional volume between the heat exchanger 28 and the dispense nozzle 36 referred to in the earlier discussion.

Minimizing temperature or Dissolved Ozone Concentration Changes Caused by the Injection of Chemicals: In the preferred embodiment the chemical injector/mixer 40 is located downstream of the heat exchanger 28. The temperature of the ozone-water solution is set at a predetermined temperature which is in the range of 30 to 95 deg. C. In the electronic device cleaning and processing embodiment the temperature may be approximately 50 deg. C. If the temperature of the injected chemical is below the temperature of the ozone-water solution entering the injector, then the solution exiting from the heater will be below the temperature of the solution entering the point-of-use heater. The fall in temperature may be mitigated by minimizing the volume flow rate of the injected chemical relative to the volume flow rate of the ozone-water solution. In an alternative embodiment, the injected chemicals can be preheated to approximately the same temperature as the temperature of the ozone-water solution entering the chemical inject thereby eliminating any fall in temperature mentioned above.

It is well known that by the introduction of hydroxyl radical scavengers (carbonates, bicarbonates, phosphates, etc) into an ozone-water solution at a molar concentration of 5 to 10 times the molar concentration of the ozone, that the concentration of the molecular ozone in solution can be maintained. We have found that borates can also be used to stabilize the concentration and adjust the pH. In some applications such as medical instrument sterilization, where metal ion contamination is not a concern, one can use a large range of hydroxyl radical scavenger chemicals such a sodium phosphate, potassium phosphate, sodium carbonate. In the case of electronic device processing, one can use ammonium counter ions in lieu of the metal counter ions. However, many candidate hydroxyl radical scavenger chemicals such ammonium carbonate, ammonium bicarbonate, ammonium phosphate, ammonium acetate, carboxylic acid, phosphonic acid, and salts thereof, as well as sulfates, for example ammonium sulfate, if given sufficient time, may react with ozone-water solution, oxidize the injected chemical, consume ozone, and thereby significantly reduce the dissolved ozone concentration. The advantage of injecting these chemicals near the point-of-use is that the time available for these reactions to proceed very far is severely reduced. Accordingly, many chemicals which would not normally be useable if mixed in a heated ozone-water solution and given time to react can be employed by injecting the chemicals into the ozone-water solution stream just upstream of the point-of-use.

In the semiconductor wafer processing application a chemical may be injected at approximately 20–25 deg. C., at a flow rate of approximately 1 ml/sec into an ozone-water solution flowing at approximately 50 ml/sec. We found it useful to add approximately 1 ml of 1.0 mole/liter solution of a hydroxyl radical scavenger such as ammonium bicarbonate for every 50 ml of a dispensed 72 mg/Liter ozone-water solution (50:1 dilution of the injected mixture), thereby forming a mixture of ozone-water solution with a dissolved ozone concentration of about 72 mg/Liter (1.5 millimoles/liter) and a hydroxyl radical scavenger concentration of about 20 millimoles/liter. Other alternative hydroxyl radical scavenger chemicals well known to those skilled in the art such as ammonium carbonate, ammonium acetate, and acetic acid can also produce good results.

The pH of the ozone-water solution has a number important effects. First, the pH can influence metal corrosion rates. Generally, the optimum pH for minimizing metal corrosion is slightly less than 7. Second, the pH can influence of etch rate. For example, the inventors have shown that normalized etch rate of SHIPLEY® UV-6 DUV positive photoresist at pH=4.2 is about $1/10^{th}$ the etch rate at PH=6.7. Many metal free pH adjusting chemicals suitable for electronic device manufacturing (ammonium hydroxide, ammonium phosphate monobasic, ammonium phosphate dibasic), if given sufficient time, may react with ozone-water solution, oxidize the injected chemical, consume ozone, and thereby significantly reduce the dissolved ozone. Point-of-use injection of these chemicals can significantly reduce the amount of consumption of both ozone and the chemical.

Metal corrosion control is a challenge in many aqueous cleaning systems. Corrosion inhibitors such as benzotriazoles, tolytriaxoles, mercaptobenzathiozol, axoles, imidazoles, thioxoles, indoles, pyrazoles, benzoate, molybdates, phosphates, chromates, dichromates, tungstate, silicates, vandate, and borate may be introduced into the water-ozone solution to control metal corrosion. Benzotriazole is an attractive copper corrosion inhibitor. Corrosion inhibitor chemicals may be conveniently injected and mixed into the ozone-water solution just upstream of the point of application of the solution to the material to be cleaned or oxidized.

Surfactants are often used in aqueous cleaning systems to improve wetting of surfaces. However, most candidate surfactants react with ozone. Point-of-use injection of these chemicals can significantly reduce the amount of consumption of both ozone and the surfactant.

In the preferred embodiment the chemical injector/mixer 40 is located downstream of the heat exchanger 28. Alternatively, the chemical injector/mixer 40 could be located just upstream of the heat exchanger 28. In this case the injected chemicals are heated with the ozone-water solution. However, the chemicals have a slightly longer time available to react with the ozone-water solution.

Figure 4:
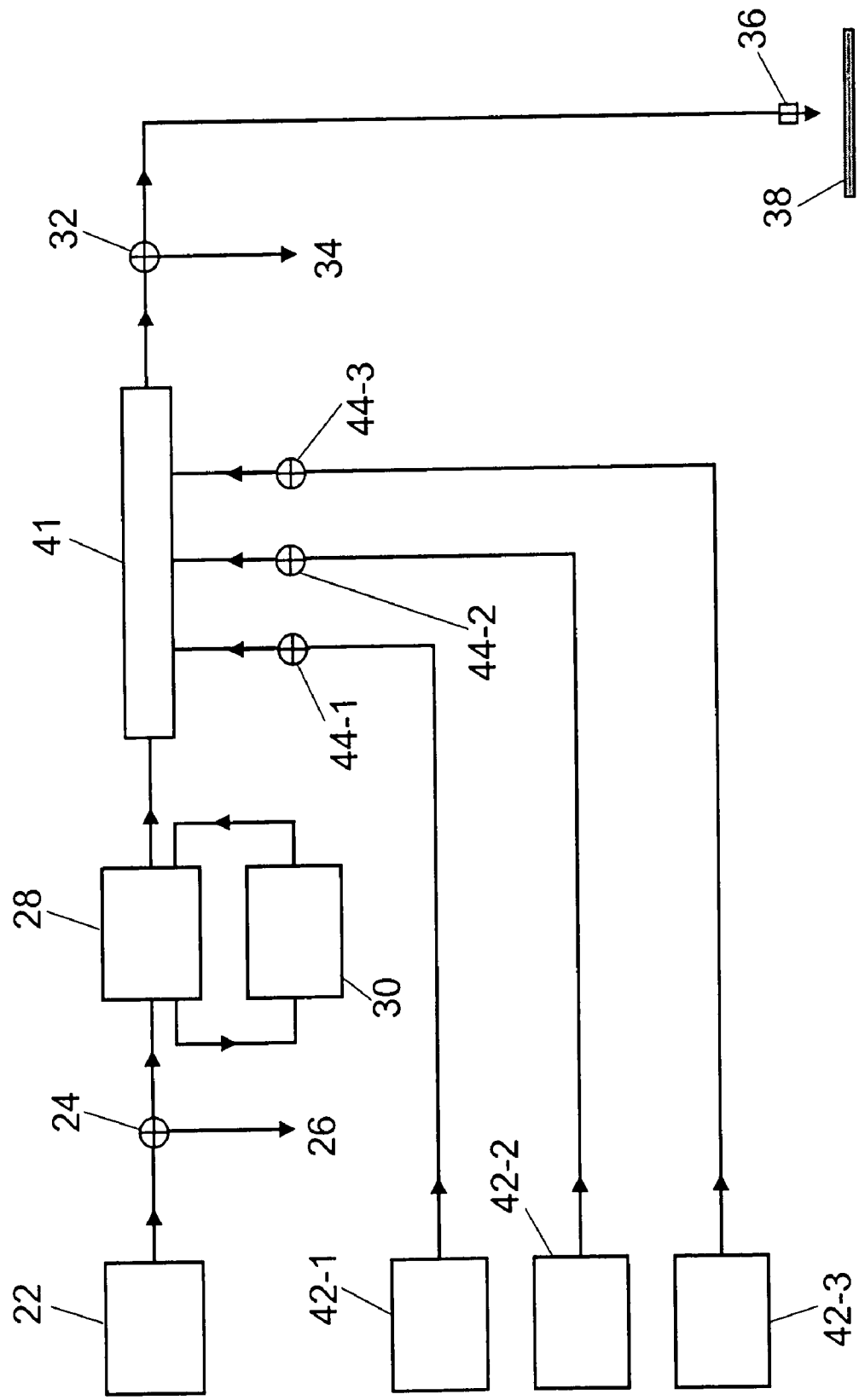
FIG. 4 illustrates a functional block diagram of a method of processing materials with multiple chemical injection supplies.

Materials Processing Method Additionally Including Point-Of-Use Chemical Injection—Multiple Chemical Supplies Description—FIG. 4

In an alternative embodiment, means may be provide for the injection of more than one chemical, each from a separate chemical reservoir. With reference to FIG. 4, an ozonated water supply 22 is connected through a length of tubing to the common input of a three-way valve 24. The one outlet of three-way valve 24 is connected through a length of tubing to the cold process fluid inlet of a heat exchanger 28. The other outlet of three-way valve 24 is connected through a length of tubing to the facility drain-reclaim 26 for the ozone-water solution. The heated working fluid outlet of a recirculating heating unit 30 is connected through a length of tubing to the heated working fluid inlet of heat exchanger 28. The heated working fluid outlet of heat exchanger 28 is connected through a length of tubing to the working fluid return of recirculating heating unit 30. The heated process fluid outlet of heat exchanger 28 is connected through a short length of tubing to the inlet of chemical injector/mixer 41. The outlet of an injected chemical supply 40-1 is connected to the inlet of two-way valve 44-1. The outlet of valve 44-1 is connected to a first chemical injection port of a multiple port chemical injector/mixer 41. The outlet of an injected chemical supply 40-2 is connected to the inlet of two-way valve 44-2. The outlet of valve 44-2 is connected to a second chemical injection port of a multiple port chemical injector/mixer 41. The outlet of an injected chemical supply 40-3 is connected to the inlet of two-way valve 44-3. The outlet of valve 44-3 is connected to a third chemical injection port of a multiple port chemical injector/mixer 41. The outlet of chemical injector/mixer 41 is connected to the common inlet port of three-way valve 32. The one outlet of three-way valve 32 is connected through a short length of tubing to a dispense nozzle 36. The dispense nozzle 36 is spaced a relatively short distance from the surface 38 of the material to be oxidized, cleaned, or processed. The other outlet of three-way valve 32 is connected through a length of tubing to the facility drain-reclaim 34 for the heated ozone-water solution. Embodiments for the injection of chemicals, either from a fewer number, or from a greater number of injected chemical supplies, can be implemented using a similar approach.

Separate Injector/Mixer Element for Each Injected Chemical. In an alternative embodiment a separate injector/mixer element for each injected chemical, may be used in lieu of a single injector/mixer element, with multiple chemical inlet ports. The design of apparatus for the injection of chemicals into a fluid stream is well known to those skilled in the art. Many alternative approaches may be chosen provided that the residence time of the ozone-water solution in the injecting mixing element(s) is small since this residence time adds to the total residence time. The short residence time from the inlet of the point-of-use heater 28 or 29 to the point of application of the ozone-water and injected chemical solution to the material to be oxidized has two important benefits. A short residence time minimizes the amount of time available for the dissolved ozone concentration of the supersaturated ozone-water solution entering the mixing element to fall much during the time required for the solution to pass through the element. A short residence time also minimizes the amount of time available for the ozone-water solution to react with the injected chemicals. If the chemicals react with the ozone-water solution, the reaction may not only consume ozone and reduce the dissolved ozone concentration, but also may consume some or all of the injected chemical.

Means for Purging Chemical Injector Lines. In an alternative embodiment, each chemical injection valve 44-1, 44-2, and 44-3 may be a four-way valve to provide for purging the injection line. In the "off" position a four-way chemical injection valve can shut off chemical injection to the injected chemical inlet. In the "on" position, the valve can permit chemical injection to the injected chemical inlet. In the "purge" position permit the purging with DI water, for example, the lengths of tubing between the valves 44-1, 44-2, and 44-3 and the chemical injector/mixer 41 to prepare for the introduction of a different chemical into the injected chemical inlet of chemical injector/mixer 41.

Operation—FIG. 4

This embodiment may provided for the injection of different chemicals a predetermined times during the materials processing cycle. The rate of injection for each of the chemicals can be specified and controlled for each instant of time during the materials processing cycle. A preferred embodiment may utilize a computer or microprocessor to control the flow rates at each time step of the process. The operation of the of the point-of-use chemical injection system with multiple chemical supplies is otherwise the same as the operation of a point-of-use chemical injection system with a single chemical supply.

Materials Processing Method with a Spin Processor

Figure 5:
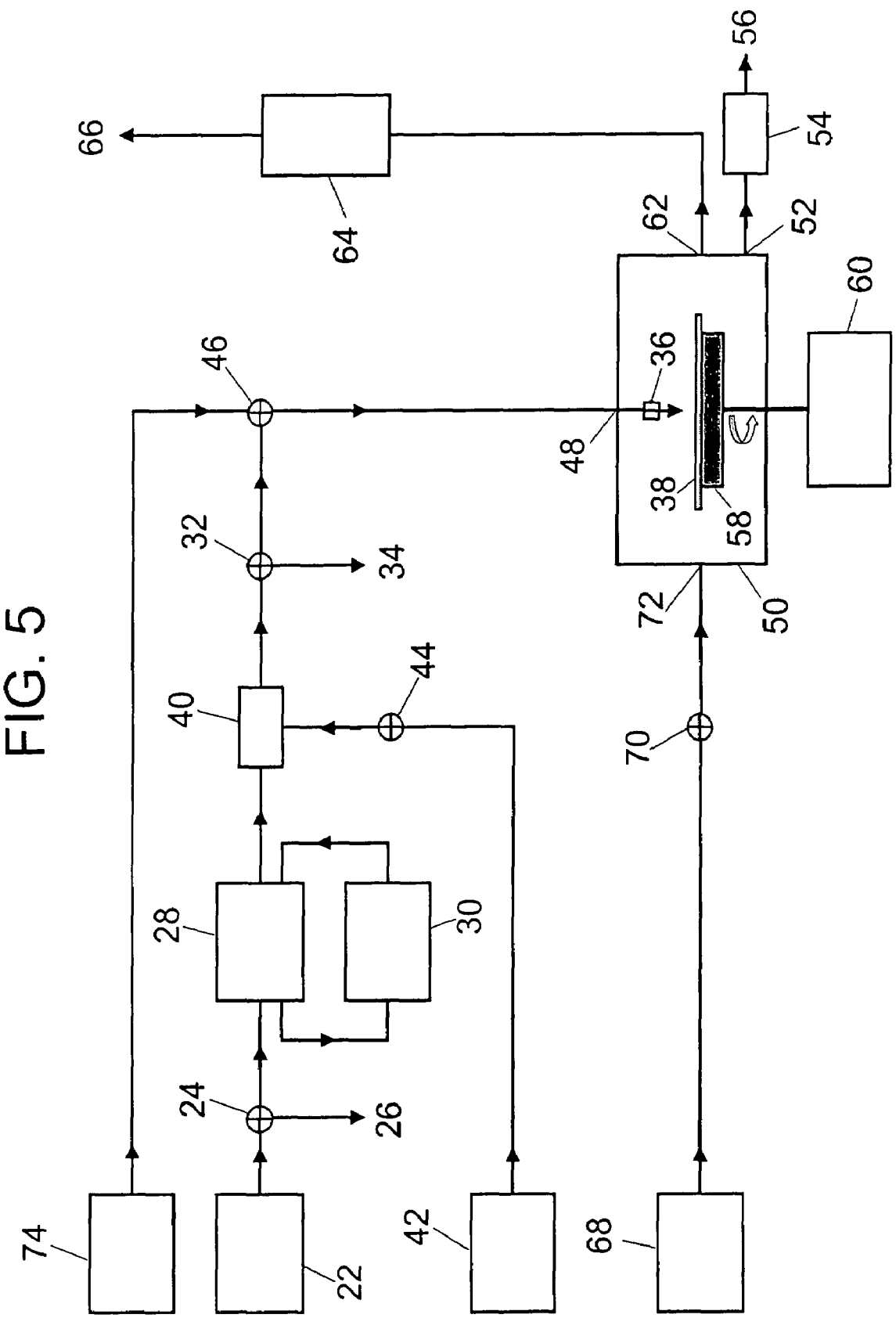
FIG. 5 illustrates a block diagram of a method of processing semiconductor wafers with a single-wafer spin processor.

Description—FIG. 5

One preferred method for applying the ozone-water solution to semiconductor substrates and the like is to apply the ozone-water solution to the surface of the substrate while spinning the substrate about an axis at a relatively high (1,000 to 4,000 rpm) rotational speed. The use of a this method for applying the ozone-water solution to semiconductor substrates and the like provides for a higher mass transport rate M than can be achieved by immersion techniques. With reference to FIG. 5, an ozonated water supply 22 is connected through a length of tubing to the common input of a three-way valve 24. The one outlet of three-way valve 24 is connected through a length of tubing to the cold process fluid inlet of a heat exchanger 28. The other outlet of three-way valve 24 is connected through a length of tubing to the facility drain-reclaim 26 for the ozone-water solution. The heated working fluid outlet of a recirculating heating unit 30 is connected through a length of tubing to the heated working fluid inlet of heat exchanger 28. The heated working fluid outlet of heat exchanger 28 is connected through a length of tubing to the working fluid return of recirculating heating unit 30. The heated process fluid outlet of heat exchanger 28 is connected through a short length of tubing to the inlet of chemical injector/mixer 40. The outlet of an injected chemical supply 42 is connected to the inlet of two-way valve 44. The outlet of valve 44 is connected to the chemical injection port of chemical injector/mixer 40. The outlet of chemical injector/mixer 40 is connected to the common inlet port of three-way valve 32. The one outlet of three-way valve 32 is connected through a short length to one inlet of a three-way valve etch/rinse valve 46. The common outlet of three-way etch/rinse valve 46 is connected through a short length of tubing to the process fluid inlet 48 to a dispense nozzle 36 located in a gas tight materials processing module 50. In the preferred embodiment the materials processing module 50 is fitted with a lid with a gas tight seal (not shown). The sealed materials processing module serves to contain the any ozone gas that is released from solution at the point of application. A pressurized DI water rinse supply 74 is connected through a length of tubing to the other inlet of port of the three-way etch/rinse valve 46. Pressurized DI water rinse supply 74 typically comprises a pressurized source of DI water connected though a liquid pressure regulator and a liquid flow controller and liquid particulate filter. The dispense nozzle 36 is spaced a relatively short distance (typically 0.5 to 10 cm) from the surface of the material 38 to be oxidized, cleaned, etch, or processed. The other outlet of three-way valve 32 is connected through a length of tubing to the facility drain-reclaim 34 for the heated ozone-water solution.

A process fluid drain outlet port 52 of the materials processing module 50 is connected through a short length of tubing to the inlet of liquid trap 54. When the ozone-water solution is dispensed onto the surface of the substrate at a given flow rate, the gas displaced from the housing may exit at approximately the same flow rate with a relatively small pressure drop. This insures that the pressure in the housing does not rise during the dispense cycle. The outlet of liquid trap 54 to connected by a length of tubing to the facility drain/reclaim 56 for process module liquid effluent. The wafer or substrate or the like is held by a spinner chuck 58. The chuck 58 may hold the wafer or substrate or the like (the material 38 to be oxidized, cleaned, etched, or processed) by the use of vacuum, edge clamps, or other means well known to those skilled in the art. The spinner chuck 58 is connected by a shaft or other means to wafer spinner motor 60. The motor, typically controlled by a microprocessor, can be programmed to accelerate the wafer or substrate or the like at a predetermined rate from zero rpm to a predetermined rpm, hold that rpm for a specified period of time, then decelerate at a predetermined rate to back to zero. Alternatively, the motor may be programmed to successively spin at several different rpm values chosen for different portions of the materials processing cycle. An ozone off-gas outlet port 62 is connected through a length of tubing to the inlet to an ozone catalytic unit 64. The outlet of ozone catalytic unit 64 is connected through a length of tubing to a facility exhaust vent 66. The diameter of the vent line and flow capacity of the ozone catalytic unit 64 is chosen so that the vent line is non-back pressuring. In the preferred embodiment the ozone destruction unit 64 is of the catalytic type filled with a catalyst such as CARULYTE® 200 (Carus Corporation). Since the waste ozone gas entering the catalyst unit contains water vapor, one may heat the catalyst unit with a heat tape and temperature controller to about 50 degree C. to prevent moisture condensation on the catalyst. The increased temperature also serves to increase the performance of the catalyst. The catalyst unit is sized to provide a sufficient residence time to convert the high concentration waste ozone off-gas to oxygen. The higher the waste gas flow rate, the larger the catalyst volume must be to achieve the conversion. The required residence time can be obtained from the catalyst supplier. Alternatively, the ozone destruction unit 64 can be thermal destruction unit in which the ozone gas-oxygen mixture is decomposed back to oxygen by raising the temperature of the waste ozone gas to about 300 degree C. A pressurized nitrogen purge gas supply 68 is connected through a length of tubing to the inlet port of a two-way valve purge valve 70. The outlet port of the two-way gas purge valve 70 is connected to a purge-gas inlet 72 to the materials processing module 50. Pressurized nitrogen purge supply 68 typically comprises a pressurized source of nitrogen connected though a gas pressure regulator and a gas flow controller and gas particulate filter.

In a single wafer processing embodiment one can use a single wafer spinner such as the all TEFLON® microprocessor controlled wafer spinner made by Laurell in which the spinner has been fitted with a gas tight lid seal. The Laurell spinner model WS400-6TFM/Lite is all TEFLON® and designed to accommodate wafers up to 150 mm diameter. The spinner acceleration rate, deceleration rate, and rpm can be set and controlled between 100 RPM and 6000 RPM. The spinner can be upgraded with a valve control option that enables the spinner microprocessor to control up to eight valves. This enables precise automated control of the purge to waste, etch dispense, and DI rinse dispense cycle times. Laurell makes spinners to accommodate 200 mm diameter wafers, 300 mm diameter wafers, and other substrates sizes and shapes.

Measured Photoresist Removal Performance with Equilibrium Processing with T2=T1

We have measured photoresist etch rate using a spin-etch configuration where ozone gas was dissolved in water at a given temperature T1 and given concentration. The ozone-water solution was dispensed at the same temperature T2 though a dispense nozzle to the center of spinning wafer coated with a layer of hard baked I-line positive photoresist or DUV positive photoresist.

We used 150 mm diameter silicon wafers coated with a thin (0.5 to 0.8 micron) and uniform layer of photoresist. We exposed the layer to a stream of ozone dissolved in water at a given concentration and temperature for a specified period time to partially remove some of the thickness of resist. We then measured the remaining layer thickness with an Nano-Spec ellipsometer and calculated an etch rate, the amount of organic material removed per unit time. The results are summarized in Tables 7 and 8 below.

TABLE 7

The measured etch rate when ozone is dissolved in water at a given temperature and given concentration and applied at a given flow rate though a dispense nozzle at the same temperature to the center of spinning wafer coated with a layer of hard baked I-line positive photoresist. The highest etch rate is achieved at the center of the wafer and the lowest etch rate is achieved at the edge of the wafer for the example shown.

| Dissolved Ozone Concentration (mg/L) | Dissolved Temp (deg C.) | Applied Temp (deg C.) | Flow Rate (L/min) | Wafer spin (RPM) | Max Etch Rate (A°/min) | Min Etch Rate (A°/min) |
|---|---|---|---|---|---|---|
| 75 | 9.9 | 9.9 | 1.2 | 4000 | 4270 | 3718 |
| 62 | 18.8 | 18.8 | 1.26 | 4000 | 6178 | 3538 |
| 24.9 | 27.8 | 27.8 | 1.26 | 4000 | 3524 | 1940 |

TABLE 8

The measured etch rate when ozone is dissolved in water at a given temperature and given concentration and applied at a given flow rate though a dispense nozzle at the same temperature to the center of spinning wafer coated with a layer of hard baked DUV positive photoresist. The highest etch rate is achieved at the center of the wafer and the lowest etch rate is achieved at the edge of the wafer for the example shown.

| Dissolved Ozone Concentration (mg/L) | Dissolved Temp (deg C.) | Applied Temp (deg C.) | Flow Rate (L/min) | Wafer spin (RPM) | Max Etch Rate (A°/min) | Min Etch Rate (A°/min) |
|---|---|---|---|---|---|---|
| 90 | 10.4 | 10.4 | 1.2 | 4000 | 1226 | 986 |
| 60 | 19.2 | 19.2 | 1.32 | 4000 | 2426 | 1774 |
| 24.9 | 27.8 | 27.8 | 1.23 | 4000 | 2308 | 1058 |

We know from our previous discussion that increasing the temperature of the water reduces the equilibrium dissolved ozone concentration as predicted by Henry's law. In the case of semiconductor wafers coated with a layer of organic polymer, we found that etch rate was higher at 20 degree C. than at 10 degree C. even though the equilibrium dissolved ozone concentration was significantly lower (60 mg/L at 20 deg. C. compared to 90 mg/L at 10 deg. We see that the maximum etch rate first increases with increased temperature and then the etch rate decreases with further increases in temperature. We see that I-line positive photoresist is etched by the process at a faster rate than DUV resist. This is because the I-line positive photoresist has a higher value of S than DUV positive photoresist at a given temperature.

These etch rates are not high enough to provide reasonable throughputs in a single wafer configuration.

Measured Photoresist Removal Performance with Non-Equilibrium Processing with T2>T1

We tested one embodiment of the invention in which which ozone is dissolved in water at a lower temperature to produce a high dissolved concentration, then passed at given flow rate though a point of use heater, and applied at a higher temperature to the center of spinning wafer. with both I-line and DUV positive photo resist and showed that we were able to achieve an I-line positive photoresist etch rate of 16,812 A°/minute and DUV positive photoresist etch rate of 10,626 A°/minute. (See Tables 9 and 10). These etch rates are about a factor of five higher than the highest etch rates than we were able to initially achieve using conventional techniques (compare to Tables 7 and 8). The mass transport M is generally higher at a higher RPM and the etch rate is higher as well.

We again see that I-line positive photoresist is etched by the process at a faster rate than DUV resist because the I-line positive photoresist has a higher value of S than DUV positive photoresist at a given temperature.

TABLE 9

The measured etch rate when ozone is dissolved in water at a lower temperature to produce a high dissolved concentration, then passed at given flow rate though a point of use heater, and applied at a higher temperature to the center of spinning wafer. The wafer is coated with a layer of hard baked I-line positive photoresist. The highest etch rate is achieved at the center of the wafer and the lowest etch rate is achieved at the edge of the wafer.

| Dissolved Ozone Concentration (mg/L) | Dissolved Temp. (deg C.) | Applied Temp. (deg C.) | Flow Rate (L/min) | Wafer spin (RPM) | Max Etch Rate (A°/min) | Min Etch Rate (A°/min) |
|---|---|---|---|---|---|---|
| 95 | 7.5 | 49.5 | 2.7 | 1000 | 20208 | 9459 |
| 95 | 7.5 | 47.5 | 2.7 | 4000 | 23850 | 16812 |

TABLE 10

The measured etch rate when ozone is dissolved in water at a given temperature and given concentration and applied at a given flow rate though a point of use heater and through a dispense nozzle at a higher temperature to the center of spinning wafer coated with a layer of hard baked DUV positive photoresist. The highest etch rate is achieved at the center of the wafer and the lowest etch rate is achieved at the edge of the wafer.

| Dissolved Ozone Concentration (mg/L) | Dissolve Temp. (deg C.) | Applied Temp. (deg C.) | Flow Rate (L/min) | Wafer spin (RPM) | Max Etch Rate (A°/min) | Min Etch Rate (A°/min) |
|---|---|---|---|---|---|---|
| 95 | 7.5 | 48.5 | 2.7 | 1000 | 16227 | 6117 |
| 95 | 7.5 | 47.5 | 2.7 | 4000 | 19413 | 10626 |

We have presented experimental results on a method for removing photoresist at high speed using a solution of ozone gas dissolved in water comprising the steps of a) dissolving high ozone gas in water at a relatively low predetermined temperature to form an ozone-water solution with a high dissolved ozone concentration, b) heating the ozone-water solution with a point-of-use water heater (a liquid to liquid heat exchanger) to quickly increase the solution temperature to a predetermined higher temperature, and c) applying the heated ozone-water solution to the center of a photoresist coated wafer rotating at high speed. The etch rate is increased, not only because the surface reaction rate is increased at the higher temperature, but also because the heated ozone-water solution has a much higher dissolved ozone concentration at the higher temperature than could be achieved if the ozone gas was initially dissolved in water at the higher temperature under equilibrium conditions.

Alternative Means for Applying Ozone-Water Solution to The Substrate: The application of the ozone-water-other chemicals solution to the surface or surfaces of the material to be processed can be accomplished in a number of different ways. In the preferred embodiment the solution can be applied to the center of the wafer through a single solid stream nozzle 36 with an inside diameter of about 6 mm positioned to apply a flow of water to the wafer at the center. In a second embodiment the solution can successively applied to different positions between the center and edge of the wafer. In this second embodiment the ozone-water solution can be flowed through a nozzle which can be successively positioned at different locations from the center to the edge of the wafer or from the edge to the center of the wafer. The dwell time at each position can be controlled to reduce the radial variation in the etch rate or cleaning rate or oxidation rate over the duration of the materials processing cycle. In a third embodiment the solution can be applied the surface of the wafer with multiple nozzles 36A, 36B, 36C, . . . (not shown) In the fourth embodiment one or more nozzles may be mounted on one or more rotating spray arms (not shown) positioned to apply the solution to one or more surfaces of the material to be oxidized. The ozone-water-other chemicals solution can be applied to the surface or surfaces of the material to be processed by other means familiar to those skilled in the art.

Alternative Means for Applying DI Rinse Water to The Substrate. In an alternative embodiment the DI rinse water may be applied to the substrate with a separate set of one or more rinse nozzles (not shown). Rinse nozzles may be chosen for optimum rinse performance at a predetermined rinse flow rate and the nozzles may be positioned to rinse one more surfaces of the substrate.

Optional Instrumentation Upstream of the Dispense Point: A dissolved ozone monitor and temperature sensor may be inserted in the short length of tubing just upstream of the dispense nozzle 36. This instrumentation provides a continuous readout of the dissolved ozone concentration and temperature of the heated ozone-water solution just upstream of the dispense point. This can be a source of useful diagnostic information during process development. Since the elements add additional volume between the inlet of the water heater 28 and the point of application of the solution to the material 38, the internal volume of these optional instrumentation sensors should be small so that the residence volume through which the heated ozone-water solution must pass is kept small and the time delay between heating the ozone-water solution and applying the heated ozone-water solution to the material 38 is kept sufficiently small as discussed earlier.

Alternative Locations of the Back Pressure Regulator for an Ozonated Water Supply Designed to Dissolve Ozone Gas in Water at a Pressure Greater Than 1 Atmosphere (14.5 psia.) In an ozonated water supply designed to dissolve ozone gas in water at a pressure above 14.5 psia, a gas back pressure regulator is typically placed in the waste-ozone off-gas (undissolved ozone gas) outlet of the ozone gas-water contactor element and a liquid back pressure regulator is typically placed in the ozonated outlet line of the ozone-gas water contactor element. In the preferred embodiment for spin processing or semiconductor wafers and the like, the apparatus is designed to apply the ozone gas-water solution to the material to be oxidized 38 in a material processing module operated at one atmosphere pressure. In one embodiment the liquid back pressure regulator may be positioned between the outlet of the ozonated water supply 22 and the inlet of the two three-way valve 24. Alternatively, the liquid back pressure regulator may be moved to a position just upstream of the dispense nozzle 36 to minimize the time available for the ozone gas to leave the ozone-water solution from the time the pressure is reduced to atmospheric pressure and the solution is applied to the material.

In systems designed to apply the ozone gas-water solution to the material to be oxidized 38 in a material processing module operated at the same pressure as a pressurized ozone-gas-water contactor element, the liquid back pressure regulator may be positioned at the liquid outlet of a pressurized materials processing module and the gas back pressure regulator, which is typically placed in the waste-ozone off-gas outlet of the ozone gas-water contactor, can be relocated to the waste-ozone off-gas outlet of the materials processing module.

Operation—FIG. 5

A preferred technique for applying the ozone-water solution to semiconductor substrates and the like is to apply the ozone-water solution to the surface of the substrate while spinning the substrate about an axis at a relatively high (1,000 to 4,000 rpm) rotational speed. The use of a this method for applying the ozone-water solution to semiconductor substrates and the like provides for a higher mass transport rate M than can be achieved by immersion techniques. One very important use of the preferred embodiments is for the removal of photoresist and post etch residue from semiconductor wafers and the like. Let us describe the operation for a typical photoresist or post etch residue removal application. With reference to FIG. 5, ozononated water supply 22 supplies an ozonated water formed by dissolving ozone gas at a gas phase concentration of 240 mg/L and pressure of 14.5 psia (1 bar) into DI water chilled to a temperature of about 8 degree C. The ozonated water supply delivers the chilled ozone gas-water solution at a dissolved concentration of about 90 mg/L and at a flow rate of 2.7 Liter/min through three way purge valve 24, through heat exchanger 28 or point-of-use heater 29 where the solution temperature is increased to about 50 degree C., through chemical injector/mixer 40, through three-way purge valve 32, through three-way etch/rinse valve 46, through materials-processing-module inlet 48, through dispense nozzle 36 where the heated ozone-water solution is applied to the center of a semiconductor wafer 38 spinning at about 3.500 to 4,000 mm. Under these conditions the inventors have shown that the dissolved ozone concentration downstream of the point-of-use heater is approximately 75 mg/L, more than 80 percent of the concentration at the inlet of the point-of-use heater. The ozone-water solution traverses the surface to the wafer from the point of application to the edge of the wafer and enters the process fluid outlet of the materials-processing-module where the ozone-water solution and other liquid effluents from the process are carried through a trap to facility drain 56. The trap prevents back flow of an gases from the facility drain reclaim reservoir. The nitrogen purge supply flows dry filtered nitrogen gas, or another suitable gas, at a flow rate of about 0.5 L/min, through the two-way nitrogen purge valve 70, to the inlet of the materials-processing-module 72. The nitrogen gas assists in the removal of any ozone gas that leaves the ozone-water solution inside the materials-processing-module and provides an nitrogen blanketed processing environment. The ozone off-gas, nitrogen, and other waste gases from the process, exit from the materials-processing-module at outlet port 62, pass through the catalyst unit 64 where the waste ozone gas is converted to oxygen before exiting to the facility exhaust vent 66. The period during which the ozone-water solution is applied to the spinning substrate can be designated as the duration of the etch clean cycle. Once the etch cycle is completed, the three way purge valve 32 can be set to direct the flow of the heated ozone-water solution to the facility drain/reclaim 34 for the heated ozone-water solution and the three-way etch/rinse valve 46 can be placed in the rinse position to allow the rinse water to flow to the materials-processing-module. DI water can then flow from the pressurized DI water supply through the three way valve 46, through materials-processing-module inlet 48, through dispense nozzle 36 where the DI water solution is applied to the center of a semiconductor wafer 38 spinning at about 3500 to 4,000 rpm. The period during which the DI rinse water is applied to the spinning substrate 38 can be designated as the duration of the rinse cycle. Once the rinse cycle is completed, the three-way etch rinse valve 46 can be returned to the etch position while the three-way purge valve 32 remains set to direct the flow of the heated ozone-water solution to the facility drain/reclaim 34 so that all liquid flows to materials-processing-module are off and the wafer can be spun dry. The period during which all liquid flows to the materials processing module are off and the substrate is spinning can be designated as the duration of the spin dry cycle. The spin RPM and duration of each cycle can be set to a predetermined value for a particular process application.

Example Process Conditions for Photoresist Removal And Post Etch Residue Removal. A typical wafer spin processing sequence my include spin etch or cleaning or oxidation cycle, a spin rinse cycle, and a spin dry cycle. Example process conditions for photoresist removal and post etch residue removal with 150 mm diameter wafers in a single wafer spin processing configuration are summarized in Table 11 below.

TABLE 11

Example Process Conditions for Photoresist Removal And Post Etch Residue Removal- Single Wafer Processing Configuration - 150 mm Diameter Wafers -

| ETCH CLEAN | |
|---|---|
| Dissolved Ozone Concentration (mg/L)/(millimoles/liter) | 70 to 210 mg/L (1.5 to 4.5 millimoles/L) |
| Hydroxyl Radical Scavenger | Carbonate, Bicarbonate, Phosphate, Acetate |
| Hydroxy Radical Scavenger Concentration (millimoles/liter) | 5 to 10 x dissolved ozone concentration |
| pH | 6.5 to 7.5 |
| Ozone-Water Solution Temperature at the point of application (° C.) | 40 to 60 |
| Spin Etch Speed (RPM) | 2,000 to 4,000 |
| Ozone-Water Solution Flow Rate (L/min) | 1.0 to 3.0 |
| Etch Duration (min) | 0.5 to 6.0 |
| RINSE | |
| DI Rinse Temperature (° C.) | 20 |
| Spin Rinse Speed (RPM) | 2,000 to 4,000 |
| DI Rinse Flow Rate (L/min) | 0.5 to 1.0 |
| DI Rinse Duration (min) | 0.33 to 1.0 |
| DRY | |
| Spin Dry Speed (RPM) | 2,000 to 4,000 |
| Dry Duration (min) | 0.33 to 1.0 |

These process conditions are typical for this type of application. However, process conditions outside the range of values presented in the Table 11 above can also provide satisfactory performance for this and other applications and wafer processing configurations. For example, batch wafer spinning configurations in which two to four cassettes of wafers are processed at one time typically operate at a lower RPM and lower etch flow rate per wafer. The RPM for a batch spinner is typically in the range of 500 to 1500 RPM. The total etch chemistry flow rate for a batch wafer spinner is typically in the range of 10 to 20 liters/minute. The lower RPM and lower flow rates will yield a lower mass transport rate and lower etch rate. The temperature at which the etch rate will become mass transport limited will be lower since the mass transport rate is lower as discussed earlier.

Process Performance Measured by the Inventors: A typical duration for an etch cleaning cycle for removing photoresist and post etch residue is 0.5 to 6 minutes. The inventors have demonstrated the ability to remove hard baked Olin OCG-897 I-line positive photoresist from semiconductor wafers at an etch rate of approximately 17,000 Angstroms/minute. The inventors have demonstrated the ability to remove hard baked SHIPLEY® UV6 DUV positive photoresist from semiconductor wafers at an etch rate of approximately 11,000 Angstroms/minute. The etch rate is generally lowest at the wafer edge. The reported etch rates are those measured at the wafer edge at a flow rate of 2.7 L/min., a dissolved ozone concentration of about 75 mg/L, a spin speed of about 4,000 RPM, and temperature of approximately 50 degree C., and hydroxyl radical scavenger concentration of about 15 millimoles/Liter. The inventors have demonstrated the ability to remove both post metal etch resist and resist residue under similar conditions from test structures using 0.35 μm technology with I-line resist in less than 1.5 minutes at 50 degree C. The inventors have demonstrated the ability to remove both post metal etch resist and resist residue from test structures using 0.18 μm technology with DUV resist in less than 3.0 minutes at 50 degree C. It is useful to compare to cycle times of this new ozone-water post etch cleaning process with the current process based upon plasma ashing and solvent residue removal. This is summarized in Table 12 below.

TABLE 12

Post Metal Etch Clean at 50 deg. C.: Comparison with Conventional Process

| | CONVENTIONAL PROCESS | | | NEW OZONE-WATER PROCESS | | |
|---|---|---|---|---|---|---|
| Step # | Process Step | I-line resist Time Req'd (min) | DUV resist Time Req'd (min) | Process Step | I-line resist Time Req'd (min) | DUV resist Time Req'd (min) |
| | single wafer process | | | single wafer process | | |
| 1 | O2 Ash | 3.0 | 5.0 | Ozone Etch | 1.5 | 3.0 |
| 2 | Hot/Cold DI Rinse | 1.5 | 1.5 | Cold DI Rinse | 0.5 | 0.5 |
| 3 | Spin Dry | 0.5 | 0.5 | Spin Dry | 0.5 | 0.5 |
| | batch process | | | | | |
| 4 | Batch Solvent Clean | 10 | 10 | NA | | |
| 5 | Batch DI Rinse | 5 | 5 | NA | | |
| 6 | Batch Spin Dry | 5 | 5 | NA | | |

This new ozone-water process has demonstrated the potential to replace the conventional plasma ashing and solvent cleaning process used for post-metal-etch clean. The process can be readily integrated into a single wafer cluster tool at a low cost. A single ozone-water spin etch module would replace the plasma ashing module and hot DI rinse/spin dry module. The process has demonstrated the ability to remove the post metal etch resist and resist residue from the test structures using 0.35 μm technology with OCG 897-12 positive I-line resist in 1.5 minutes. The process has demonstrated the ability to remove the post metal etch resist and resist residue from the test structures using 0.18 $\mu$m technology with SHIPLEY® UV6 positive DUV resist in 3.0 minutes.

The process has demonstrated the ability to remove the post oxide etch resist and resist residue from the test structures using 0.35 $\mu$m technology with OCG 897-12 positive I-line resist in 1.0 minutes. The process has demonstrated the ability to remove the post oxide etch resist from the test structures using 0.18 $\mu$m technology with SHIPLEY® UV6 positive DUV resist in 3.0 minutes. However, the process has not yet demonstrated the ability to completely remove the post-oxide-etch residue from the test structures using 0.18 $\mu$m technology with SHIPLEY® UV6 positive DUV resist with a cycle time of 5 minutes. In applications using I-line resist only the new ozone-water process has the potential to replace the conventional plasma ashing and solvent cleaning process used for post-oxide etch clean.

Materials Processing Method with Spray Processor

Figure 6:
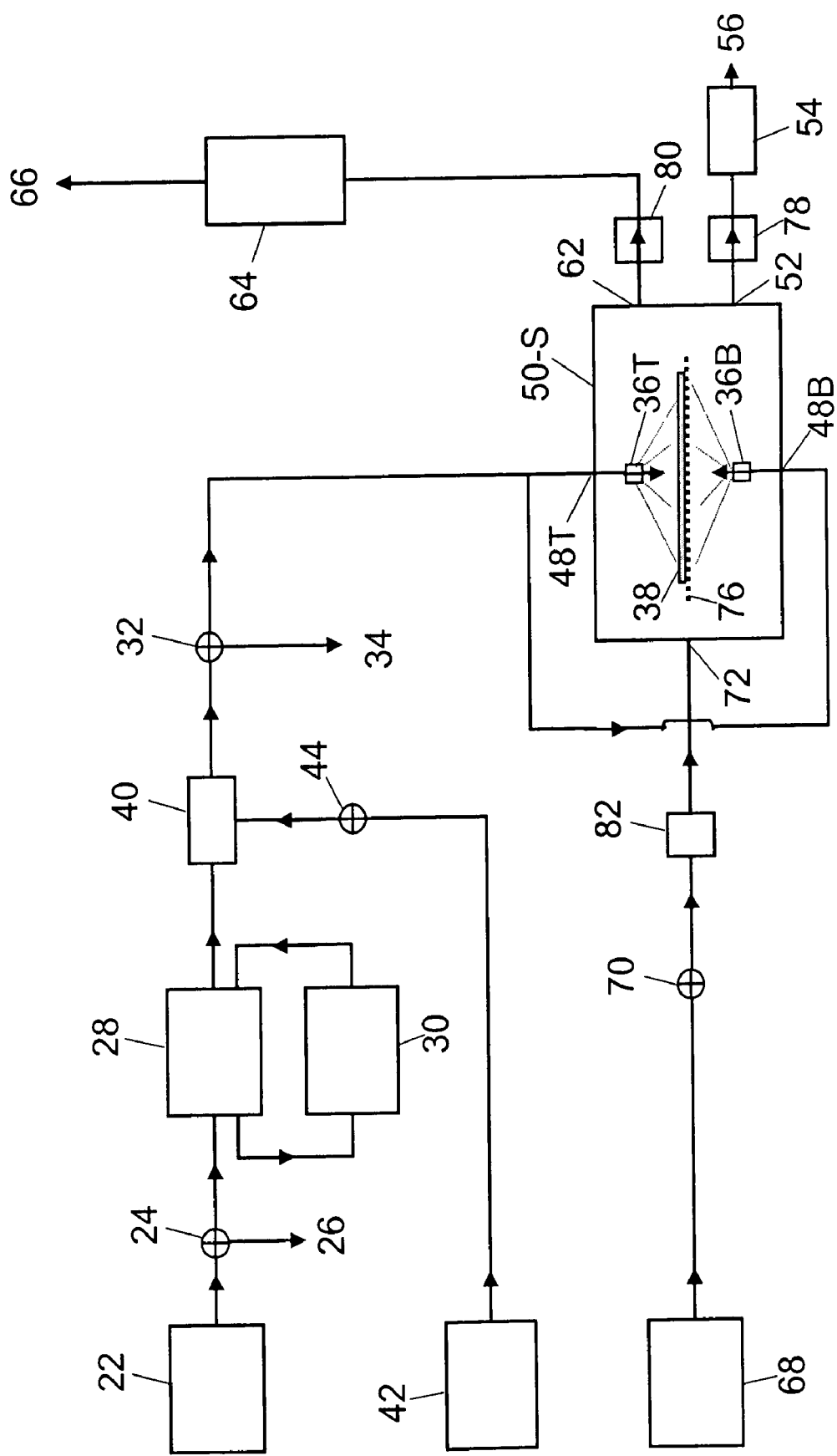
FIG. 6 illustrates a functional block diagram of a method of processing materials with upper and lower rotating spray arms (dishwasher geometry).

Description—FIG. 6

There are a number of applications in which one may wish to process materials such as medical instruments, bio-materials, and medical devices for the purpose of surface treatment, cleaning, disinfection, or sterilization. In these types of applications alternative processing configurations can be used. The principal difference between the spray processor and the spin processor shown in FIG. 6 is that the spray processor does not spin the material to be processes at high RPM. The materials to be processed may not be able to be spun at high RPM because of their mass, size, or asymmetric shape. In this case the instruments or materials to be processed can be placed on a rack or wire mesh support and the heated ozone-water-chemical solution can be applied to the materials from multiple directions using one or more spray heads. The materials may be mounted on a rack or supporting structure that permits good access for the spray and the heated ozone-water-chemical solution my be applied with one or more spray heads. The spray heads may be fixed in position, mounted on rotating spray arms, mounted on translating spray arms. The rack or structure that supports the materials to be processed may be fixed in position, may be slowly rotated at low rpm, or may be slowly translated. A materials processing module designed for sterilization of materials or devices or instruments must have several additional elements to prevent microbial contamination of the materials processing module. The additional elements may be understood by referring to FIG. 6. The elements 22, 24, 26, 28, 29, 30, 32, 34, 36, 38, 40, 42, 44, 48, 50, 52 54, 56, 62, 64, 66, 68, 70, and 72 are the same as defined earlier. A materials processing module designed for sterilization does not require a separate rinse supply. Accordingly, the rinse supply 74 and etch rinse valve 46 is not required. Three-way valve 32 is connected by short lengths of tubing through the process fluid inlet 48T and 48B to top spray assembly 36T and bottom spray assembly 36B located above and below a support structure 76. A drain line check valve 78 is located between the process-fluid outlet 52 and the trap 54 to prevent backflow to the process module. A vent line check valve 80 is located between the off-gas outlet 62 and the catalytic ozone destruction unit 64 to prevent backflow to the process module. A purge gas sterile filter 82 is located between the outlet of two-way purge gas valve 70 and the purge gas inlet 72.

Operation—FIG. 6

In reference to FIG. 6, the operation of the spray processor is similar to that of the spin processor. The ozone gas-water solution is formed at a relatively low temperature and heated at the point-of-use as described earlier. Additional chemicals can be injected at the point-of-use from one or more chemical supplies as described earlier. The heated ozone-water solution flows from the outlet of three-way valve 32 through the process fluid inlets 48T and 48B in the spray type materials processing module 50-S to the top and bottom spray assemblies 36T and 36B The material to be processed or sterilized 38 is positioned on an open support structure 76. The support structure is designed to not block the spray from impinging on the surfaces of the material to be processed or sterilized. The heated ozone gas-water solution is sprayed onto all surfaces of the materials or instruments or devices with the top and bottom spray assemblies 36T and 36B. If the instruments have internal channels that must be sterilized, then the heated ozone gas-water solution may be also flowed through those internal channels as well. Ozone dissolved in water is a zero residue sterilant. However, if additional chemicals such as surfactants are injected and mixed with ozone-water solution to improve wetting and soil removal during the sterilization cycle, then the residues of those added chemicals may need to be rinsed from the surfaces of those instruments or materials in a subsequent sterile rinse cycle.

A sterile water rinse method not requiring a sterile filter. In the prior art the sterile rinse has been implemented by passing water through a 0.2 micron sterile filter. This type of filter becomes clogged with use and must be replaced at regular intervals. In the present embodiment, one can use the heated ozone gas-water solution as a sterile rinse solution. The solution may be used with no additional injected chemicals except perhaps a chemically benign buffer and scavenger. One good candidate buffer is a phosphate buffer made by mixing KH2PO4 and Na2HPO4. Another candidate buffer is boric acid and sodium borate. The phosphate or borate will also serve as a hydroxyl radical scavenger. The ozone gas dissolved in water to form a supply of ozonated water will quickly kill the most resistant organisms. The 12D sterilization time for the most resistant water-borne organisms such as Giardia and Cryptosporidium at a dissolved ozone concentration of only 60 mg/L is 0.2 minutes (12 seconds) as shown in Table 13. The residence time of a typical ozone gas-water contactor used in an ozonated water supply is much longer than 12 seconds. The residence time in a recirculating contactor can be higher. Accordingly, the ozone-water solution dispensed from the ozonated water supply at a concentration of about 60 mg/L will be sterile water. When the ozone-water solution is passed through the point-of-use heater 28 or 29 and heated to a higher temperature (50 degree C. for example), the concentration will decay to a low value with an exponential decay time constant estimated by the inventors to be about 25 seconds. The materials processing chamber may be continuously purged with sterile nitrogen or sterile air during the sterilization cycle to sweep the waste ozone off-gas from the chamber. When the instruments or devices are removed from the instrument chamber at the end of the sterilization and optional rinse cycle, the dissolved ozone concentration will have decayed to a very low value. Example process conditions for medical instrument and medical device sterilization are shown in Table 14.

TABLE 13

The lethality of ozone dissolved in water at a specified concentration against microorganisms in aqueous suspension in a stirred reactor. The time required to achieve a 12 log reduction in the specified organism at two different concentrations is calculated from the measured D value data. The D value is the time required to reduce the number of viable organisms by a factor of 10 at a specified sterilant concentration C

| Microorganism | D secs C = 10 mg/l | 12CD mg.min/l | 12D minutes C = 60 mg/l | note |
|---|---|---|---|---|
| *Eschrichia Coli* | 0.03 | 0.06 | 0.001 | a |
| *Striptococcus Fecalis* | 0.045 | 0.09 | 0.002 | a |
| *Mycobacterium Tuberculosum* | 0.15 | 0.3 | 0.005 | a |
| Polio Virus | 0.06 | 0.12 | 0.002 | a |
| *Endamoeba Histolytica* | 1 | 2 | 0.033 | a |
| *Bacillus Megatherium* (Spores) | 3 | 6 | 0.100 | a |
| *Giardia Lamlia, Giardia Muris* (Cysts) | 6 | 12 | 0.200 | a |
| *Cryptosporidium* | 6 | 12 | 0.200 | a |

Note
a: Block, 1978; Sobsey, 1989: D values measured at a dissolved concentration of 1–2 mg/l, pH 7, and temperature of 15° C.

TABLE 14

Example Process Conditions for Medical Instrument and Medical Device Sterilization

STERILIZE

| | |
|---|---|
| Dissolved Ozone Concentration (mg/L)/(millimoles/liter) | 70 to 210 mg/L (1.5 to 4.5 millimoles/Liter) |
| Hydroxyl Radical Scavenger | Examples: Carbonate, Bicarbonate, Phosphate, Acetate |
| Hydroxyl Radical Scavenger Concentration (millimoles/liter) | 5 to 10 x dissolved ozone concentration |
| pH Buffer | Examples: Phosphate, Borate |
| pH Buffer Concentration | ~10 millimoles/Liter |
| pH | 6.5 to 7.5 |
| Surfactant - optional | Non-ionic and Anionic Mixture |
| Sequestering Agent - optional | Examples: Sodium Tripolyphosphate (STTP) |
| Sequestering Agent Concentration | 10 millimoles/Liter |
| Ozone-Water Solution (Sterilant) | 30 to 50 |
| Temperature at the point of application to the (° C.) | |
| Ozone-Water Solution Flow Rate (L/min) | 5 to 10.0 |
| Sterilization Cycle Duration (min) | 5 to 10.0 |
| RINSE - optional | |
| DRY - optional | |

Process Performance Measured by the Inventors: The inventors have calculated the sterliant efficacy of an ozone-water solution at different solution temperatures for a dissolved ozone concentration of 60 mg/L based upon inactivation rates, measured by the inventors under equilibrium conditions, for AOAC porcelain penicylinders and AOAC Dacron polyester suture loop carriers inoculated with 1E6 Bacillus Subtilus spores according to the AOAC protocol.

Inactivation times are influenced not only by surface reaction rate but also by the dissolved concentration. They are also confounded by the statistical nature of the carrier inactivation process. We computed the average 12CD value for inactivation of carriers at each of the different equilibrium temperatures and dissolved concentrations. The use of the concentration-time product effectively normalized the results by the concentration. The results showed there is a very strong temperature dependence of inactivation rate. The analysis demonstrated that the inactivation at 20 deg. C. is not mass transport limited, but surface reaction rate (temperature) limited.

The results for penicylinders are presented in Table 15. The parameter 12CD is the concentration-time product for inactivation of a million spore challenge with a million to one assurance level. We see that an increase in the temperature from 20 deg. C. to 30 deg. C. (10 deg. C. increase), causes the 12CD value to decrease by more than a factor of 4 from 14 to 2.6. In next column (col. 6). We have computed the value of 12 CD at 10, 30, 40, and 50 deg. C. from the measured value at 20 deg. C. The computation is based upon the following hypothesis: 1) the surface reaction rate coefficient S increases by a factor of 2 for every 5 deg. C. increase in temperature (similar to that observed for the oxidation of polymer films), and 2) the overall reaction rate is dominated by the surface reaction rate over the temperature range. This assumption seems to be valid up to 30 deg. C. We have also computed the predicted 12D sterilization time at a dissolved ozone concentration of 60 mg/L (see table column 7). Further measurements will be required to determine the point at which the reaction becomes mass transport limited.

TABLE 15

The measured and calculated temperature dependence of the D value and 12 D sterilization time for porcelain penicyliders inoculated with *bacillus subtilis* (BS) var niger spores (ATCC 19659) according to AOAC protocol. The initial spore population was at least 1E6 CFU per carrier

| Temp. deg. C. | No. of Replicate Tests | Total No. of Carriers Tested | D value min. @ 60 mg/L | 12CD hr. mg/L measured | 12CD hr. mg/L calculated from values @ 20 deg. C. | 12D time minutes @ C = 60 mg/L |
|---|---|---|---|---|---|---|
| 10 | | | | | 56 | 56 |
| 20 | 24 | 153 | 1.2 | 14 | 14 | 14 |
| 30 | 7 | 43 | .3 | 2.6 | 3.5 | 3.5 |
| 40 | | | | | .875 | .875 |
| 50 | | | | | .215 | .215 |

The results for polyester suture loops are presented in Table 16. We see that polyester suture loops are more resistant to inactivation than penicylinders, and hence the FDA approved cycle time is generally determined by suture loop inactivation time. We see that an increase in the temperature from 10 deg. C. to 20 deg. C. to 30 deg. C. (10 deg. steps), causes the 12CD value to decrease by nearly a factor of 4 for each step from 285 to 71 to 26. In next column(col. 6) we have again computed the value of 12 CD at 10, 30, 40, and 50 deg. C. from the measured value at 20 deg. C. based upon the assumption stated above. Again, the results are remarkably consistent with the model. However, there is only one replicate at 30 deg. C. More data is required to prove the hypothesis.

TABLE 16

The measured and calculated temperature dependence of the D value and 12 D sterilization time for polyester suture loops inoculated with *bacillus subtilis* (BS) var niger spores (ATCC 19659) according to AOAC protocol. The initial spore population was at least 1E6 CFU per carrier

| Temp. deg. C. | No. of Replicate Tests | Total No. of Carriers Tested | D value min. @ 60 mg/L | 12CD hr. mg/L measured | 12CD hr. mg/L calculated from values @ 20 deg. C. | 12D time minutes @ C = 60 mg/L |
|---|---|---|---|---|---|---|
| 10 | 13 | 168 | 24 | 285 | 284 | 284 |
| 20 | 5 | 64 | 6 | 71 | 71 | 71 |
| 30 | 1 | 6 | 1.5 | 26 | 17.8 | 17.8 |
| 40 | | | | | 4.4 | 4.4 |
| 50 | | | | | 1.1 | 1.1 |

Materials Processing Method with Immersion Processing

Figure 7:
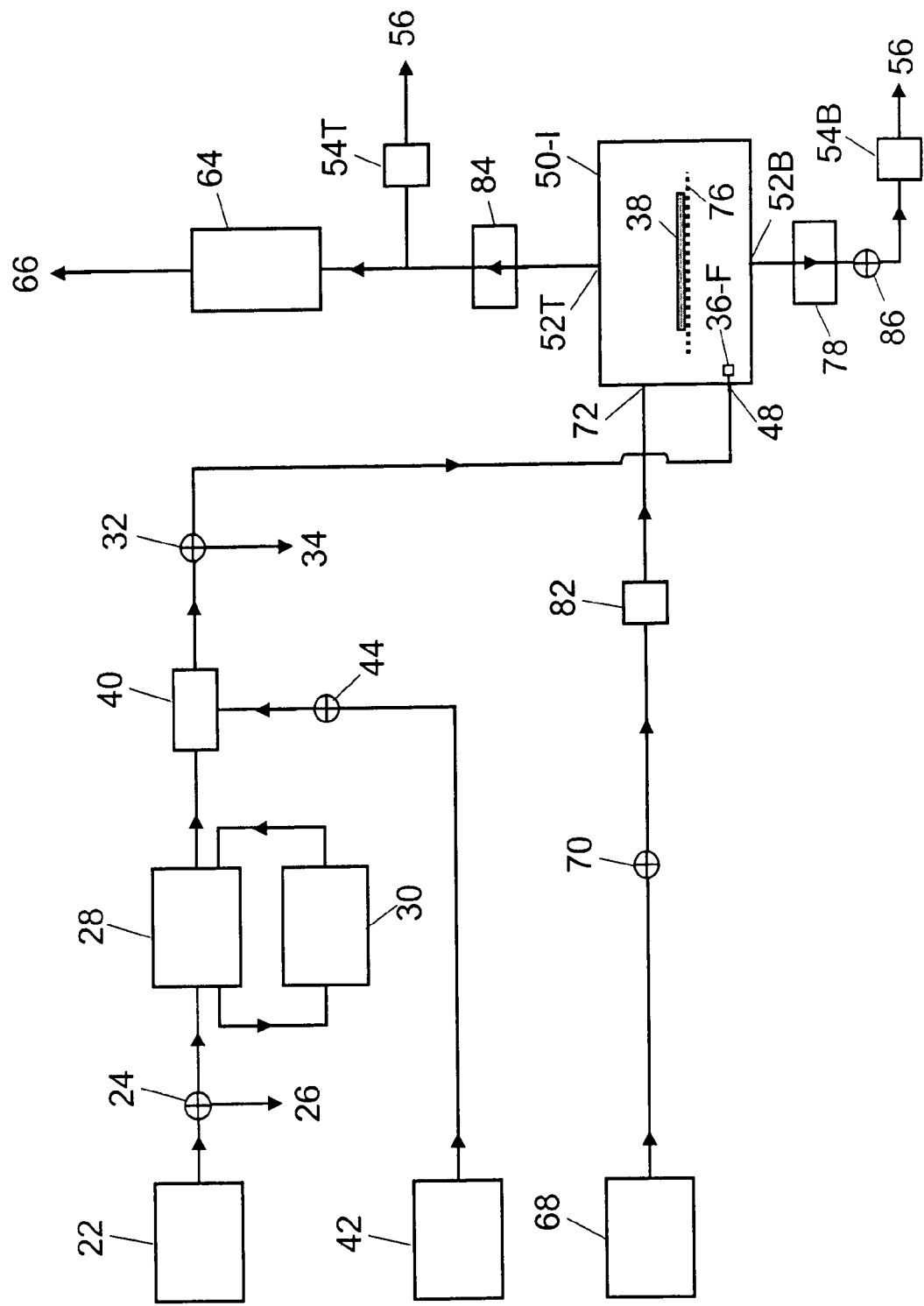
FIG. 7 illustrates a functional block diagram of a method of processing materials with an immersion design.

Description—FIG. 7

Spin processing and spray processing configurations can generally provide better mass transport to the surface of the material to be processed than can immersion processing configurations. However, there are some applications where immersion processing can offer other advantages with respect to full wetting of complex surfaces. This can be particularly important in sterilization processing applications. In reference to FIG. 7, the outlet of three way valve 32 is connected by a short length of tubing to the process fluid inlet 48 of an immersion type materials processing module 50-I to a fill nozzle 36-F. The drain outlet 52B is connected by a short length of tubing to drain check valve 86. The outlet of check valve 86 is connected by a length of tubing to a drain line trap 54B. The drain line trap 54B is connected by a length of tubing to facility drain/reclaim 56. Purge gas supply 68 is connected by a short length of tubing to the inlet of two-way valve 70. The outlet of two-way valve 70 is connected to the inlet of sterile filter 82. The outlet of sterile filter 82 is connected to the module purge gas inlet 72. The overflow/waste gas vent outlet 52T is connected through a length of tubing to the inlet of a check valve 84. The outlet of the check valve 84 is connected to the inlet of a trap 54T. The outlet of trap 54T is connected to the facility drain/reclaim for process effluent 56. The outlet of check valve 84 is also connected to the to inlet of the catalytic ozone destruction unit 64. The outlet of the catalytic ozone destruction unit 64 is connected to a facility exhaust vent 66. The material(s) to be processed 38 may be in position inside the process module with a support structure 76.

Operation—FIG. 7

In reference to FIG. 7, the ozone gas-water solution is formed at a relatively low temperature and heated at the point-of-use as described earlier. Additional chemicals can be injected at the point-of-use from one or more chemical supplies as described earlier. The heated ozone-water solution flows from the outlet of three-way valve 32 through the process fluid inlet 48 in an immersion type material processing module 50-I to the a fill nozzle 36-F while the drain valve 86 is closed. Once the immersion module fills completely to the top with the heated ozone-water solution and the materials to be processed are immersed in the heated ozone-water solution, the heated ozone-water solution, together with any gases, flows out of the overflow/vent outlet 52T through filter 84, through the trap 54T to the facility drain/reclaim 56 for process effluent. Most of the undissolved gases that exit from the module pass through the catalytic ozone destruction unit 64 to the facility exhaust vent 66. The immersion processing module can be designed with baffles or other means to insure that the surfaces of the materials are continuously exposed to fresh heated ozone-gas-water solution as the solution is flowed from the module inlet 48 to the module overflow/vent outlet 52T. The module can be designed to hold instruments, devices, or materials with a minimum volume and thereby decrease the residence of the heated zone-water solution for a given ozone-water solution flow rate. The dissolved ozone concentration of the heated ozone-water solution will decay with time with a temperature dependent decay rate as discussed earlier. The residence time of the solution in the immersion module can be set at a predetermined value to insure that the dissolved concentration does not fall below a predetermined value for the duration of the cleaning or sterilization or oxidation process cycle. Once the cleaning cycle is complete the flow of the heated ozone-water solution to the process module may be stopped by setting the thee-way valve 32 to direct the flow to the facility drain/reclaim 34 for the heated ozone-water solution. The module may be drained by opening the drain valve 78 and opening the two-way purge 70 to admit nitrogen, air, or some other purge gas into the module to replace the liquid that is drained from the module through check valve 86, through trap 54B to facility drain/reclaim 56. If the module is designed for sterile processing, then the filter 82 may be 0.2 micron filter to remove microbes from the purge gas. If the module is designed for ultra-clean processing, then the filter 82 may be designed to remove particulate contamination from the purge gas. It is desirable to design the immersion processing module with baffles and other means to insure that the flow of liquid from the inlet to the outlet is approximately plug flow to insure that most of the "reduced concentration" or "spent" ozone-water solution and oxidation or cleaning byproducts are swept from the module and replaced by a "fresh" heated ozone-water solution. An alternative method of insuring that the "reduced concentration" or "spent" ozone zone-water solution and oxidation or cleaning byproducts are removed from the module and replaced by a "fresh" heated ozone-water solution is to fill process the materials with a series of fill, hold, drain, fill, hold, drain cycles. The module may be drained and refilled once the dissolved ozone concentration has fallen to a predetermined level. The solution may be stirred or mixed during the holding period with a high flow recirculation pump, with a stirrer, with ultrasonic or megasonic transducers, or other means known to those skilled in the art. Since the dissolved concentration of the heated ozone-water solution falls more quickly at higher temperatures, optimum hold times will typically be shorter at higher processing temperatures.

Figure 8:
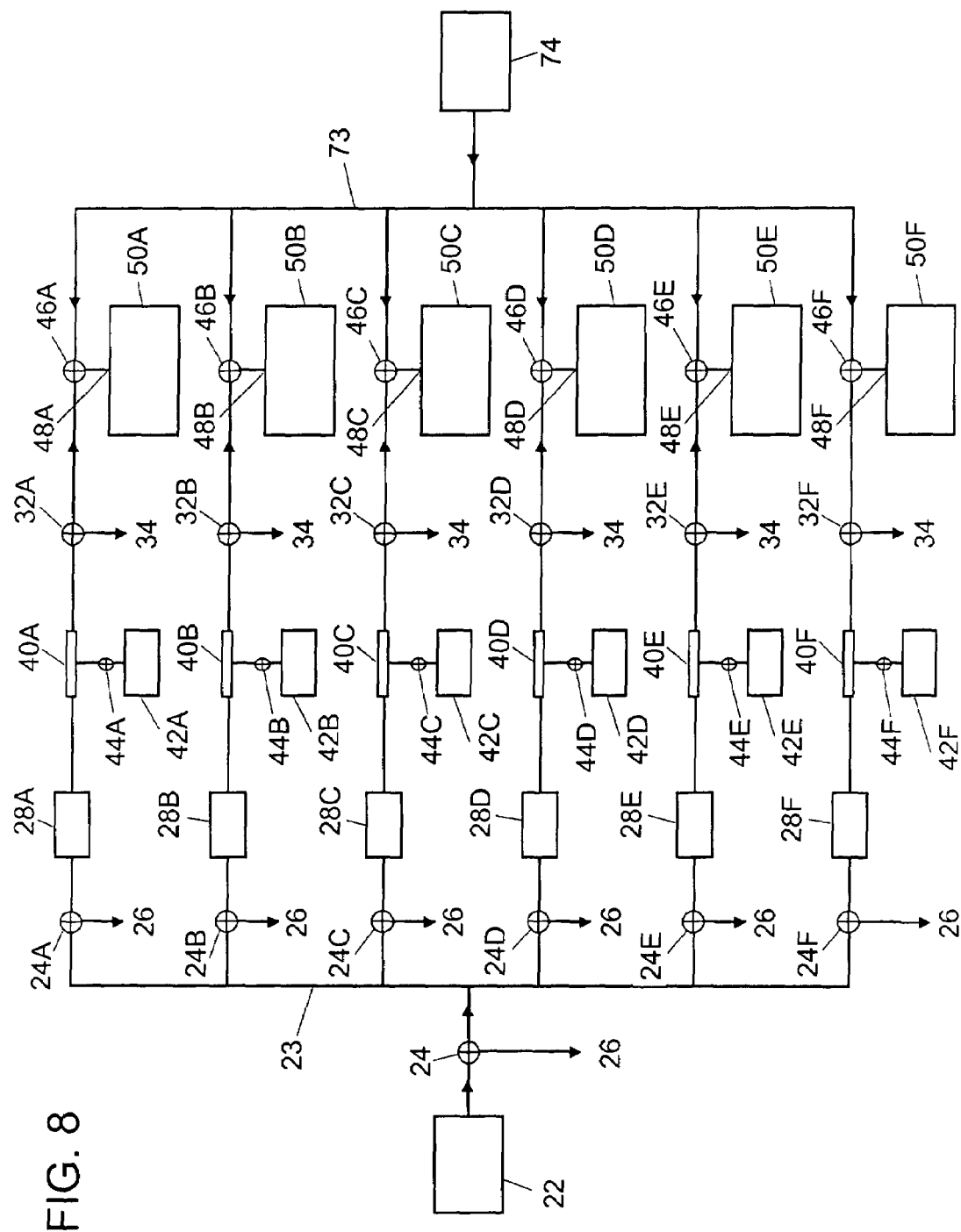
FIG. 8 illustrates a block diagram of a method of processing semiconductor wafers with multiple single-wafer spin processors—multiple point-of-use heater.

High Throughput Materials Processing Method with Multiple Single-Wafer Spin Processors Description—FIG. 8

The spin processing method can be implemented in a high throughput configurations for processing semiconductor wafers and the like. A single wafer processing tool can designed using an industry standard cluster tool geometry with multiple single-wafer process modules. Multiple single wafer spin processing modules may be served by a single ozonated water supply 22. In reference to FIG. 8, an ozonated water supply 22 is connected through a length of tubing to the common input of a three-way valve 24. The one outlet of three-way valve 24 is connected by a length of tubing to a manifold 23. Each of the six outlet ports of the manifold is connected by a length of tubing to each of six three-way valves 24. The three-way valves are labeled 24A, 24B, 24B, 24C, 24D, 24E, 24F. Three-way valve 24A is connected through a length of tubing to the cold process fluid inlet of a heat exchanger 28A. The other outlet of the three-way valve 24A is connected through a length of tubing to the facility drain-reclaim 26. The recirculating heating unit 30 which serves each of the heat exchangers is not shown. The heated process fluid outlet of heat exchanger 28A is connected through a short length of tubing to the inlet of a chemical injector/mixer 40A. The outlet of the injected chemical supply 42A is connected by a length of tubing to the inlet of a two-way valve 44A. The outlet of two-way valve 44A is connected by a length of tubing to the injection port of chemical injector/mixer 40A. The outlet of chemical injector/mixer 40A is connected to the inlet port of three-way valve 32A. The one outlet of three-way valve 32A is connected through a short length of tubing to the etch inlet of a three-way valve etch/rinse valve 46A The other outlet of the three-way valve 32A is connected by a length tubing to the facility drain/reclaim 34. The common outlet of three-way etch/rinse valve 46A is connected through a short length of tubing to the process fluid inlet 48A to a dispense nozzle (not shown) located in a gas tight materials processing module 50A. A rinse water supply 74 is connected by a length of tubing to a manifold 73. Each of the six outlet ports of manifold 73 is connected by a length of tubing to the rinse inlet of each of six three-way valves 46A, 46B, 46C, 46D, 46E, and 46F. Each of the other spin modules 50B, 50C, 50D, 50E, and 50F is connected in the same way. In the preferred embodiment each of the materials processing modules 50 may be fitted with a lid with a gas tight seal (not shown). The sealed materials processing module serves to contain the any ozone gas that is released from solution at the point of application. In the arrangement shown all modules share a single ozonated water supply and a single rinse water supply. Each spin processing module is shown with its own injected chemical supply. In an alternative embodiment, a single injected chemical supply may be used to supply injected chemicals to all modules.

The complete system may have a nitrogen purge supply 68, and each spin processing module will have a dispense nozzle 36, wafer chuck 58, spinner motor 60, drain outlet 52, vent outlet 62, purge gas inlet 72, purge gas two-way valve 70 as shown in FIG. 5 for a single module configuration. Each drain outlet 52 may be connected through a trap 54 to a facility drain 56 for process effluent as shown in FIG. 5 a single module configuration. Each vent outlet may be connected through a catalytic ozone destruction unit 64 to a facility waste gas exhaust vent 66 as shown in FIG. 5. These elements are omitted from FIG. 8 for clarity. In one embodiment, a heat exchanger 28 may be used to increase the temperature of the ozone-water solution at the point-of-use. In another embodiment, a point-of-use water heater 29 may be used in lieu of a heat exchanger.

High Throughput Materials Processing Method with Multiple Single-Wafer Spin Processors—Multiple Heat Exchangers Operation—FIG. 8

The operation of each wafer spin processing module and associated elements is the same as described earlier under FIG. 5. The modules can be operated by a process controller (not shown) to achieve high throughput while sharing the most expensive resource, the ozonated water supply. A typical process sequence for such a tool is shown in Table 13. A single ozone-water supply feeds the three process modules that are in the etch/clean phase at any point in the process cycle. A process controller controls the flow of ozone-water solution, injected chemicals, and DI rinse water to each of the modules by controlling the positions of the control valves. In all the embodiments shown in all the figures the valves may be gas operated or electrically operated solenoid valves so that the valves can be controlled with a central controller. In this example the etch time is set to 60 seconds and the rinse, dry, and load/unload times are each set to 20 seconds. The throughput for the example shown is 180 wafers/hour. During any 20 second period, 3 modules at most are in an etch/clean cycle, 1 module at most is in the DI water rinse cycle, and 1 module at most is in the Spin Dry Cycle. If for example the ozonated water supply flow rate required for each module during the etch/clean cycle is 3.33 liters per minute at a given dissolved ozone concentration, then the entire cluster of 6 modules may be supplied by a single ozonated water supply with a flow capacity of 10 liters per minute. The example operating sequence in Table 17 shows the operation during steady state when three process modules are etching, one process module is rinsing, one process module is drying, and one process module is being unloaded, and loaded with the next wafer to be processed. During the period when each of the modules of the cluster are loaded in succession for the first time at the beginning of a run of wafer, first only one processor is in the etch mode, then two processors are in the etch mode, then three processors are in the etch mode. There is a analogous transient period when each of the modules of the cluster are unloaded in succession at the end of a run of wafers. At the end of a run of wafers, three processors are in the etch mode, then two processors are in the etch mode, then one processor is in the etch mode. During the period in which only one module or only two modules are in the etch mode, only 3.33 L/min or only 6.66 L/min of ozonated water is being used for etching for this example. In one embodiment the total ozonated flow can be held constant (~10.0 L/min for this example) either by setting the three-way valves 24, or by setting the three-way valves 32 to direct to the facility waste/reclaim 34 the ozonated water not needed for etching. This approach maintains a steady state water flow through the ozone-gas-water contactor and provides a simple method to maintaining a stable dissolved ozone concentration. This approach is sample. An alternative method is to reduce the flow rate of ozonated water supplied by the ozonated water supply 22 while maintaining the same supplied dissolved ozone concentration. This requires that the ozonated water supply include a controller for maintaining the same dissolved ozone concentration at different flow rates less than the maximum flow rate for that concentration. This approach is more challenging because it would require that the controller be able to quickly stabilize the concentration in about 2 seconds or less, as the flow rate was incremented in steps at the start of the process run, and decremented in steps at the end of a process run.

TABLE 17

Operation of Cluster Tool with Six Process Modules - Example

| Module | 20 sec | 20 sec | 20 sec | 20 sec | 20 sec | 20 sec | 20 sec | 20 sec | 20 sec | 20 sec | 20 sec | 20 sec | 20 sec | 20 sec | 20 sec | 20 sec | 20 sec | 20 sec |
|---|---|---|---|---|---|---|---|---|---|---|---|---|---|---|---|---|---|---|
| #A | L/U | E | E | E | R | D | L/U | E | E | E | R | D | L/U | E | E | E | R | D |
| #B | D | L/U | E | E | E | R | D | L/U | E | E | E | R | D | L/U | E | E | E | R |
| #C | R | D | L/U | E | E | E | R | D | L/U | E | E | E | R | D | L/U | E | E | E |
| #D | E | R | D | L/U | E | E | E | R | D | L/U | E | E | E | R | D | L/U | E | E |
| #E | E | E | R | D | L/U | E | E | E | R | D | L/U | E | E | E | R | D | L/U | E |
| #F | E | E | E | R | D | L/U | E | E | E | R | D | L/U | E | E | E | R | D | L/U |
| E | 3 | 3 | 3 | 3 | 3 | 3 | 3 | 3 | 3 | 3 | 3 | 3 | 3 | 3 | 3 | 3 | 3 | 3 |
| R | 1 | 1 | 1 | 1 | 1 | 1 | 1 | 1 | 1 | 1 | 1 | 1 | 1 | 1 | 1 | 1 | 1 | 1 |
| D | 1 | 1 | 1 | 1 | 1 | 1 | 1 | 1 | 1 | 1 | 1 | 1 | 1 | 1 | 1 | 1 | 1 | 1 |
| L/U | 1 | 1 | 1 | 1 | 1 | 1 | 1 | 1 | 1 | 1 | 1 | 1 | 1 | 1 | 1 | 1 | 1 | 1 |

Figure 9:
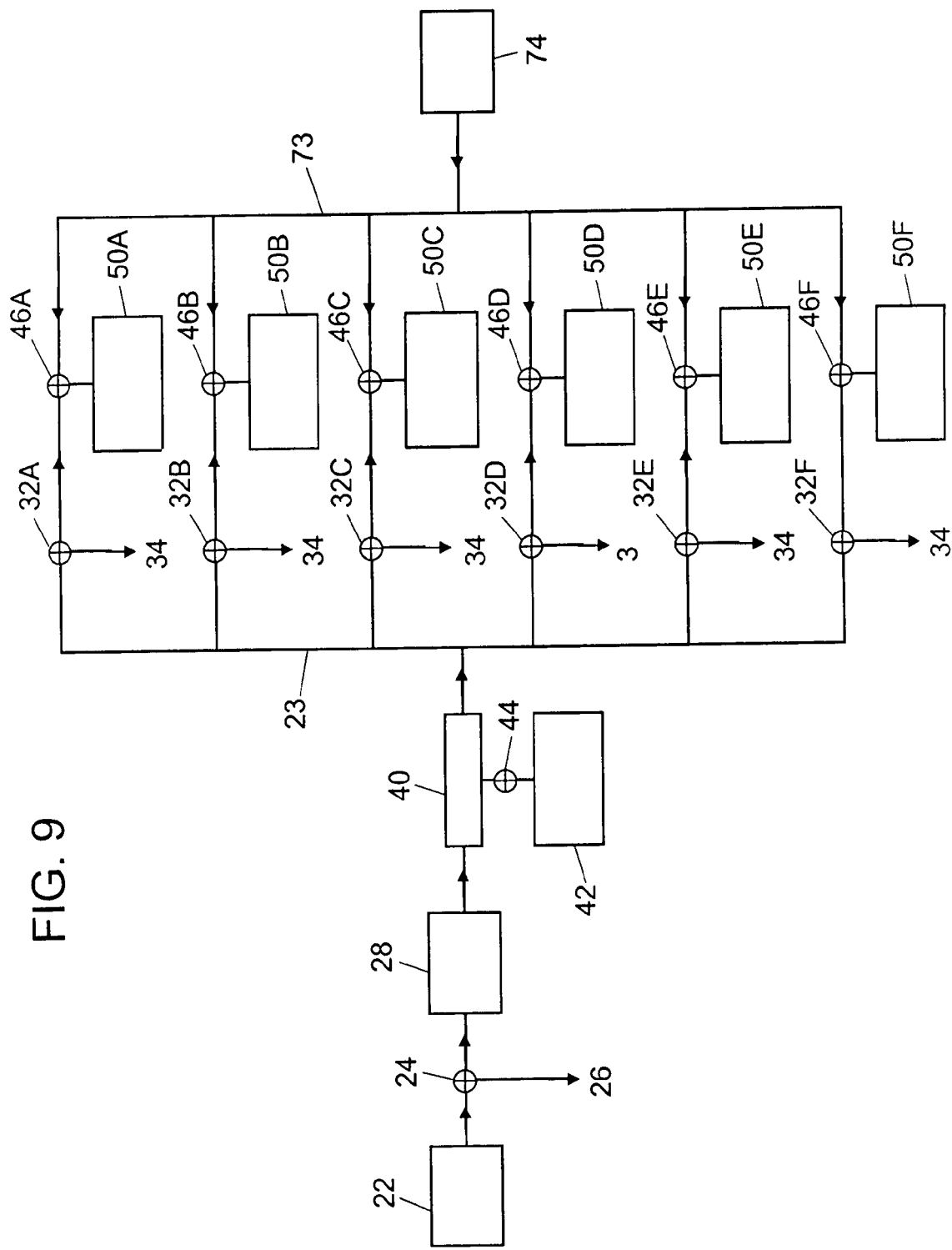
FIG. 9 illustrates a block diagram of a method of processing semiconductor wafers with multiple single-wafer spin processors—single point-of-use heater.

E—Etch/Clean Cycle
R—DI Water Rinse Cycle
D—Spin Dry Cycle
L/U—Load/Unload Wafer w/ Robot Cluster Throughput for Example: 30 wafers/hour/spinner×6 spinners=180 wafers/hour High Throughput Materials Processing Method with Mulitiple Single-Wafer Spin Processors—Single Shared Heat Exchanger Description—FIG. 9

In reference to FIG. 9, an alternative embodiment may use a single point-of-use heater (heater exchanger 28 or point-of-use heater 29) and single chemical injector/mixer 40 to serve multiple spin processing modules. Since the flow rate of the ozone-water solution through the point-of-use heater is higher, the heat input required to increase the temperature from T1 to T2 is higher. The heat exchanger may be larger and the volume of the heat exchanger may be larger. The residence time in the heater and connecting tubing may be kept approximately the same if the volume is increased by the same factor as the flow rate. In the example shown in Table 17 above, the flow rate through the exchanger and injector/mixer will be up to 3 times higher and the power input required will be up to 3 times higher.

Operation—FIG. 9

The operation of the embodiment shown in FIG. 9 is otherwise similar to that described under FIG. 8 and FIG. 5. In the embodiment using the single heat exchanger, the flow of heated ozone-water solution is directed to the three spin processing modules that are in the etch phase of the cycle. During the period when each of the modules of the cluster either are loaded in succession for the first time at the beginning of a run of wafers, or are loaded in succession for the last time at the end of a run of wafers, fewer than three modules may be in the etch mode at one time as described under FIG. 8. In one embodiment the total ozonated flow can be held constant (~10.0 L/min for this example) by setting the three-way valves 32 to direct to the facility waste/reclaim 34 the ozonated water not needed for etching. This approach maintains an approximately steady-state water flow through the ozone-gas-water contactor and provides a simple method to maintaining a stable dissolved ozone concentration as described under FIG. 8. It also maintains a constant flow rate through the shared heat exchanger 28 and maintains a constant dispense temperature. This is again a simple embodiment. An alternative method is to reduce the flow rate of ozonated water supplied by the ozonated water supply 22 while maintaining the same supplied dissolved ozone concentration and same dispense temperature. This embodiment requires that the ozonated water supply include a controller for maintaining the same dissolved ozone concentration at different flow rates as discussed under FIG. 8. This also requires the use of a point-of-use heater 29 with the means to maintain a constant dispense temperature at different dispense flow rates.

Figure 10:
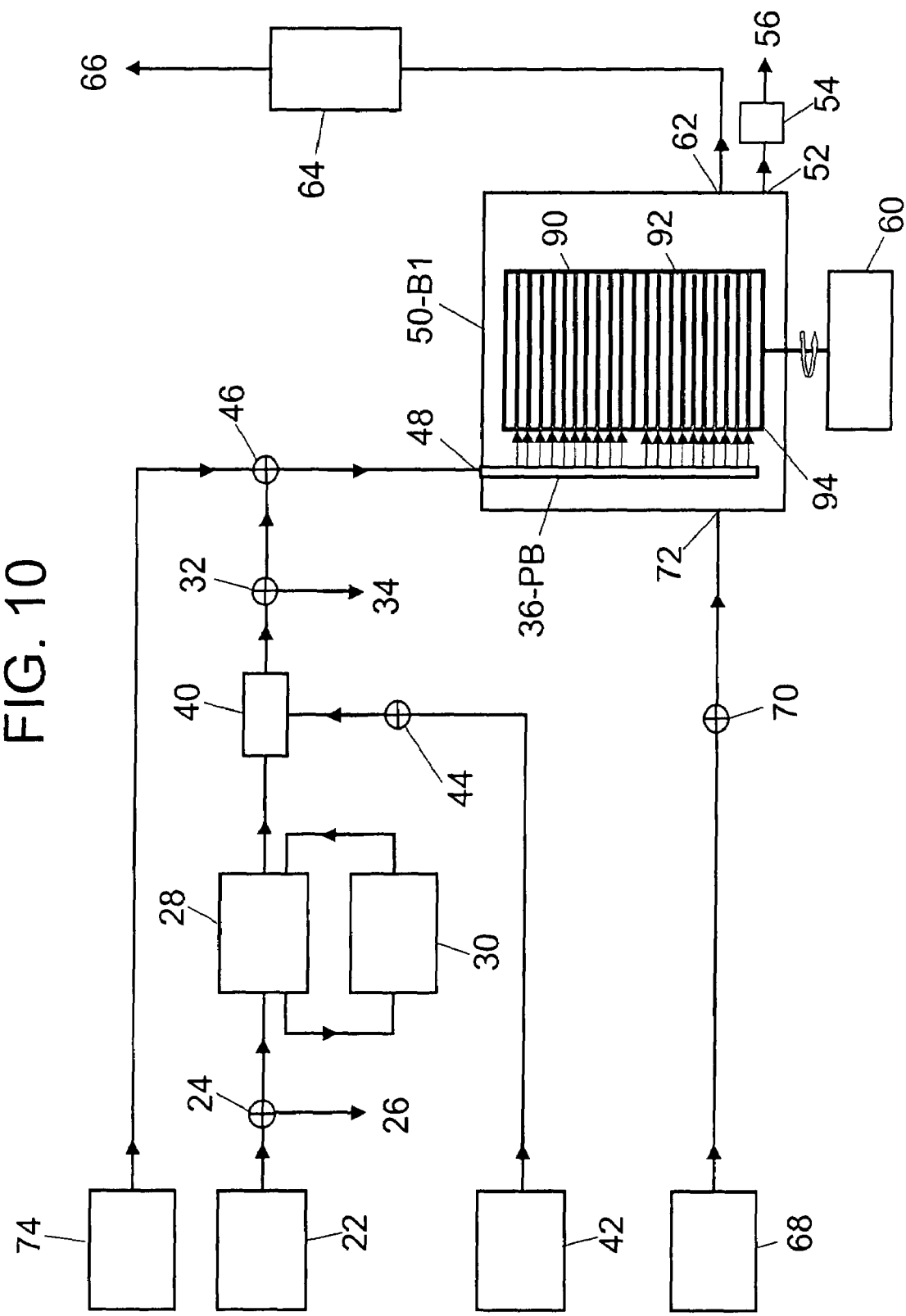
FIG. 10 illustrates a block diagram of a method of processing a batch (one or more cassettes) of semiconductor wafers with an on-axis batch spin processor.

High Throughput Materials Processing Method with an On-Axis Wafer-Batch Spin Processor Description—FIG. 10

The spin processing method can be implemented in a high throughput configuration for processing semiconductor wafers and the like. A batch wafer processing tool can designed using an on-axis batch spin processor designed to process two to four cassettes of wafers or substrates at one time. In reference to FIG. 10, a batch spin module 50-B1 for processing two cassettes of wafers in an on-axis spin configuration may be served by a source of ozonated water, rinse water, purge gas, drain, and vent connections using the same configuration as that described under FIG. 5 for a single wafer spin processor. In the case of the on-axis wafer-batch spin processor, the outlet of the three-way etch rinse valve 46 is connected by a short length of tubing through a module inlet 48 to a perimeter spray bar 36-PB. Two 25 wafer cassettes 90 and 92 are mounted in a wafer cassette chuck 94. The wafer cassette chuck 94 is connected by a shaft or other means to a spin motor 60. The spin motor may be set to a particular acceleration rate, spin RPM, spin duration, and deceleration rate under microprocessor control.

Operation—FIG. 10

In reference to FIG. 10, the operation of an on-axis batch spin processor designed to process two to four cassettes of wafers or substrates at one time is similar in most respects to the operation of a single wafer spin processor described under FIG. 5. A batch spin processor typically operates at a lower RPM and lower flow rate per wafer than a single wafer spin processor. The RPM for a batch spinner is typically in the range of 500 to 1500 RPM. The total etch chemistry flow rate for a batch wafer spinner is typically in the range of 10 to 20 liters/minute. The lower RPM and lower flow rates will yield a lower mass transport rate and lower etch rate. The temperature at which the etch rate will become mass transport limited will be lower since the mass transport rate is lower as discussed earlier.

In the etch mode a heated ozone water solution flows from the outlet of three-way valve through an inlet 48 in the module, to the perimeter spray bar 36-PB. The heated ozone-water solution is dispensed from multiple positions along the length of the spray bar and contacts the surfaces of the wafers held in the wafer cassettes which are spinning on-axis.

Figure 11:
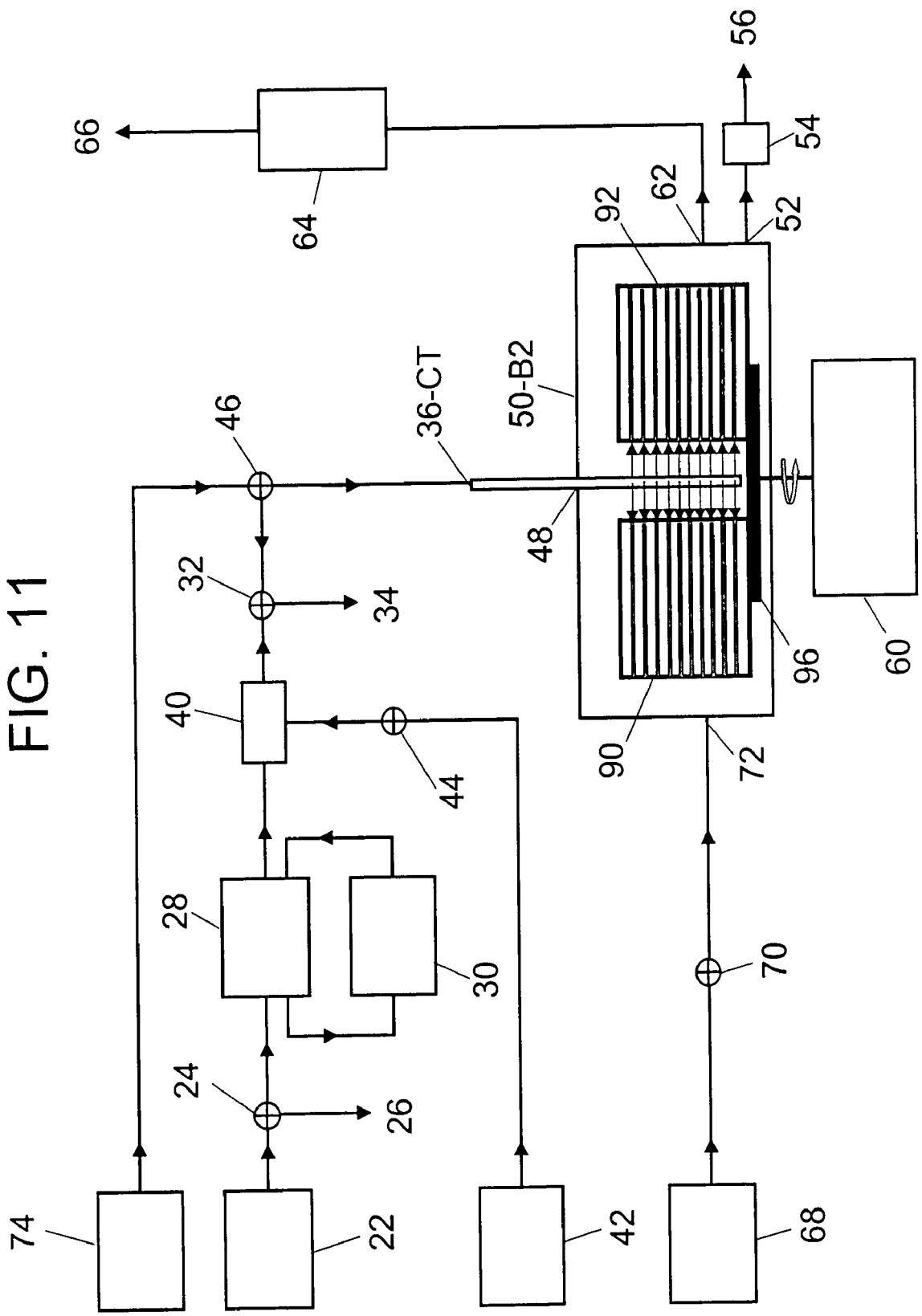
FIG. 11 illustrates a block diagram of a method of processing a batch (one or more cassettes) of semiconductor wafers with an off-axis batch spin processor.

High Throughput Materials Processing Method with an Off-Axis Wafer-Batch Spin Processor Description—FIG. 11

The spin processing method can be implemented in a high throughput configuration for processing semiconductor wafers and the like. A batch wafer processing tool can designed using an off-axis batch spin processor designed to process two to four cassettes of wafers or substrates at one time. In reference to FIG. 11, a batch spin module 50-B2 for processing two cassettes of wafers in an off-axis spin configuration may be served by a source of ozonated water, rinse water, purge gas, drain, and vent connections using the same configuration as that described under FIG. 5 for a single wafer spin processor. In the case of the off-axis wafer-batch spin processor, the outlet of the three-way etch rinse valve 46 is connected by a short length of tubing through a module inlet 48 to a center spray tower 36-CT. Two 25 wafer cassettes 90 and 92 are mounted in a wafer cassette chuck 96. The wafer cassette chuck 96 is connected by a shaft or other means to a spin motor 60. The spin motor may be set to a particular acceleration rate, spin RPM, spin duration, and deceleration rate under microprocessor control.

Operation—FIG. 11

In reference to FIG. 11, the operation of an off-axis batch spin processor designed to process two to four cassettes of wafers or substrates at one time is similar in most respects to the operation of a single wafer spin processor described under FIG. 5. A batch spin processor typically operates at a lower RPM and lower flow rate per wafer than a single wafer spin processor. The RPM for a batch spinner is typically in the range of 500 to 1500 RPM. The total etch chemistry flow rate for a batch wafer spinner is typically in the range of 10 to 20 liters/minute. The lower RPM and lower flow rates will yield a lower mass transport rate and lower etch rate. The temperature at which the etch rate will become mass transport limited will be lower since the mass transport rate is lower as discussed earlier.

In the etch mode a heated ozone water solution flows from the outlet of three-way valve through an inlet 48 in the module, to the center spray tower 36-CT. The heated ozone-water solution is dispensed from multiple positions along the length of the spray tower and contacts the surfaces of the wafers held in the wafer cassettes which are spinning off-axis. The ozone-water solution that moves across the wafer, entering at an edge near the spray tower and exiting at an edge far from the spray tower. The dissolved ozone concentration falls as the solution moves across the wafer surface because the ozone in solution is depleted by reaction with the material on the wafer surface. In a standard off-axis batch processor configuration this can yields a relatively high etch rate at the wafer leading edge and a relatively low etch rate at the wafer trailing edge. A preferred embodiment for off-axis wafer processing not only rotates the wafer cassettes around an axis some distance form the wafer center, but also slowly rotates the wafer cassettes on axis so that all edges of the wafers are placed in the leading edge position for approximately the same time during the wafer processing cycle. This can be accomplished by a drive gear or other device for slowly rotating the wafer cassettes about the center of the wafers as the wafer cassettes are rotated off axis.

$2^{ND}$ GROUP: Heat Applied at the Point of Application (FIG. 12 Through FIG. 15)

A second method for oxidizing materials at high speed using a solution of ozone gas dissolved in water comprising the steps of dissolving (relatively high concentration) ozone gas in water at a relatively low predetermined temperature T1 to form an ozone-water solution (with a relatively high dissolved ozone concentration), applying the cold ozone-water solution to said materials while heating said materials and said ozone-water solution at the point of application to quickly increase said material temperature and said solution temperature to a predetermined higher temperature T2>T1 where preferrably T2−T1>5 degree C. The second method for oxidizing materials at high speed may additionally includes a means for injecting and mixing additional chemicals into the ozone-water solution just upstream of the point of application of the ozone-water solution to the materials to be oxidized. A number of preferred embodiments are illustrated in FIG. 12 to FIG. 16.

Figure 12:
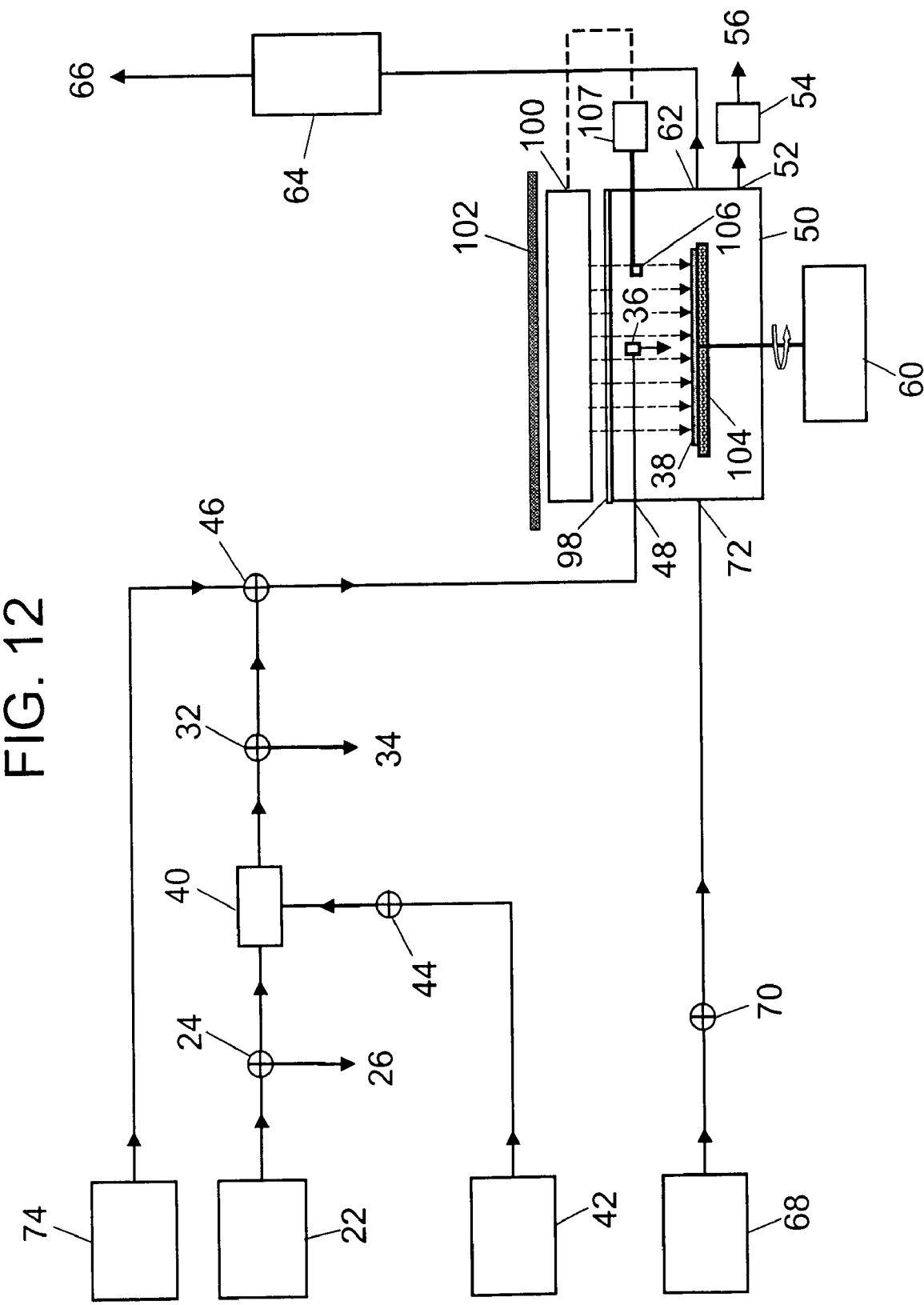
FIG. 12 illustrates a functional block diagram of a method of processing materials: A cold ozone-water solution at temperature T1 is applied to a material to be processed while the material to be processed and the ozone-water solution is heated to temperature T2>T1 at the point of application using radiant heating—heated from top surface.

Material to be Processed and Ozone-Water Solution Heated at the Point of Application—Top Surface Radiant Heating Description—FIG. 12

This embodiment is very similar to the embodiment shown in FIG. 5 except that the ozone ozone water solution is not heated upstream of the point-of-use. Instead, the material to be processed and the ozone-water solution is heated at the point of application. Accordingly, the point-of-use water heater is omitted and point of application heater is added. With reference to FIG. 12, an ozonated water supply 22 is connected through a length of tubing to the common input of a three-way valve 24. The one outlet of three-way valve 24 is connected through a length of tubing to the process fluid inlet of chemical injector/mixer 40. The other outlet of three-way valve 24 is connected through a length of tubing to the facility drain-reclaim 26 for the ozone-water solution. The outlet of an injected chemical supply 42 is connected to the inlet of two-way valve 44. The outlet of valve 44 is connected to the chemical injection port of chemical injector/mixer 40. The outlet of chemical injector/mixer 40 is connected by a short length of tubing to the common inlet port of three-way valve 32. The one outlet of three-way valve 32 is connected through a short length to one inlet of a three-way valve etch/rinse valve 46. The common outlet of three-way etch/rinse valve 46 is connected through a short length of tubing to the process fluid inlet 48 to a dispense nozzle 36 located in a gas tight materials processing module 50. The materials processing module 50 is fitted with a lid with a gas tight seal with a quartz window 98 in the lid with good infrared transmission. The module purge gas connection 72, the module drain connection 52, and module vent connections 62 are the same as described previously. A high power radiant heat source 100 such as a quartz halogen lamp array is positioned to illuminate the surface of the wafer or substrate 38 which is mounted on a spinner chuck 104. We can calculate an estimate of the maximum amount of power required to heat the material and the ozone water solution by assuming that we must increase the temperature of the full flow of ozone water solution as it passes over the wafer and we must heat the full volume of the wafer. The power required increase the water temperature by a given amount for a given flow rate has been presented in Table 5 of the discussion under FIG. 1. The power required to increase the temperature of an ozone water solution flowing at 2.7 L/min by 50 degree C. is approximately 10 Kwatts. A small amount of additional energy will be required to increase the wafer temperature by the same amount. The amount of energy can be readily calculated from the mass and heat capacity of the wafer or substrate. If in practice the only the surface of the wafer or only a thin layer of the ozone-water solution at the wafer-solution interface is heated, then the power requirements will be lower. Also, if the ozone-water solution flow rate is reduced, the power requirement will be lower. The methods of heating of wafers and substrates with quartz halogen lamp arrays are well developed and well known to those skilled in the art in the area of single wafer rapid thermal processing (RTP). A typical RTP lamp array for 200 mm diameter wafers has a power input of about 50 Kwatts. Typically about 40 percent of the lamp input power (20 Kwatts) is deposited in the substrate in RTP applications. The RTP lamp power is well suited to this new application. A gold coated infrared reflective surface 102 is place above the radiant heat source 100 to reflect the visible and infrared radiation back to the substrate. A gold coated infrared reflective surface is placed on the surface of the spinner chuck to to reflect the visible and infrared radiation that may pass through the substrate back though the substrate toward the infrared reflective surface 102. The length of tubing leading to the dispense nozzle 36 may be insulated and protected with an infrared reflective surface like gold to prevent the tubing and dispense nozzle from overheating. A non-contact temperature sensor 106 is positioned to read the temperature of the substrate. The measurement of the temperature of spinning silicon wafers is well known to those skilled in the art in the area of single wafer rapid thermal processing (RTP).

Operation—FIG. 12

A cold ozone-water solution at temperature T1 is applied to a material to be processed while the material to be processed and the ozone-water solution is heated to temperature T2>T1 at the point of application using radiant heating from the top surface. In one embodiment the ozone water solution is dispensed onto the wafer surface with a center dispense nozzle as discussed earlier under FIG. 5. The cold ozone-water solution that flows radially outward to the edge of the spinning wafer will cool the wafer when the radiant heat source is off. Temperature sensor 106 is connected to controller (not shown) which adjusts the heat output of the radiant heat source 100 to maintain a preset temperature (50 degree C. for example). The use of feedback control to control of the temperature of wafers and other substrates heated with quartz halogen radiant heating sources is also well known to those skilled in the art in the area of single wafer rapid thermal processing (RTP). When the radiant heat source is turned on to quickly increase the temperature of the substrate the substrate will be heated by absorption of radiant energy. The ozone-water solution that passes across the surface of the wafer or substrate in a thin layer will not only absorb some radiant energy, but will be heated by convection as the water passes over the heated substrate and energy is transported from the heated substrate to the chilled ozone-water solution. Since both velocity and thickness of the water that moves radially outward varies with radius, both the rate of energy loss by water cooling and the rate of energy gain by radiant heating and absorption may have a radial dependence. Accordingly, the radiant heat source may be designed to deposit a different amount of energy into different radial zones to achieve approximately the same temperature over the entire substrate surface. The use of concentric zone radiant heating with multiple temperature sensors to maintain a constant temperature over the entire substrate surface is again well known to those skilled in the art in the area of single wafer rapid thermal processing (RTP).

The ozone-water solution will not be heated until the ozone-water solution is applied to the surface of the substrate. Accordingly, the time delay between the increase in temperature of the ozone-water solution and the application of the solution to the surface of the material to be processed will be essentially zero, the rate at which the ozone gas leaves the solution at the substrate should not differ significantly from the case in which the substrate is not heated but is at the same temperature as the ozone-water solution. This type of embodiment will be particularly helpful in preserving a high dissolved ozone concentration in embodiments in which the optimum processing temperature is higher because the concentration decays in shorter time at higher temperatures as discussed earlier. A solution application means which achieves a higher mass transport coefficient M has a higher maximum optimum processing temperature.

Figure 13:
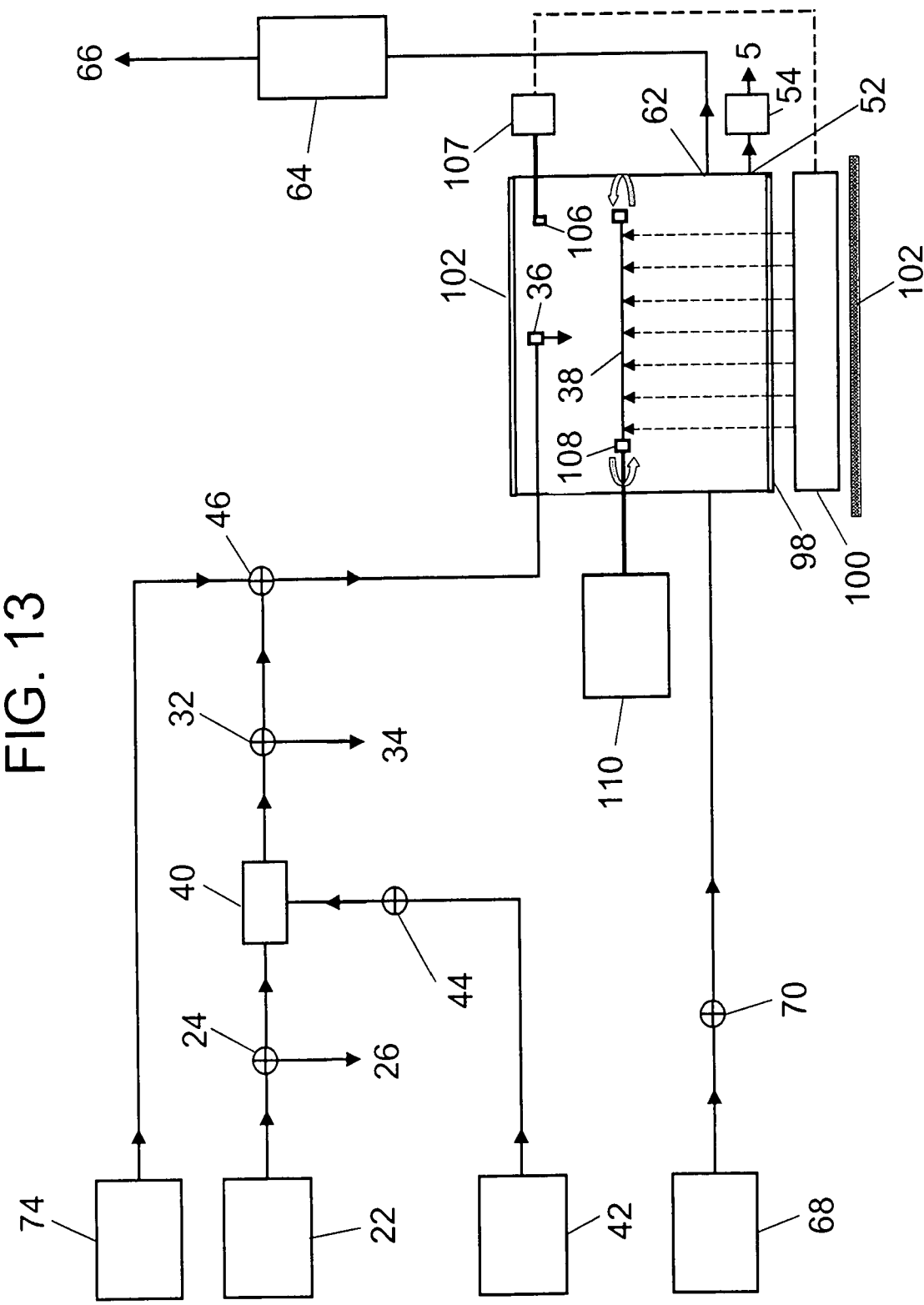
FIG. 13 illustrates a functional block diagram of a method of processing materials: A cold ozone-water solution at temperature T1 is applied to a material to be processed while the material to be processed and the ozone-water solution is heated to temperature T2>T1 at the point of application using radiant heating—heated from bottom surface.

Material to be Processed and Ozone-Water Solution Heated at the Point of Application—Bottom Surface Radiant Heating Description—FIG. 13

In reference to FIG. 13, the structure of this embodiment is similar to that described under 12 except that the wafer or substrate is mounted on an edge-driven open-bottom spinner-chuck 108, and the wafer is heated from the bottom. A radiant heat source 100 illuminates the bottom of the wafer through a quartz window 98 in the bottom of the spinner module. An infrared reflective surface 102 is place behind the radiant heat source and a second infrared reflective surface 102 is placed above the dispense nozzle 36.

Operation—FIG. 13

In reference to FIG. 13, the operation of to this embodiment is the similar to that described under 12 except that the wafer or substrate is heated with a radiant heat source 100 which illuminates the bottom of the wafer. This configuration may be more convenient to implement in some applications.

Figure 14:
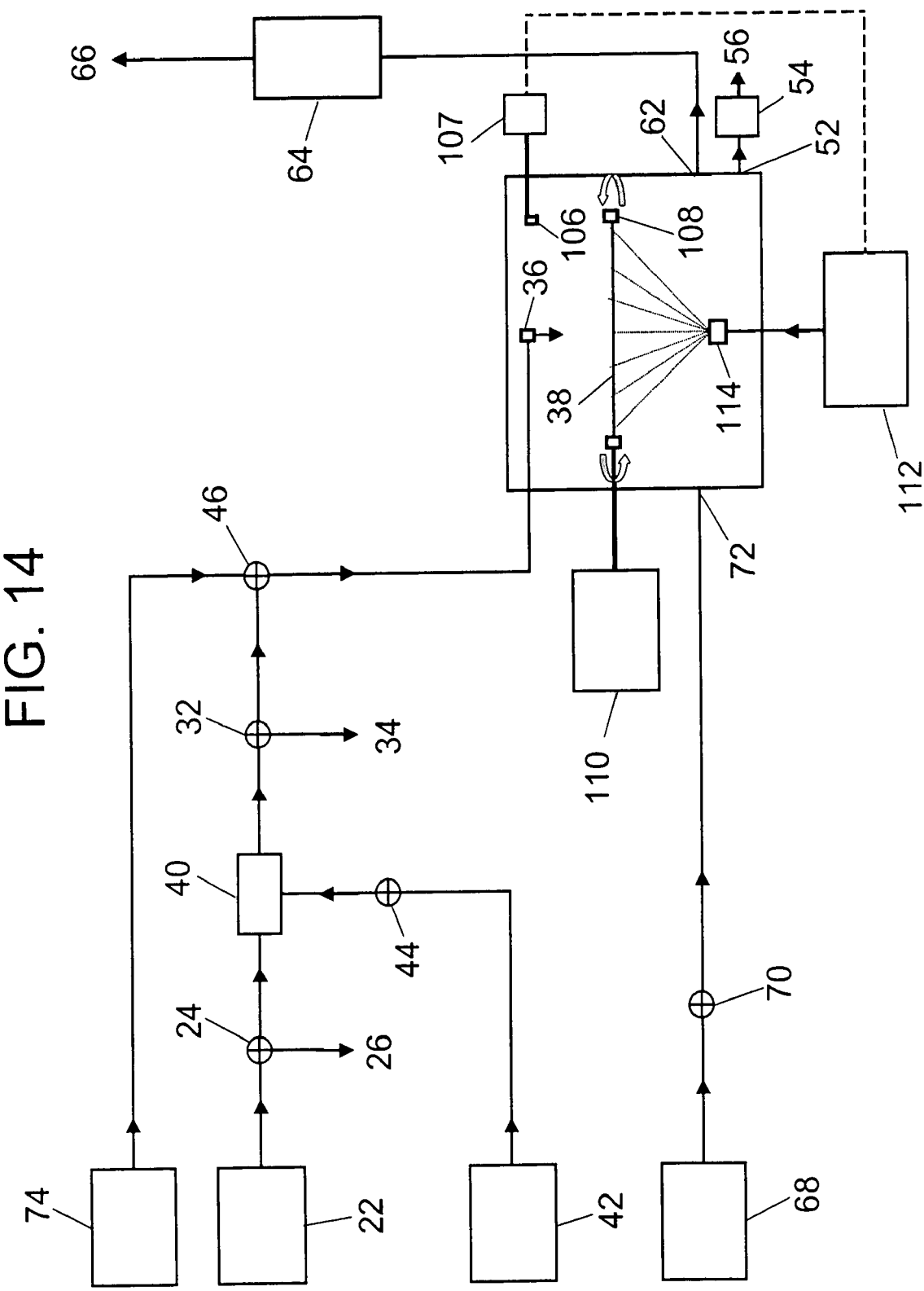
FIG. 14 illustrates a functional block diagram of a method of processing materials: A cold ozone-water solution at temperature T1 is applied to a material to be processed while the material to be processed and the ozone-water solution is heated to temperature T2>T1 at the point of application using a convection heating—heated from bottom surface.

Material to be Processed and Ozone-Water Solution Heated at the Point of Application—Bottom Surface Convection Heating Description—FIG. 14

In reference to FIG. 14, the structure of this embodiment is similar to that described under 13 except that wafer is heated from the bottom convectively. The substrate is mounted on an edge-driven open-bottom spinner-chuck 108. A source of heated fluid 112 is dispensed from a nozzle 114 to transfer heat to the bottom of the wafer. The heated fluid may be a liquid such as hot water or a hot gas such as nitrogen. The heated fluid may be produced by passing the fluid through a point-of-use heater.

Operation—FIG. 14

In reference to FIG. 14, a cold ozone-water solution at temperature T1 is applied to a wafer or substrate 38 to be processed with nozzle 114 while the material to be processed and the ozone-water solution is heated to temperature T2>T1 at the point of application through the use of a heated fluid at a temperature greater than T2 directed at the bottom of the substrate with a nozzle 114. The rate at which the substrate can be heated is determined by the net rate of energy gain. The net energy gain is the energy that is transferred to the wafer from the heated fluid stream incident upon the bottom of the substrate minus the energy lost from the wafer to the cooled ozone water stream incident upon the top of the substrate.

Figure 15:
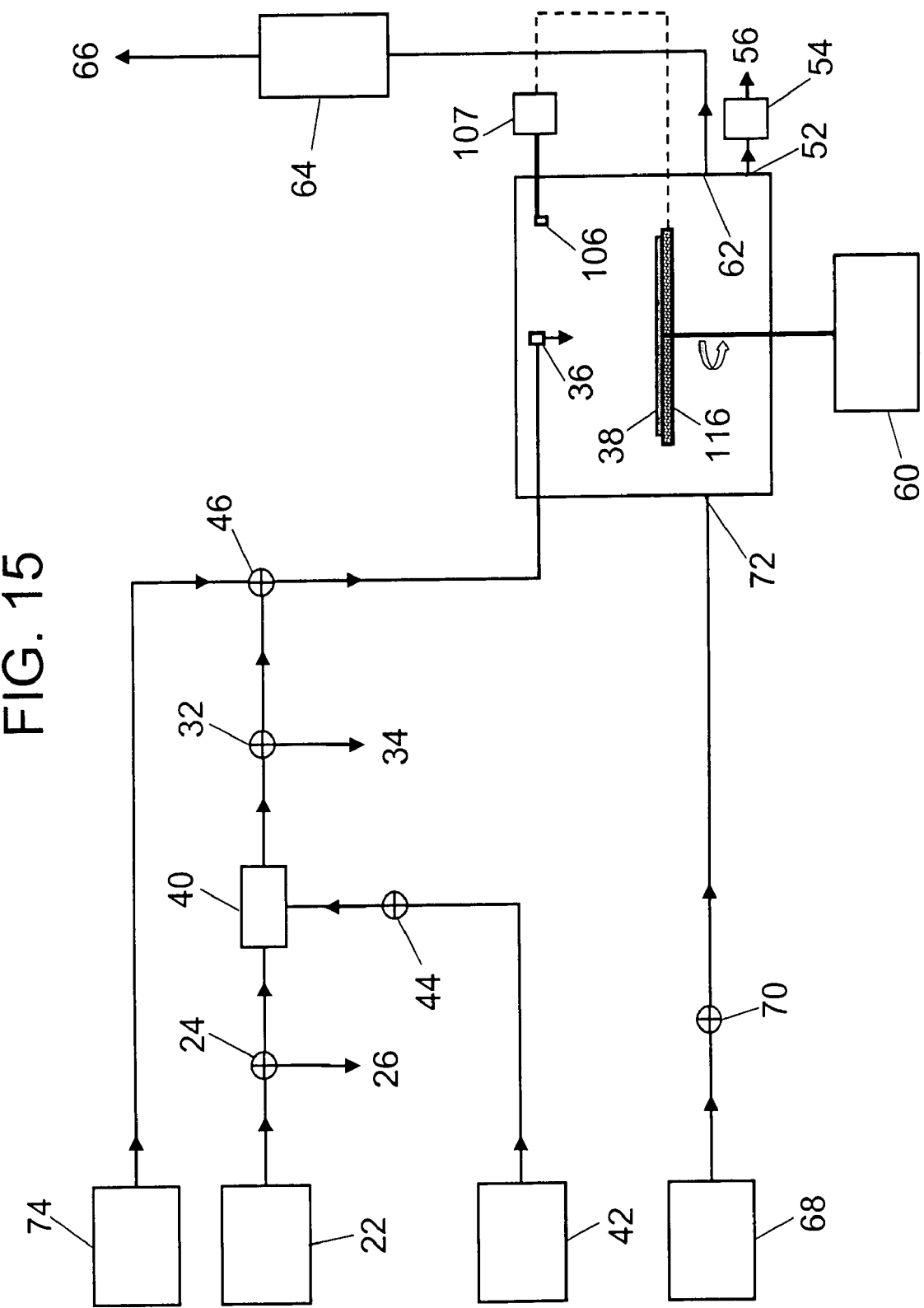
FIG. 15 illustrates a functional block diagram of a method of processing materials: A cold ozone-water solution at temperature T1 is applied to a material to be processed while the material to be processed and the ozone-water solution is heated to temperature T2>T1 at the point of application using conduction heating—heated from bottom surface.

Material to be Processed and Ozone-Water Solution Heated at the Point of Application—Bottom Surface Conduction and Convection Heating Description—FIG. 15

The structure is similar to that described under FIG. 14 except the wafer is mounted on a heated spinning wafer chuck 116 which is driven by spinner motor 60. In reference to FIG. 15, a wafer or substrate 38 is mounted on a heated spinning wafer chuck 116. A non-contact temperature sensor is positioned to read the temperature of the top surface of the substrate. The temperature sensor 106 is connected to a controller. The controller adjusts the amount of energy transferred to the wafer by the heated chuck by adjusting the temperature of the chuck surface.

Operation—FIG. 15

A cold ozone-water solution at temperature T1 is applied to a material to be processed while the material to be processed and the ozone-water solution is heated to temperature T2>T1 at the point of application using a heated chuck in contact with or close proximity to the bottom side of the wafer to heat the wafer.

The embodiments shown in FIG. 12 and FIG. 13 are usually preferred over those shown in FIG. 14 and FIG. 15 because they are based upon a well developed technology and because they can transfer the most power to the wafer or substrate and thereby achieve very fast heating rates. The embodiment shown in FIG. 15 may be lowest cost. However, the embodiment in FIG. 15 may not be able to transfer sufficient energy to the substrate to overcome the energy loss to the chilled ozone-water solution. This heating embodiment may be capable of providing sufficient energy transfer when used in an application for which the flow rate of the chilled ozone-water solution to the substrate is very low.

Material to be Processed and Ozone-Water Mist Solution Heated at the Point of Application—Top Surface Radiant Heating This embodiment differs from all the embodiments presented in FIG. 1 to FIG. 15 in an important respect. In this embodiment a chilled ozone-water mist solution mixed with ozone gas is applied to the surface of a spinning wafer or substrate. This embodiment has the potential to achieve higher removal rates than prior art moist ozone gas methods. The dissolved ozone concentration in the chilled ozone-water mist has the potential to be higher than that which can be produced at the higher temperatures, 50 to 95 degree C., employed in prior art moist ozone gas methods. This embodiment may be able to achieve relatively high removal rates at the low water flow rates usually associated with prior art moist ozone gas organic removal methods.

Figure 16:
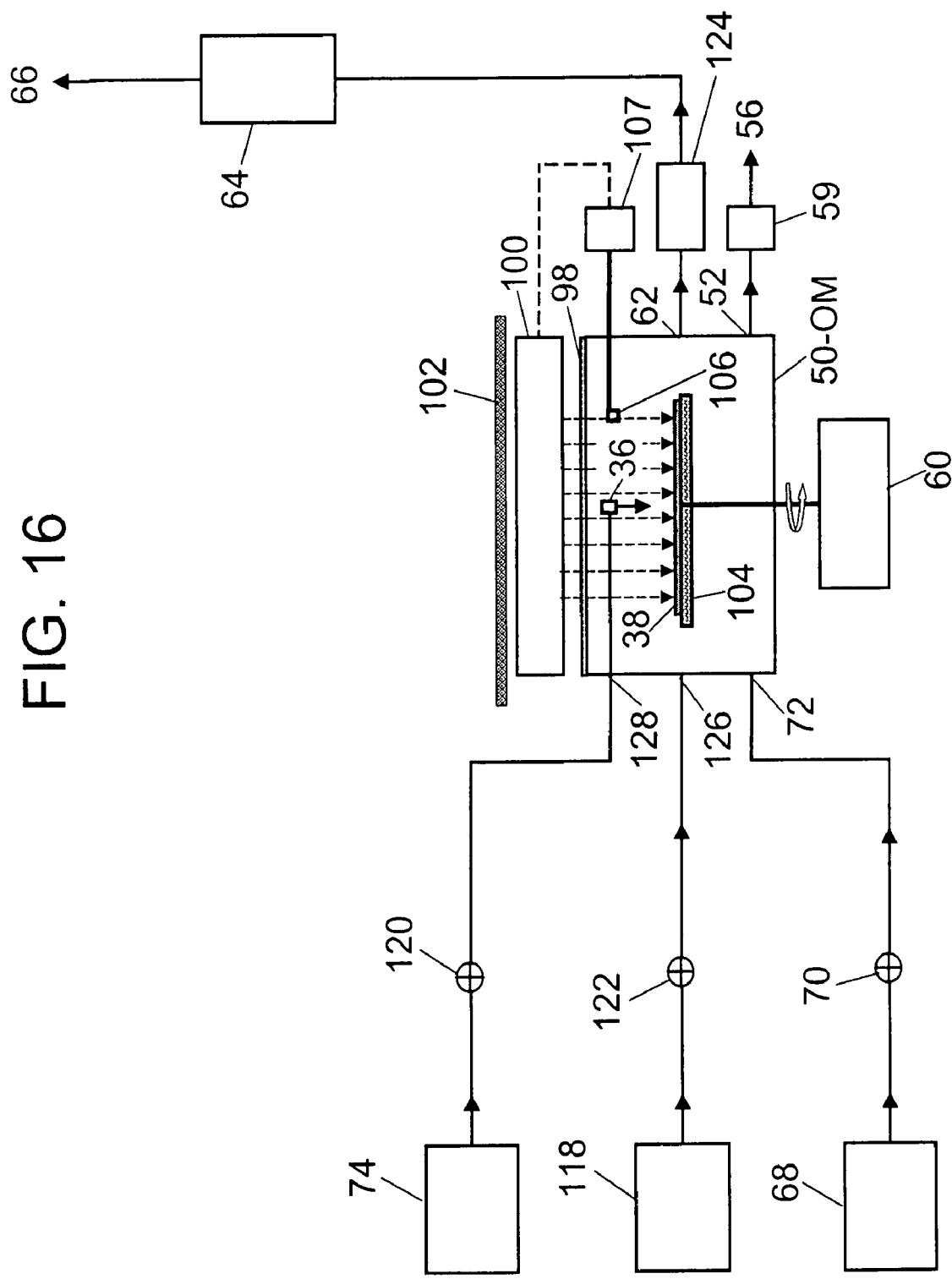
FIG. 16 illustrates a functional block diagram of a method of processing materials: A cold ozone-water mist solution at temperature T1 mixed with ozone gas, is applied to a material to be processed while the material to be processed and the ozone-water mist solution is heated to temperature T2>T1 at the point of application using radiant heating—heated from top surface.

Description—FIG. 16

In reference to FIG. 16, a ozonated water mist/ozone gas supply 118 (detail described in FIG. 19) connected by a short large diameter (approximately 20 cm long, 10 cm diameter) length of tubing to a gate valve 122 to a process fluid inlet 126 in the materials processing module 50-OM. The ozone gas/ozonated water mist outlet 62 of the materials processing module is connected by a short length (~10 cm long, ~10 cm diameter) of tubing to a mist eliminator 124. The outlet of mist eliminator 124 is connected to ozone catalytic destruction unit 64. The outlet of the ozone catalytic destruction unit 64 is connected to facility exhaust vent inlet 66. The liquid drain outlet 52 of the process module 50-OM is connected by a length of tubing through a trap 59 to the facility drain/reclaim inlet 56 for process effluent. A purge gas supply 68 is connected by length of tubing through a two way valve 70 to a purge gas inlet 72 in the process module. A wafer or substrate is mounted on a wafer chuck 104. The wafer chuck is attached to a spinner motor 60. The wafer chuck 104 has an infrared reflective surface to prevent heating of the chuck by the radiant heat source. The process module 50-OM is fitted with a quartz window 98. A radiant heat source 100 and Infrared reflective surface 102 is positioned to illuminate the wafer surface as described under FIG. 12. A non-contact temperature sensor 106 is positioned to read the temperature of the wafer as described under FIG. 12. A rinse water supply 74 is connected by a length of tubing through a two-way valve 120, through the rinse water inlet 128 in the process module to a rinse water dispense nozzle 36 positioned to dispense rinse water on the wafer surface.

Operation—FIG. 16

In reference to FIG. 16, a cold ozone-water mist solution at temperature T1 mixed with ozone gas, is applied to a material to be processed while the material to be processed and the ozone-water mist solution is heated to temperature T2>T1 at the point of application using radiant heating from top surface. The radiant heating system has be described under FIG. 12. At the end of the spin etch clean cycle, the gate valve 122 is closed and the rinse valve 120 is opened to spin rinse the wafer. At the end of the spin rinse cycle, the rinse valve is closed and the wafer is spun dry.

$3^{nd}$ GROUP: High Performance Ozonated Water Supply for Use in Conjunction with the Preferred Embodiments (FIG. 17 through FIG. 19)

A method of providing a supply of an ozone-water solution with a relatively high dissolved ozone concentration comprising the steps of chilling water to a relatively low predetermined temperature, flowing the chilled water and high concentration ozone gas through into an ozone gas-water contactor to form an ozone-water solution, flowing the undissolved ozone gas out of the contactor, flowing the ozone-water solution out of the contactor to form a supply of ozonated water. The contactor is designed to provide a relatively large surface area to provide for a high rate of mass transfer of the ozone gas into water solution. A relatively large contacting volume can provide sufficient time for a significant portion of the ozone gas to be transported into solution. Preferred embodiments are illustrated in FIG. 17 and FIG. 18. By reducing the DI water temperature from 20 degree C. to 5 degree C. the saturation concentration is increased by a factor of two.

A method of providing a supply of an ozone-water-mist solution with a relatively high dissolved ozone concentration comprising the steps of chilling water to a relatively low predetermined temperature, flowing the chilled water mist through an liquid atomizer to form a chilled water mist, flowing the chilled water mist and high concentration ozone gas through a contacting volume to supply an ozone-water solution mixed with ozone gas at the outlet of the contactor volume. The chilled water mist with very small droplet size provides a relatively large surface area to provide for a high rate of mass transfer of the ozone gas into water solution.

The a relatively large contacting volume can provide sufficient time for a significant portion of the ozone gas to be transported into solution. A preferred embodiment is illustrated in FIG. 19.

Typical Ozone-Water Solution Supply Using Venturi Injector and Downstream Bubble Column Description—FIG. 17

In reference to FIG. 17, a DI water supply 130 is connected through a length of tubing to the fill inlet of a three-way valve 132. The outlet of three-way valve 132 is connected through a length of tubing to the inlet of pump 134. The outlet of pump 134 is connected to the process fluid inlet of heat exchanger 136. A recirculating cooling unit is connected to the working fluid inlet and outlet of the heat exchanger 136. The process fluid outlet of the heat exchanger 136 is connected to the motive flow inlet of venturi injector 140. The outlet of venturi injector 140 is connected to a bubble column inlet 142 in bubble column 144. The pump is a positive displacement pump capable of delivering the pressure to overcome the pressure drop across the exchanger 136 and venturi injector 140. The supply outlet 156 of the bubble contactor 146 is connected by a length of tubing to a liquid back pressure regulator 158. The outlet of liquid back pressure regulator 158 is connected by a length of tubing to two-way valve 160. The outlet of the two-way valve 160 is connected to the process to provide a pressurized source of ozonated water at 162.

An pressurized oxygen supply 164 is connected by a length of tubing to a two-way valve 166. The outlet of two-way valve 166 is connected by a length of tubing to mass flow controller 168. The outlet of mass flow controller 168 is connected to the oxygen gas inlet of high concentration ozone generator 170. A recirculating cooling unit 172 is connected to cool the ozone generator cells of ozone generator 170. The ozone gas outlet of ozone generator 170 is connected to the inlet of check valve 174. The outlet of check valve 174 is connected to the suction gas inlet of venturi injector 140. The waste ozone gas vent outlet 176 of contactor 146 is connected to an ozone catalytic destruction unit 178. The outlet of ozone catalytic destruction unit 178 is connected to the inlet of off-gas back-pressure regulator 180. The outlet of back pressure regulator 180 is connected to the inlet to the facility vent 182 for contactor off-gas. The recirculate-outlet 154 of contactor 146 is connected by a length of tubing to the recirculate inlet of three-way valve 132. An level sensor 148 is positioned several inches from the top of the contactor 146 to detect the position of the minimum liquid level in the contactor. An level sensor 150 is positioned a short distance (1–2 inches) above level sensor 148 to detect the position of the maximum liquid level in the contactor. The level sensors are connected to a fill level controller 152. The fill level controller connected to the fill valve 132, a solenoid valve, to control the filling of the contactor as water is removed from the contactor at the supply point 162. The connection from the controller to the valve is not shown. This embodiment is designed to provide for dissolving ozone gas in water at a pressure above atmospheric to increase the dissolved ozone concentration as predicted by Henry's law. Since the contactor and connecting tubing is chilled below ambient, the entire system is insulated.

In an alternative embodiment, designed to dissolve ozone gas at atmospheric pressure, the liquid back pressure regulator 158 may be eliminated and the gas back pressure regulator 178 is moved to outlet line of the ozone generator 170 to maintain the required pressure in the ozone generator for efficient generation of ozone gas. In this alternative embodiment the contactor is not pressurized. Accordingly, a pump (not shown) must be placed between the contactor supply outlet 156 and the valve 160 to provide a pressurized source of ozonated water at 162. In this case the two-way valve solenoid valve (all valves are understood to be solenoid valves) 160 may be replaced by a three way solenoid valve (not shown) with the normally open outlet connect by a length of tubing back to the contactor 146 and the normally closed outlet connected to 162. In this configuration, the ozonated water can be recirculated back to the contactor (connection not shown) to keep the concentration in the line a full concentration, and then dispensed to the process by actuating the three-way dispense valve (not shown). In electronic device cleaning/processing applictions, all wetted materials may be TEFLON® PFA or Teflon PTFE materials in lieu of metal materials to exclude the introduction of metal contamination into the process.

Operation—FIG. 17

In reference to FIG. 17, DI water at near room temperature flows through the heat exhanger 134 where it may be cooled to a lower temperature (5 degree C. for example). The chilled DI water enters the venturi injector 140 where ozone gas is injected. Oxygen gas under pressure is regulated to a delivery pressure (40 psig. for example) and supplied to the inlet of mass flow controller 168. The mass flow controller controls the mass flow to the inlet of the ozone generator 170. An ozone generator such as the ASTEX AX8100 can deliver ozone at a concentration of about 240 g/NM3 at a flow rate of 1.5 L/min. An ASTEX AX 8200 can deliver ozone at a concentration of about 240 g/NM3 at a flow rate of 4.5 L/min. The ozone gas enters the suction inlet of venturi injector 140 where the high shear forces produce many very small bubbles of ozone gas which move to the bubble contactor with the water flow. The chilled DI water, mixed with ozone gas bubbles, moves through the contactor as shown by the arrows on FIG. 17. The large surface area of the many small bubbles provide for a high rate of mass transfer from the gas to the liquid by diffusion. The residence time of the bubbles in the contactor determines the concentration that can be achieved at the end of one pass through the contactor. The ozone gas that does not dissolve into the water exits form the contactor at the outlet 176. The level controller 152 controls the opening and closing of the fill valve 132. The level of water in the contactor is controlled as water is drawn from the contactor at 162.

An ozonated water supply can be designed to operate either as a batch recirculating dissolved ozone supply system or as a single pass continuous flow dissolved ozone supply system. Both systems have a means for generating high concentration ozone gas, a means for cooling a volume of water, and a means for dissolving the ozone gas in the water.

The key design elements are summarized in Table 18.

TABLE 18

Key Design Elements: Batch Recirculating Compared to a Continuous Flow Ozonated Supply

| Design Element | Batch Ozone Mass Flow Out > Ozone Mass Flow Dissolved | Continuous Ozone Mass Flow Out = Ozone Mass Flow Dissolved |
| --- | --- | --- |
| supply duty cycle | intermittent | continuous |
| ozone generator flow | variable | constant |
| req'd ozone gas mass flow rate | <DIO3 mass flow rate | ≧DIO3 mass flow rate |
| operating temperature | <20 C. or ≧20 C. | <20 C. or ≧20 C. |
| req'd DI water cooling capacity | proportional to average DIO Flow | proportional to peak DIO Flow |
| operating pressure | P = 1 bar or P > 1 bar | P = 1 bar or P > 1 bar |
| gas-liquid contactor element | venturi injector or packed column | venturi injector or packed column |
| gas-liquid contact volume | bubble column or packed column | bubble column or packed column |
| ozone injection pressure | <1 bar or contactor pressure | <1 bar or contactor pressure |
| maximum DIO3 concentration | Cout = saturation concentration | Cout < saturation concentration |
| system cost | lowest | higher |

Let us describe the operation of small batch type ozonated supply system of the type employed in the inventors laboratory. A small venturi injector and bubble column contacting system for dissolving ozone gas at one atmospheric pressure employ a high pressure pump 134 feeding a small venturi injector 140 (Mazzei Injector Model 287) with chilled DI water at a motive flow rate of 3.5 L/min. (See FIG. 17) The water enters the inlet 142 in the center of the internal bubble column 144, then spills over the partition to the outer annular volume between the column 144 and the internal wall of the contactor 146 and returns to the pump by exiting from the outlet 154. Accordingly, the pump 134 continuously circulates water in a closed loop from the contactor 146, through the venturi injector 140 at a flow rate of about 3.5 L/min, and back to contactor bubble column 144. Once refilled with fresh water, the concentration can be restored to saturation in about 20 to 30 minutes for a ozone flow rate of 0.48 L/min at a gas phase ozone concentration of 240 g/NM3 and a contactor volume of 12 liters.

A pressure of about 40 psig is required to pass a motive flow of 3.5 L/min through the venturi in a system with an unpressurized contactor (p=1 bar=14.5 psia). Ozone gas from the ozone gas delivery system is fed to the suction inlet port of the venturi at a flow rate of 0.5 Liters/min. The pressure at the suction port of the venturi is about 0.7 to 0.8 bar (aprox. 10 to 12 psia). The injection conditions are summarized in Table 19 below. In a recirculating system of this type, the dissolved ozone concentration in the contactor starts from zero and rises exponentially to a maximum saturation value which is determined by Henry's law given the ozone gas concentration and pressure and the water temperature. In an unpressurized system, the ozone gas is dissolved at 1 bar=14.5 pisa. For the flow rates and concentrations specified, the exponential time constant with which the dissolved ozone concentration approaches saturation is about 6 to 7 minutes. Accordingly, one can produce a 12 liter batch of ozonated water at a concentration of about 95% of saturation is 20 minutes (about three time constants). The key design parameters for this small capacity batch system are summarized in Table 19. Much larger capacity systems with higher mass flow rates can be designed using the same approach.

TABLE 19

Flows, Pressures, and Venturi Injector Size for a venturi-based ozone gas-water contacting system for dissolving ozone gas at a pressure 1 bar and a flow rate of 0.48 L/min. The predicted saturation concentration with a water temperature of 5 degree C. and ozone gas concentration of 240 g/Nm3 is also shown

| PARAMETER | Injector Design Values |
| --- | --- |
| venturi outlet/contactor pressure (bar) | 1 bar |
| venturi outlet pressure - pisa (psig) | 43.5 (28.8) |
| Injector (ozone) flow - liters/mm (ft3/hr) | .48 (1.0) |
| Venturi Inlet Pressure - psig | 40 |
| Motive (water) flow - liters/mm (gpm) | 3.5 (.8) |
| Pump Pressure Boost Required - psig | 40 |
| Venturi Size (Mazzei Model Number) | Model 287 |
| Predicted Saturation Concentration | 109 mg/L |

If the mass flow rate of the ozone to the injector is increased by increasing the ozone gas flow rate at a given gas phase concentration, then the volume of water will approach saturation in a shorter time. For example, the ASTEX® AX 8100 ozone generator can supply ozone at a concentration of about 240 g/Nm3 at a flow rate of 1.5 L/min at a generator power setting of 90%. An ASTEX® AX8200 ozone generator has three times the capacity of an AX8100 and can supply ozone at a concentration of about 240 g/Nm3 at a flow rate of 4.5 L/min at a generator power setting of 90%. The mass transfer rate from the gas to the liquid is a function of the surface area and the concentration difference between the gas phase and liquid phase. Accordingly, the mass transfer rate gradually falls as the dissolved concentration rises.

The entire ozone gas-water contacting system may be enclosed in a 19 inch equipment rack equipped with a ventilation system and a safety interlock system employing ozone leak detection sensors. In a system designed for use in semiconductor applications all the wetted parts can be TEFLON® or PVDF to eliminate iron contamination associated with stainless steel components.

The contactor can be either pressurized or unpressurized. If the contactor is designed to withstand pressures above one atmosphere, then the ozone gas can be dissolved in water at elevated pressures and thereby produce a higher dissolved ozone concentration at a given ozone gas phase concentration and water temperature than can be achieved at one atmosphere. For example, ozone can be dissolved in water at 4 bar (58 psia) In this case the pump provides boost pressure above the contactor pressure and the venturi is selected to achieve adequate suction at desired ozone flow rate. In Table 20, below we have presented the parameters for a high pressure venturi-based ozone gas-water contacting system for dissolving ozone gas at a pressure 3, or 4 bar and a flow rate of 1.5 L/min or 4.5 L/min. In such a system the off gas from the contactor must exit from the pressurized contactor through a back pressure regulator set to the desired contactor pressure and the liquid stream that is dispensed to the process must also exit from the contactor through a back pressure regulator set to the desired contactor pressure as shown in FIG. 17.

TABLE 20

Flows, Pressures, and Venturi Injector Size for a venturi-based ozone gas-water contacting system for dissolving ozone gas at a pressure 3, or 4 bar and a flow rate of 1.5 L/min or 4.5 L/min. The predicted saturation concentration with a water temperature of 5 degree C. and ozone gas concentration of 240 g/Nm3 is also shown

| PARAMETER | Injector Design Values | | | |
|---|---|---|---|---|
| venturi outlet/contactor pressure (bar) | 3 bar | 4 bar | 3 bar | 4 bar |
| venturi outlet pressure - pisa (psig) | 43.5 (28.8) | 58 (43.3) | 43.5 (28.8) | 58 (43.3) |
| Injector (ozone) flow - liters/min (ft3/hr) | 1.5 (3.2) | 1.5 (3.2) | 4.5 (9.6) | 4.5 (9.6) |
| Venturi Inlet Pressure - psig | 70 | 100 | 90 | 120 |
| Motive (water) flow - liters/min (gpm) | 14.5 (3.8) | 17.2 (4.5) | 29.5 (7.8) | 35.6 (9.4) |
| Pump Pressure Boost Required - psig | 41.2 | 56.7 | 46.5 | 76.7 |
| Venturi Size (Mazzei Model Number) | Model 484 | Model 484 | Model 584 | Model 584 |
| Predicted Saturation Concentration at T = 5 Deg C. w/ozone gas at 240 g/Nm3 | 327 mg/L | 436 mg/L | 327 mg/L | 436 mg/L |

If one can use a concentration that is less than the saturation concentration, then one can achieve that concentration in a shorter time. This is the basis of a single pass ozone gas-water contacting system.

Typical Ozone-Water Solution Supply Using a Packed Column

Description—FIG. 18

In reference to FIG. 18, the design of a single pass ozonated water supply using a packed column is shown. The chilled water supply subsystem (elements 130, 132, 134, 136, and 138) is the same as described under FIG. 17 except valve 132 is a two way valve in a single pass configuration. The design of the ozone gas subsystem (elements 164, 166, 168, 170, and 172) is the same as described under FIG. 17. The design of the off-gas subsystem with gas back pressure regulator (elements 178, 180, and 182 is the same as described under FIG. 17. The design of the column level control subsystem (elements 148, 150, and 152) is the same as described under FIG. 17. The design of the supply outlet to the process (elements 156, 158, 160) is the same as described under FIG. 17. Since this system is design for a single pass there is not recirculation of the ozonated water back through the contactor.

The systems differ only in the type of contactor used. In reference to FIG. 18, the ozone gas from generator 170 is connected by a length of tubing through a check valve 174 to the inlet of a gas distributor plate 174 located in the bottom of a pack column contactor filled with PFA packing. The packing is typically about $\frac{1}{10}^{th}$ the column diameter. The sizing of the packing and column for a particular gas and liquid flow rate is well known to those skilled in the art.

The process outlet of heat exchanger 136 supplies the chilled DI water to the packed column contactor 146 at a point near the top of the contactor.

Operation—FIG. 18

In reference to FIG. 18, the operation of the subsystems which are the same as those shown in FIG. 17 are the same as described under FIG. 17. Whereas the venturi injector produces many small bubbles to provide a large surface area for mass transfer to occur in a downstream bubble column as described under FIG. 17, the column packing provides the large surface area for mass transfer in the packed column design. In a single pass design the volume of the column is made relatively large (greater than 20 liters for a system designed to produce ozononated water at a concentration of 70 mg/L at a liquid flow rate of 10 L/min and a water temperature of 20 degree C. One cannot simply decrease the water temperature to produce a higher dissolved ozone concentration in a single pass contactor. If one decreases the DI water temperature from 20 degree C. to 5 degree C., then one doubles the capacity for the water to dissolve a given mass of ozone. In order to realize a benefit from this increased capacity one must double the mass flow rate supplied by the ozone generator by using a larger generator capable of supplying a concentration of 240 mg/L at a flow rate of 12 L/min as compared to 6 L/min for example. One may also increase the column size to accommodate the higher flow rate.

We have presented a method of producing an ozone-solvent solution with a very high dissolved ozone concentration for use in industrial applications comprising the following steps:

a) cooling a volume of solvent (particulary an aqueous solution) to a temperature below room temperature but above the freezing point of the solvent, e.g. water between 1 deg. C. and 15 deg. C., b) dissolving ozone gas in said volume of solvent under elevated pressure using an ozone gas-water contacting means to form an ozone-solvent solution c) dispensing the low temperature ozone-solvent solution to a process chamber whereby the ozone-solvent solution can have a much higher dissolved ozone concentration than can an ozone-solvent solution formed at the same pressure at room temperature.

The preferred embodiments described in FIGS. 1 to 15 will be able to derive significant benefit from a supply of a very high concentration cold ozone water solution. This new class of ozonated water supply systems have the potential to achieve a factor of two increased in concentration compared to prior art supply systems operating at 20 degree C.

This new class of ozonated water supplies has a number of advantages:

this approach provides a means to increase the dissolved concentration to levels a factor of two higher than can be produced at near room temperature;

a cold ozone water solution temperature reduces the rate of thermal decay of the ozone in solution over that in a 20 degree C. solution;

a cold ozone water solution can be piped relatively long distances in suitably insulated lines;

a supply of cold ozone water solution with a factor of two higher dissolved ozone concentration transports a given ozone mass flow using half the water as a conventional supply;

a factor of two high dissolved ozone concentration will enable a new class of applications to achieve a factor of two increase in etch rate over that which can be achieved currently;

applications will be able to consume less water to process a wafer or substrate or other material than the same application supplied from a supply system which runs at near room temperature because a given ozone mass flow can be carried at a lower water flow rate if the dissolved ozone concentration is higher;

Since the water flow rate can be reduced by a factor of two, the pressure drop across the point-of-use heater (heat exchanger or direct heater) is reduced by about a factor of 4. In the current configuration this means the pressure at the outlet of the dissolved ozone supply is reduced from about 95 psig for a flow rate of 3.3 L/min to about 27 psig for a flow rate of 1.65 L/min. (This eliminates the need to boost the pressure at the exchanger inlet with a pump or other means. An ozone-water contactor pressure of about 2.5 bar or more is adequate to supply this pressure with no additional boost);

since the water flow rate can be reduced by a factor of two the power requirement of the point-of-use heater is reduced by a factor of two as shown in the table 21 below. At a flow rate of 1.65 L/min the required power input to the water stream to increase the temperature 50 degree C. is 5.7 kW. At a flow rate of 3.3 L/min the required power input to the water stream to increase the temperature 50 degree C. is 11.4 kW.

TABLE 21

Example Heater Power Requirements

| Dispense Flow Rate (L/min) | Inlet Water Temp. (deg. C.) | Desired Outlet Water Temp. (deg. C.) | Required Temp. Increase (deg. C.) | Power Input Req'd (kW) |
|---|---|---|---|---|
| 1.65 | 5 | 45 | 40 | 4.55 |
| 1.65 | 5 | 55 | 50 | 5.7 |
| 1.65 | 5 | 65 | 60 | 6.85 |
| 1.65 | 5 | 75 | 70 | 7.95 |
| 1.65 | 5 | 85 | 80 | 9.1 |
| 1.65 | 5 | 95 | 90 | 10.25 |
| 3.3 | 5 | 45 | 40 | 9.1 |
| 3.3 | 5 | 55 | 50 | 11.4 |
| 3.3 | 5 | 65 | 60 | 13.7 |
| 3.3 | 5 | 75 | 70 | 15.9 |
| 3.3 | 5 | 85 | 80 | 18.2 |
| 3.3 | 5 | 95 | 90 | 20.5 | since the water flow rate can be reduced by a factor of two, the pressure drop across the DI water cooling heat exchanger is reduced by about a factor of 4; this eliminates the need for pump or other means to boost the DI water pressure at the system inlet over that available from the facility DI water supply.

since the water flow rate can be reduced by a factor of two the power requirement of the DI water cooling unit is reduced by a factor of two as shown in the table below. At a flow rate of 1.65 L/min the required power withdrawal from the water stream to decrease the temperature 15 degree C. is 1.7 kW. At a flow rate of 1.65 L/min the required power withdrawal from the water stream to decrease the temperature 15 degree C. is 3.4 kW. With a system feeding three process modules, the total DI water flow to the contactor is 5.0 L/min. The cooling power is shown in the table 22 below.

TABLE 22

Example Heater Power Requirements for Lower Flow Rates

| DI water Flow Rate (L/min) | Inlet Water Temp. (deg. C.) | Desired Outlet Water Temp. (deg. C.) | Required Temp. Increase (deg. C.) | Power Removal Req'd (kW) |
|---|---|---|---|---|
| 1.65 | 20 | 5 | 15 | 1.7 |
| 3.3 | 20 | 5 | 15 | 3.4 |
| 5 | 20 | 5 | 15 | 5.1 |
| 10 | 20 | 5 | 15 | 10.2 |

If a solute, a buffer or hydroxyl radical scavenger chemical, is added to the water before it is cooled, then the freezing point may be reduced to below 0 degree C. Accordingly, in general the water may be cooled to a point above freezing point of the aqueous solution.

Method of Dissolving Ozone Gas into Water Chilled Water Mist to from an Ozone-Water Mist Solution Mixed with Ozone Gas Description—FIG. 19

In reference to FIG. 19, the design of a supply of chilled ozone-water mist mixed with ozone gas is shown. The chilled water supply subsystem (elements 130, 132, 134, 136, and 138) is the same as described under FIG. 17 except valve 132 is a two way valve in a single pass configuration. The design of the ozone gas subsystem (elements 164, 166, 168, 170, and 172) is the same as described under FIG. 17. In reference to FIG. 19, the ozone gas from generator 170 is connected by a length of tubing to the inlet of a check valve 174. The outlet of check valve 174 is connected through the inlet 194 of the ozone gas-water mist contactor 192 to gas distributor plate 196 located inside of ozone gas-water mist contactor. The process outlet of heat exchanger 136 is connected through the inlet 188 of the of the ozone gas-water mist contactor 192 to the water fog/mist nozzle 190 located inside of ozone gas-water mist contactor. The contactor drain outlet 202 is connected by a length of tubing through a trap 54 to the facility drain 56. The outlet 198 of the ozone gas-water mist contactor 192 is connected by a short large diameter (approximately 20 cm long, 10 cm diameter) length of tubing to the process.

Operation—FIG. 19

In reference to FIG. 19, the design of a supply of an ozone-water-mist solution with a relatively high dissolved ozone concentration is shown. The DI water, or DI water mixed with additional injected chemicals, is chilled by the heat exchanger 136 to a relatively low predetermined temperature such as 5 degree C. The chilled water is flowed through water fog/mist nozzle 190 to form a chilled water mist in the ozone gas-water mist contactor 192. The ozone gas is supplied by the subsystem comprising elements 164, 166, 168, 170, and 172 to the inlet of the gas distributor plate 196 located inside of the ozone gas-water mist contactor 192. The chilled water mist and high concentration ozone gas flow through the contacting volume to supply a chilled ozone-water mist mixed with ozone gas at the outlet 198 of the contactor volume. The chilled water mist with very small droplet size provides a relatively large surface area to provide for a high rate of mass transfer of the ozone gas into water solution. The relatively large contacting volume can provide sufficient time for a significant portion of the ozone gas to be transported into solution. A relatively small portion of the mist will contact the walls of the contactor and be drained from the contactor by the drain line.

General Comments

In many instances in the above description of the preferred embodiments any elements that are between the inlet of the heater 28 or 29 and the dispense nozzle 36 are said to be connected by a short length of tubing. The critical requirement is actually the volume of the tubing not the length because, at a given flow rate, the time delay between the time the ozone-water solution is heated, transported through the connecting tubing to the point of application of the material to be oxidized. When we say short length of tubing we are really saying small volume length of tubing. The tubing length and internal diameter is chosen such that the total time is such that the dissolved ozone concentration does not fall by more that a predetermined amount at a chosen process temperature. In many early embodiments constructed by the inventors the tubing was TEFLON® with an inside diameter of between 0.125 inches to 0.180 inches. The tubing connecting the various elements was between 2 to 10 inches long such that the total residence time in the heater and interconnecting tubing was less than 5 seconds for example at a particular flow rate through the point-of-use heater. At a dispense temperature of 50 degree C. the inventors estimated that the dissolved ozone concentration would decrease to about 80 percent of its initial value at the inlet of the point-of-use heater. In all the embodiments shown in all the figures the valves may be gas operated or electrically operated solenoid valves so that the valves can be controlled with a central controller. In all the embodiments, one or more controllers may be included to control the time, duration, and other process parameters during each phase of the materials processing cycle. Many of the embodiments include a three-way valve 24 to direct the chilled ozone-water solution to waste reclaim and a three-way valve 32 to direct the heated ozone-water solution to waste reclaim. In some embodiments one or both of these valves may be omitted. In most of the embodiments shown, a heat exchanger 28 is shown has the point-of-use heater. In all cases it should be noted that a point-of-use heat heater 29 may be used in lieu of a heat exchanger 28. In many embodiments, typical values for process parameters are given. In many cases the process parameters may be set outside the range of parameters listed. For example, if the means of applying the ozonated water solution to the wafer can provide a higher mass transport rate M, then the temperature at which the etch rate will become mass transport limited will be higher also. In some cases we have shown a range of temperatures around a nominal value (for example 40 to 60 degree C.) as a typical temperature at the point of application. This is a nominal value for a particular heating delay time and mass transport condition. If the mass transport conditions are improved, then the etch rate may be increased with a further increase in temperature. In some configurations, the etch rate may not become mass transport limited until the temperature is set to a higher value such as 90 to 95 deg. C. for example. Although specific features of the preferred embodiments are shown in some drawings and not others, this is for convenience only as many features may be combined with any or all of the other features.

Particular mention is made of conditions pertaining to processing semiconductor wafers, especially the removal of photoresist, post etch residue, and other organic materials from semiconductor wafers. Particular mention is made of conditions pertaining to sterilizing or disinfecting medical instruments, medical devices. However, aspects of the present invention may be practiced in other applications. The contents of the preceeding discussion and the drawing are set forth as examples only and should not be understood to represent limitations upon the scope of the present invention.

What is claimed is:

1. A method for treating a material, comprising:
   forming an ozone-solvent solution at a first temperature;
   passing said ozone-solvent solution through a heater to heat said ozone-solvent solution from said first temperature to form a heated [−]ozone-solvent solution relative to said first temperature, such that said heated ozone-solvent solution is supersaturated with ozone; and
   reacting the supersaturated heated ozone-solvent solution with the material at a second temperature;
   wherein the first temperature is less than the second temperature.

2. The method of claim 1, wherein said ozone-solvent solution is formed at said first temperature by dissolving an ozone gas in solvent at said first temperature to form a first concentration of dissolved ozone.

3. The method of claim 1, wherein the second temperature is at least 5 degrees Celsius greater than the first temperature.

4. The method of claim 1, wherein reacting said supersaturated heated ozone-solvent solution with the material comprises applying the supersaturated heated ozone-solvent solution to the material using at least one nozzle.

5. The method of claim 1, wherein reacting the supersaturated heated ozone-solvent solution with the material comprises immersing the material within the supersaturated heated ozone-solvent solution.

6. The method of claim 1, wherein said step of reacting said supersaturated heated ozone-solvent solution with said material has at least one point of reaction, and wherein the heater comprises using a liquid-to-liquid heat exchanger placed just upstream of the at least one point of reaction of said supersaturated heated ozone-solvent solution with said material.

7. The method of claim 1, wherein said step of reacting said supersaturated heated ozone-solvent solution with said material has at least one point of reaction, and wherein the heater comprises an in-line heater placed just upstream of the at least one point of reaction of said supersaturated heated ozone-solvent solution with said material.

8. The method of claim 1, further comprising:
   injecting a chemical into said supersaturated heated ozone-solvent solution prior to reacting said supersaturated heated ozone-solvent solution with said material.

9. The method of claim 1, wherein said material comprises a substrate, and wherein the step of reacting said supersaturated heated ozone-solvent solution with said substrate comprises:
   spinning said substrate to achieve a rotational speed about an axis; and
   dispensing said supersaturated heated ozone-solvent solution over at least a portion of at least one surface of the spinning substrate using at least one nozzle.

10. The method of claim 1, wherein said material comprises a substrate, said method further comprising the step of rinsing the substrate after the substrate is reacted with said supersaturated heated ozone-solvent solution.

11. The method of claim 1, wherein the material comprises a planar substrate selected from the group consisting of semiconductor wafers, flat panel displays, memory discs, substrates for use in an electronic device.

12. The method of claim 1, wherein the material is selected from the group consisting of photoresist, post etch resist residue, post etch residue, anti-reflective coating, organic contamination.

13. The method of claim 1, wherein said step of reacting said supersaturated heated ozone-solvent solution with said material comprises passing said supersaturated heated ozone-solvent solution through an orifice that directs said supersaturated heated ozone-solvent solution toward said material, and wherein the heater is placed just upstream of said orifice.

14. The method of claim 1, further comprising:
injecting a chemical into said ozone-solvent solution prior to passing said ozone-solvent solution through said heater.

15. The method of claim 1, further comprising passing said supersaturated heated ozone-solvent solution through at least one element selected from the group consisting of a back pressure regulator, a pressure dropping nozzle, and a valve, prior to applying the supersaturated heated ozone-solvent solution to the material.

16. The method of claim 2, wherein said supersaturated heated ozone-solvent solution is reacted with the material within a time period after heat is first applied to said ozone-solvent solution in said heater to minimize a decrease in the concentration of the dissolved ozone in the supersaturated heated ozone-solvent solution.

17. The method of claim 3, wherein the first temperature is between 1 and 30 degrees Celsius.

18. The method of claim 3, wherein the first temperature is between 1 and 10 degrees Celsius.

19. The method of claim 3, wherein the second temperature is between 30 and 95 degrees Celsius.

20. The method of claim 3, wherein the second temperature is between 35 and 65 degrees Celsius.

21. The method of claim 8, wherein the chemical comprises a hydroxyl radical scavenger.

22. The method of claim 8, wherein the chemical comprises an element selected from the group consisting of a pH buffer, an acid, and a base.

23. The method of claim 8, wherein the chemical comprises a corrosion inhibitor.

24. The method of claim 8, wherein the chemical comprises a surfactant.

25. The method of claim 9, wherein said at least one nozzle is positioned on said axis.

26. The method of claim 9, wherein a plurality of nozzles are positioned in a plurality of positions over the substrate.

27. The method of claim 9, further comprising the step of moving said nozzle relative to said substrate.

28. The method of claim 9 wherein said at least one nozzle is successively positioned at one or more positions relative to the center of rotation of said substrate.

29. The method of claim 16, wherein the time period is such that the concentration of the supersaturated heated ozone-solvent solution at said second temperature is greater than if said ozone-solvent solution had been formed at said second temperature.

30. The method of claim 16, wherein the time period corresponds to no more than a 20 percent decrease in the concentration of the dissolved ozone in the supersaturated heated ozone-solvent solution from said first concentration.

31. A method for oxidizing a material, comprising:
forming an ozone-solvent solution at a first temperature;
passing the ozone-solvent solution through a heater to heat said ozone-solvent solution from the first temperature to form a supersaturated heated ozone-solvent solution; and
after the step of heating the ozone-solvent solution, reacting the supersaturated heated ozone-solvent solution with the material at approximately a second temperature to oxidize the material wherein the first temperature is less than the second.

32. The method of claim 31, further comprising rinsing the material.

33. The method of claim 31, wherein the second temperature is at least 5 degrees Celsius greater than the first temperature.

34. The method of claim 31, wherein the first temperature is between 1 and 30 degrees Celsius.

35. The method of claim 31, wherein the second temperature is between 30 and 95 degrees Celsius.

36. The method of claim 31, wherein reacting the ozone-solvent solution with the material comprises applying the supersaturated heated ozone-solvent solution to the material.

37. The method of claim 31, further comprising:
injecting a chemical into the supersaturated heated ozone-solvent solution prior to applying the supersaturated heated ozone-solvent solution to the material.

38. The method of claim 31, further comprising:
injecting a chemical into said supersaturated heated ozone-solvent solution prior to reacting said supersaturated heated ozone-solvent solution with said material.

39. The method of any one of claims 1–21, claims 17–6, claim 8, claims 22–25, claims 9–12, claims 32–37, claim 38, claim 28, claim 13, claims 38–29, and claim 15 further comprising:
removing undissolved ozone gas prior to the step of passing said ozone solvent solution through said heater.

* * * * *